US011285137B2

(12) United States Patent
Kolesnick et al.

(10) Patent No.: US 11,285,137 B2
(45) Date of Patent: Mar. 29, 2022

(54) ENHANCEMENT OF TUMOR RESPONSE TO CHEMOTHERAPY BY ACTIVATION OF THE ASMASE/CERAMIDE PATHWAY THROUGH TIMED ADMINISTRATION OF A SHORT-ACTING ANTI-ANGIOGENIC AGENT

(71) Applicant: Memorial Sloan-Kettering Cancer Center, New York, NY (US)

(72) Inventors: Richard Kolesnick, New York, NY (US); Adriana Haimovitz-Friedman, New York, NY (US); Evis Sala, New York, NY (US); Zvi Fuks, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/516,235

(22) Filed: Jul. 18, 2019

(65) Prior Publication Data
US 2020/0188376 A1 Jun. 18, 2020

Related U.S. Application Data

(63) Continuation of application No. 15/525,856, filed as application No. PCT/US2015/060486 on Nov. 12, 2015, now Pat. No. 10,413,533.

(60) Provisional application No. 62/078,280, filed on Nov. 11, 2014.

(51) Int. Cl.
| A61K 31/4439 | (2006.01) |
| A61K 31/337 | (2006.01) |
| A61K 31/7068 | (2006.01) |
| A61P 35/00 | (2006.01) |
| A61K 31/404 | (2006.01) |
| A61K 31/7048 | (2006.01) |
| A61K 45/06 | (2006.01) |
| C12Q 1/48 | (2006.01) |
| G01N 33/574 | (2006.01) |

(52) U.S. Cl.
CPC ........ *A61K 31/4439* (2013.01); *A61K 31/337* (2013.01); *A61K 31/404* (2013.01); *A61K 31/7048* (2013.01); *A61K 31/7068* (2013.01); *A61K 45/06* (2013.01); *A61P 35/00* (2018.01); *C12Q 1/485* (2013.01); *G01N 33/57488* (2013.01); *G01N 2800/52* (2013.01)

(58) Field of Classification Search
CPC ............ A61K 31/7048; A61K 31/4412; A61K 31/4439; A61K 31/337; A61K 31/404; A61K 31/7068; A61K 45/06; A61P 35/00; C12Q 1/485
See application file for complete search history.

(56) References Cited

FOREIGN PATENT DOCUMENTS

JP 2001-072589 A 3/2001

OTHER PUBLICATIONS

Siu et al., Clin. Cancer Res., 2006, 12(1), p. 144-151. (Year: 2006).*
Van der Veldt et al., Cancer Cell, 2012, 21, p. 82-91. (Year: 2012).*
Bergh et al., "First-Line Treatment of Advanced Breast Cancer With Sunitinib in Combination With Docetaxel Versus Docetaxel Alone: Results of a Prospective, Randomized Phase III Study," J. Clin. Oncol., 30:921-929 (2012).
Stancevic et al.: "Adenoviral Transduction of Human Acid Sphingomyelinase into Neo-Angiogenic Endothelium Radiosensitizes Tumor Cure", Plos One, vol. 8, No. 8, Aug. 2, 2013 (Aug. 2, 2013), p. e69025, XP055475894.
Casneuf et al., "Antiangiogenic versus cytotoxic therapeutic approaches in a mouse model of pancreatic cancer: an experimental study with a multitarget tyrosine kinase inhibitor (sunitinib), gemcitabine and radiotherapy," Oncology Reports, (22), pp. 105-113 (2009).
Dumitru et al., "Lysosomal ceramide mediates gemcitabine-induced death of glioma cells," J. Med. Mol., 87, pp. 1123-1132 (2009).
Houk et al., "A Population Pharmacokinetic Meta-analysis of Sunitinib Malate (SU11248) and Its Primary Metabolite (SU12662) in Healthy Volunteers and Oncology Patients," Clin. Cancer Res., 15(7) pp. 2497-2506 (Apr. 1, 2009).
Truman et al.; "Endothelial Membrane Remodeling Is Obligate for Anti-Angiogenic Radiosensitization during Tumor Radiosurgery", Plos One, vol. 5, No. 8, Aug. 19, 2010 (Aug. 19, 2010), p. e12310, XP055475950.
Salvador J et al.: "Final results of a phase II study of paclitaxel, bevacizumab, and gemcitabine as first-line therapy for patients with HER2-negative metastatic breast cancer", Clinical and Translational Oncology, Springer Italia Srl, Italy, Spain, vol. 17, No. 2, Aug. 14, 2014 (Aug. 14, 2014), pp. 160-166, XP035442561.

(Continued)

*Primary Examiner* — Jonathan S Lau
(74) *Attorney, Agent, or Firm* — Foley & Lardner LLP

(57) ABSTRACT

Disclosed is a method for enhancing tumor response to chemotherapy, the method comprising administering a short-acting anti-angiogenic agent (AAA) capable of activating ASMase to a subject afflicted with a solid tumor, and thereby creating a time interval of increased susceptibility of said tumor to one or more chemotherapeutic agents, followed by administration of at least one chemotherapeutic agent within the interval. The interval can be defined in terms of a short-duration activation of ASMase signaling by the AAA. Disclosed are also methods for predicting the tumor response in a patient afflicted with a solid tumor to a chemotherapeutic agent, using as an indicator of the response ASMase level or activity (or ceramide level) in the patient following the administration of the chemotherapeutic agent to the patient, or dynamic IVIM based DW-MRI to measure perfusion alterations following administration of the chemotherapeutic agent.

26 Claims, 27 Drawing Sheets

(56) References Cited

OTHER PUBLICATIONS

Sawada et al., "Ordering of ceramide formation, caspase activation, and Bax/Bcl-2 expression during etoposide-induced apoptosis in C6 glioma cells," Cell Death and Differentiation, 7, pp. 751-772 (2000).
Rao et al.: "Axitinib sensitization of high Single Dose Radiotherapy", Radiotherapy and Oncology, vol. 111, No. 1, Apr. 1, 2014 (Apr. 1, 2014), pp. 88-93, XP055476350.
Tsimberidou et al., "Intraperitoneal and Intravenous Chemotherapy in Peritoneal Carcinomatosis," Hepato-Gastroenterology, 59, pp. 960-964 (2012).

* cited by examiner

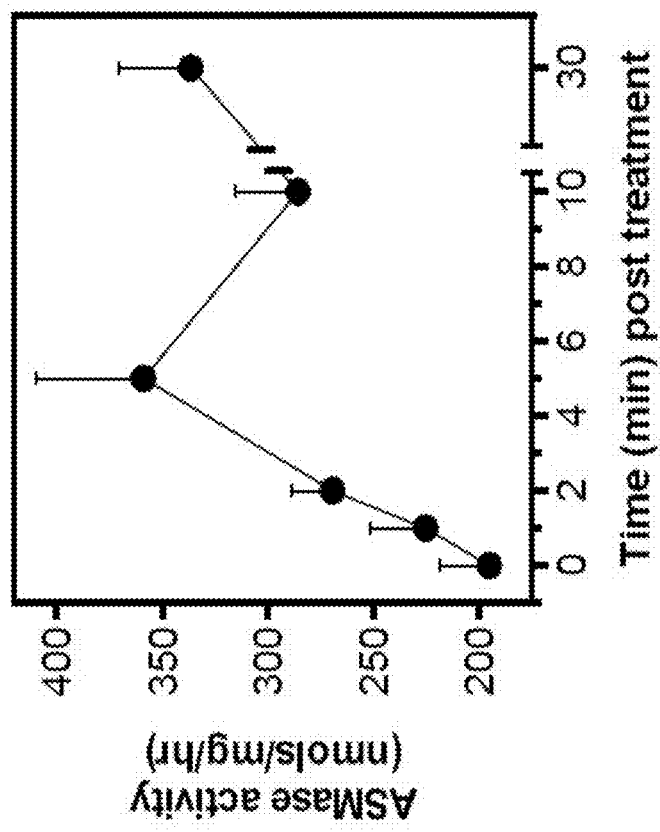
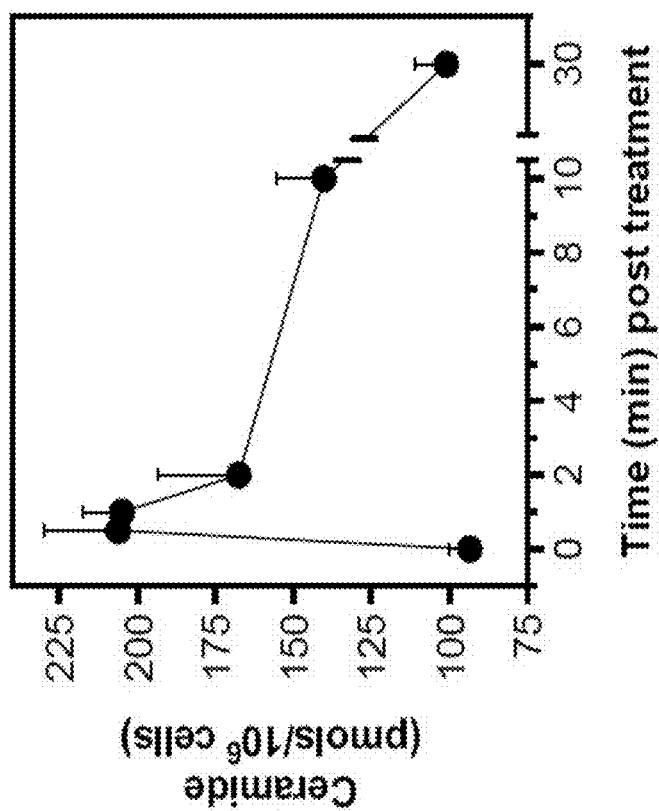
FIG. 1A
FIG. 1B

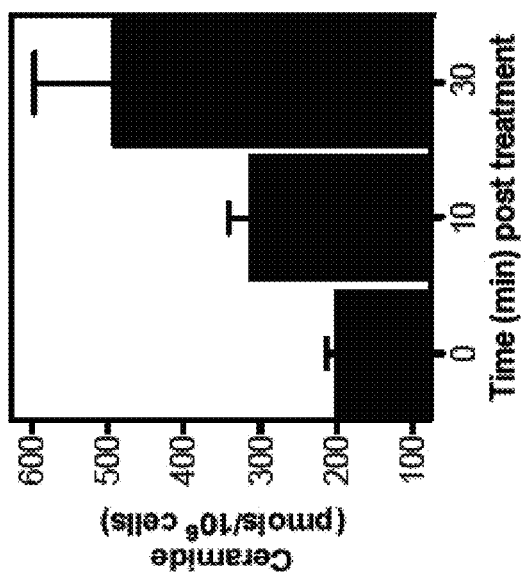
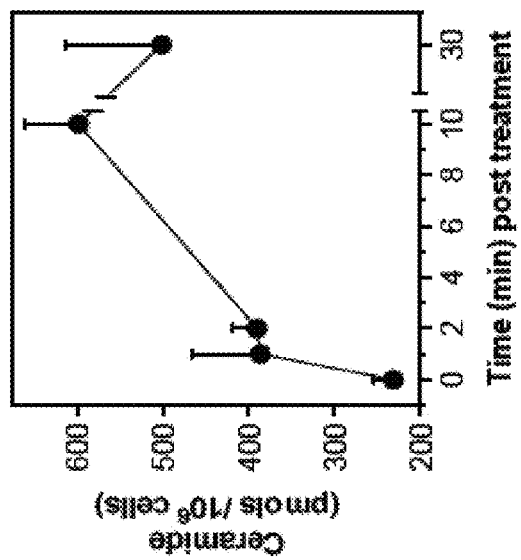
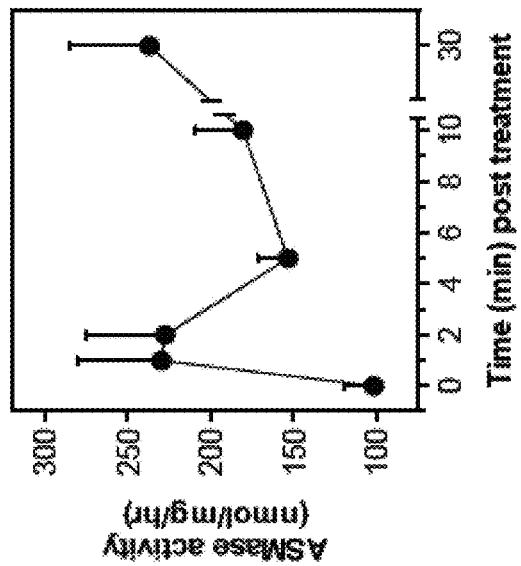

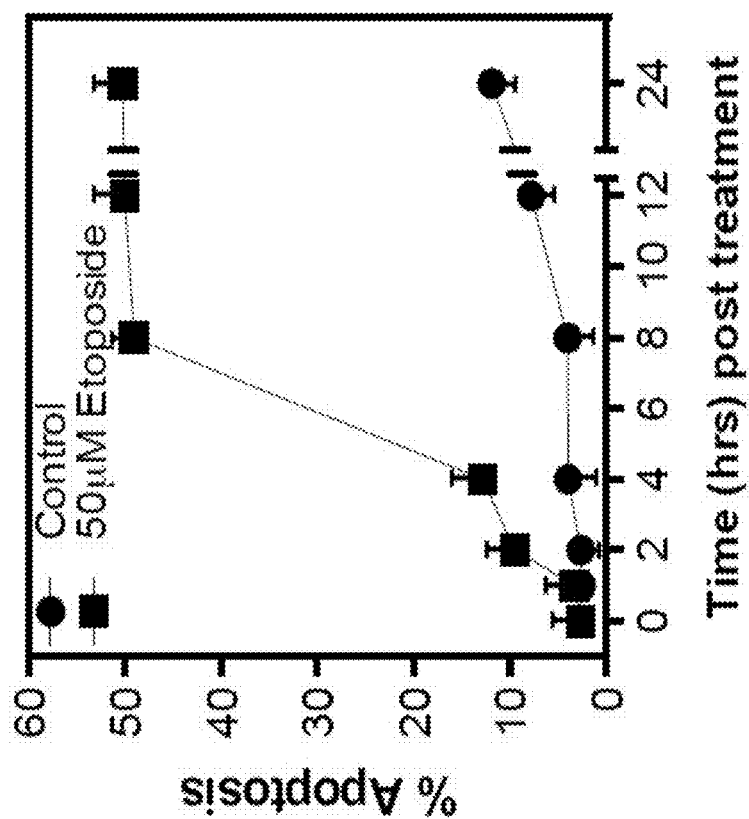
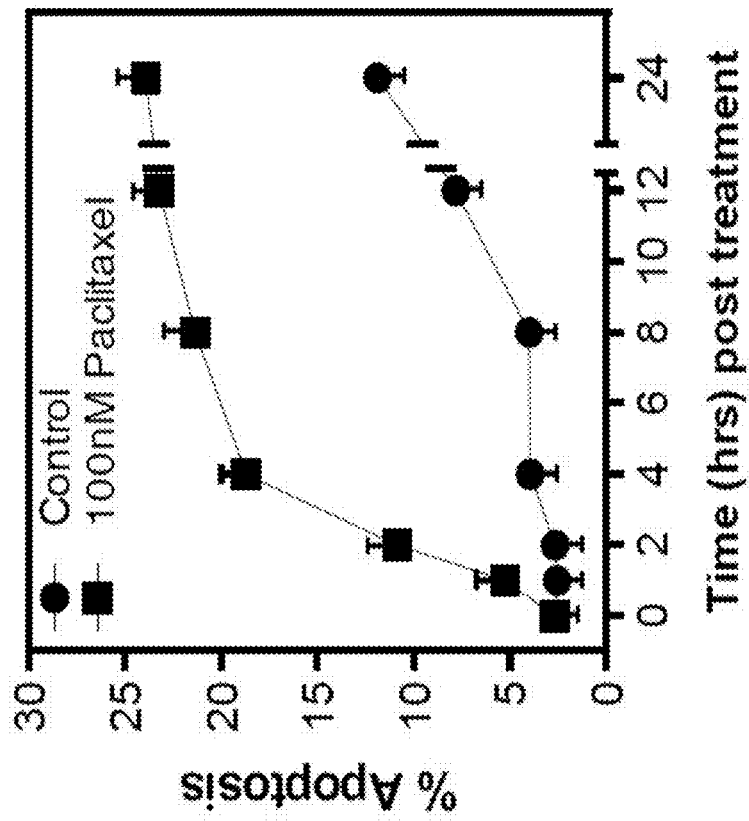
FIG. 2A
FIG. 2B

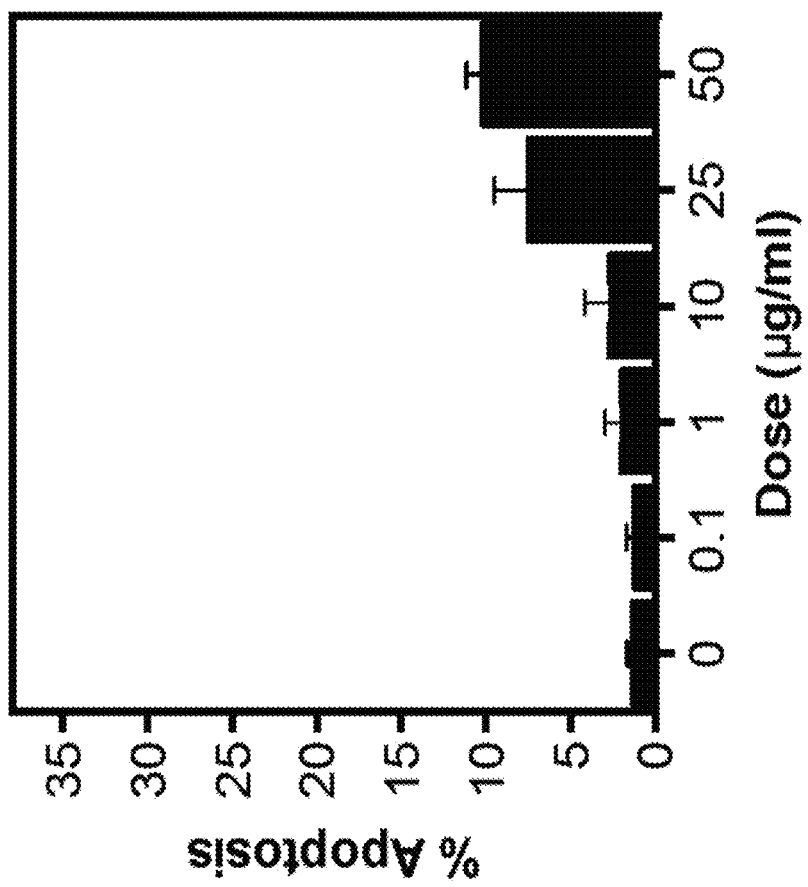

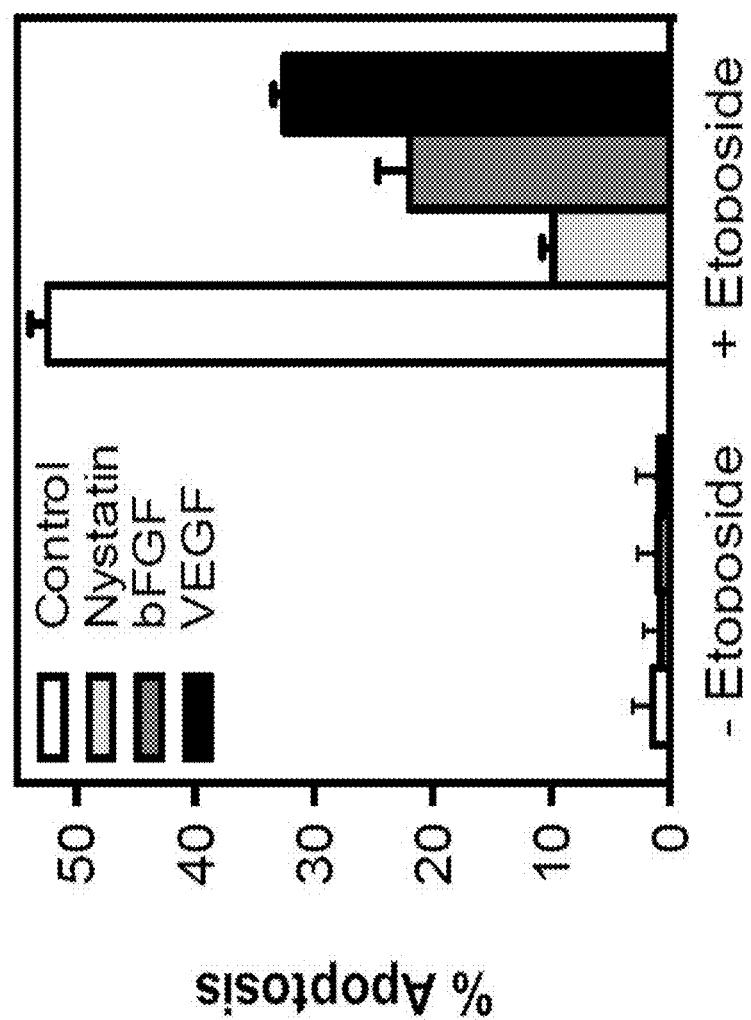

<u>Patient Demographics</u>
Total patients 38
Male 19 (50%)
Female 19 (50%)

Age:
median 55
range 24-75

Tumor type:
Leiomyosarcoma 18 (47%)
Undifferentiated pleomorphic sarcoma 15 (39%)
Angiosarcoma 4 (11%)
Liposarcoma 1 (3%)

Volumetric Analysis:
Evaluable patients 38

Placebo cohort 8
Immediate cohort 16
1 Hour cohort 14

Baseline 3 Months 6 Months

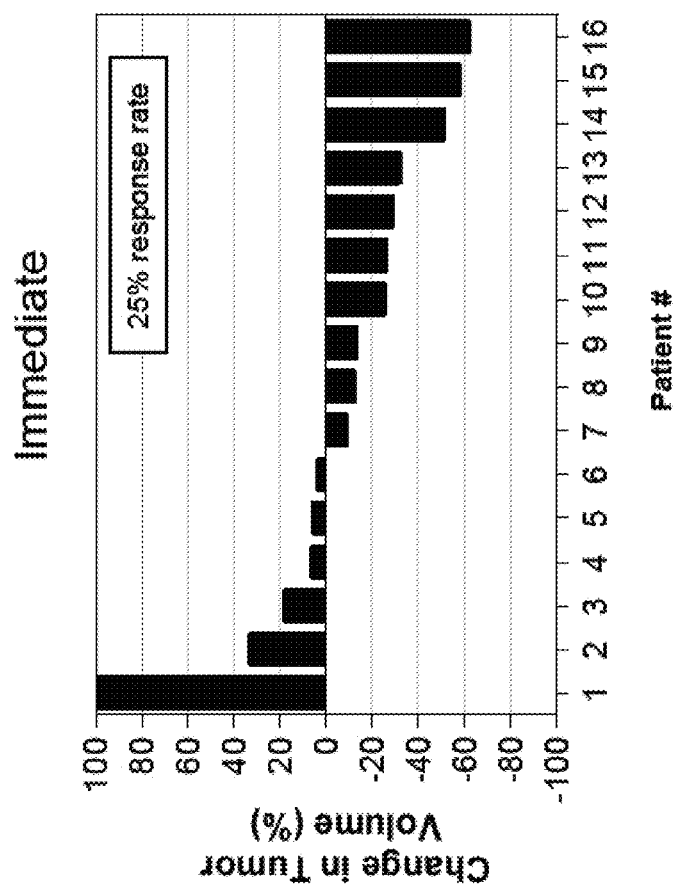
FIG. 7E Immediate
FIG. 7F 1 Hour

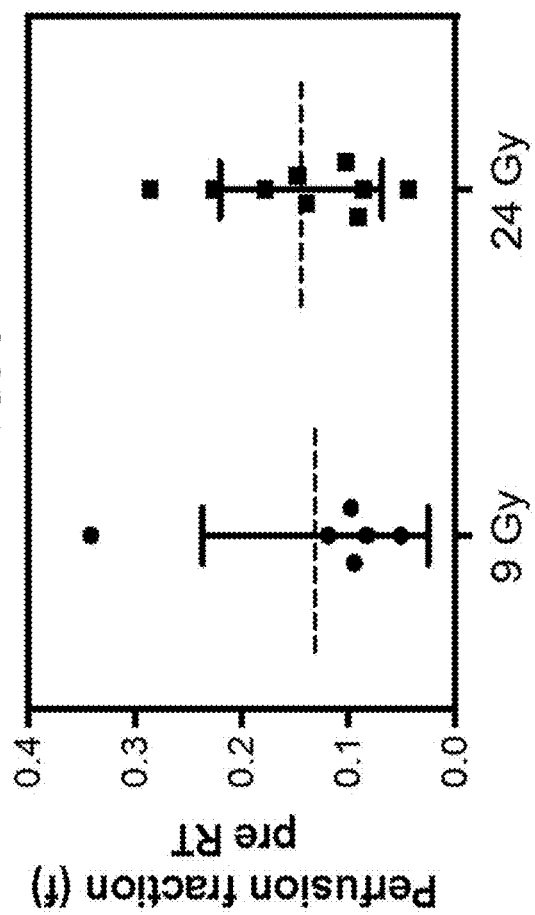
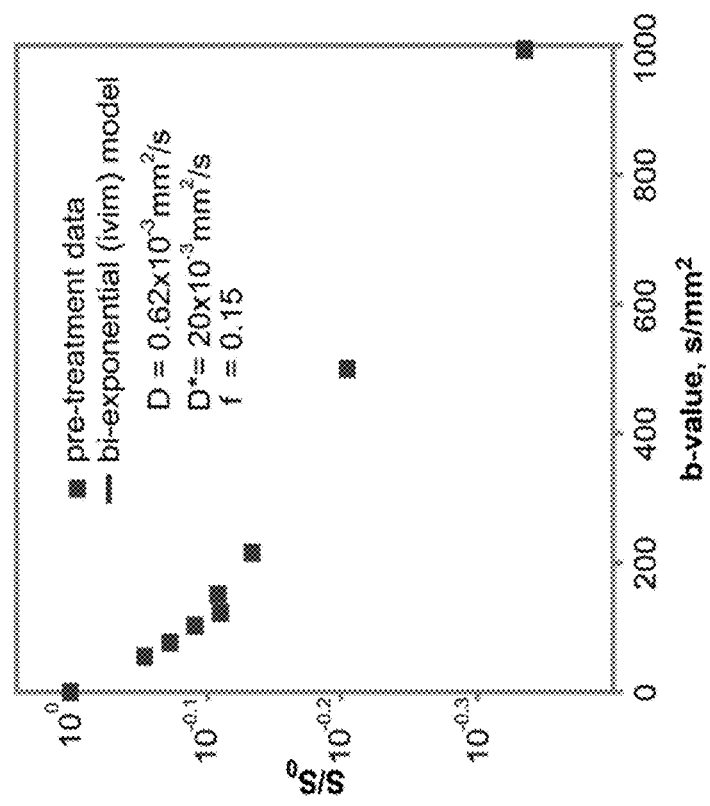
FIG. 9A
FIG. 9B

FIG. 10C

| | IVIM DW-MRI Study | | ASMase Study | |
|---|---|---|---|---|
| | 9 Gy (n=6) | 24 Gy (n=9) | 9 Gy (n=8) | 24 Gy (n=10) |
| Age | | | | |
| Median | 71 | 61 | 70 | 63 |
| Range | 53-73 | 44-72 | 49-74 | 44-76 |
| Gender | | | | |
| Male | 6 | 5 | 7 | 7 |
| Female | 0 | 4 | 1 | 3 |
| Histology | | | | |
| Prostate adenocarcinoma | 3 | 2 | 3 | 1 |
| Non-small cell carcinoma of the lung | 1 | | 1 | 2 |
| Colorectal adenocarcinoma | 1 | 1 | 1 | 1 |
| Renal cell carcinoma | | 1 | | 1 |
| Invasive ductal carcinoma of the breast | | 1 | | 1 |
| Follicular cell carcinoma of the thyroid | | 1 | 1 | 1 |
| Mucosal melanoma | 1 | | 1 | |
| Sinonasal squamous cell carcinoma | | | | 1 |
| Thymic carcinoma | | 1 | 1 | 1 |
| Leiomyosarcoma | | 2 | | 1 |

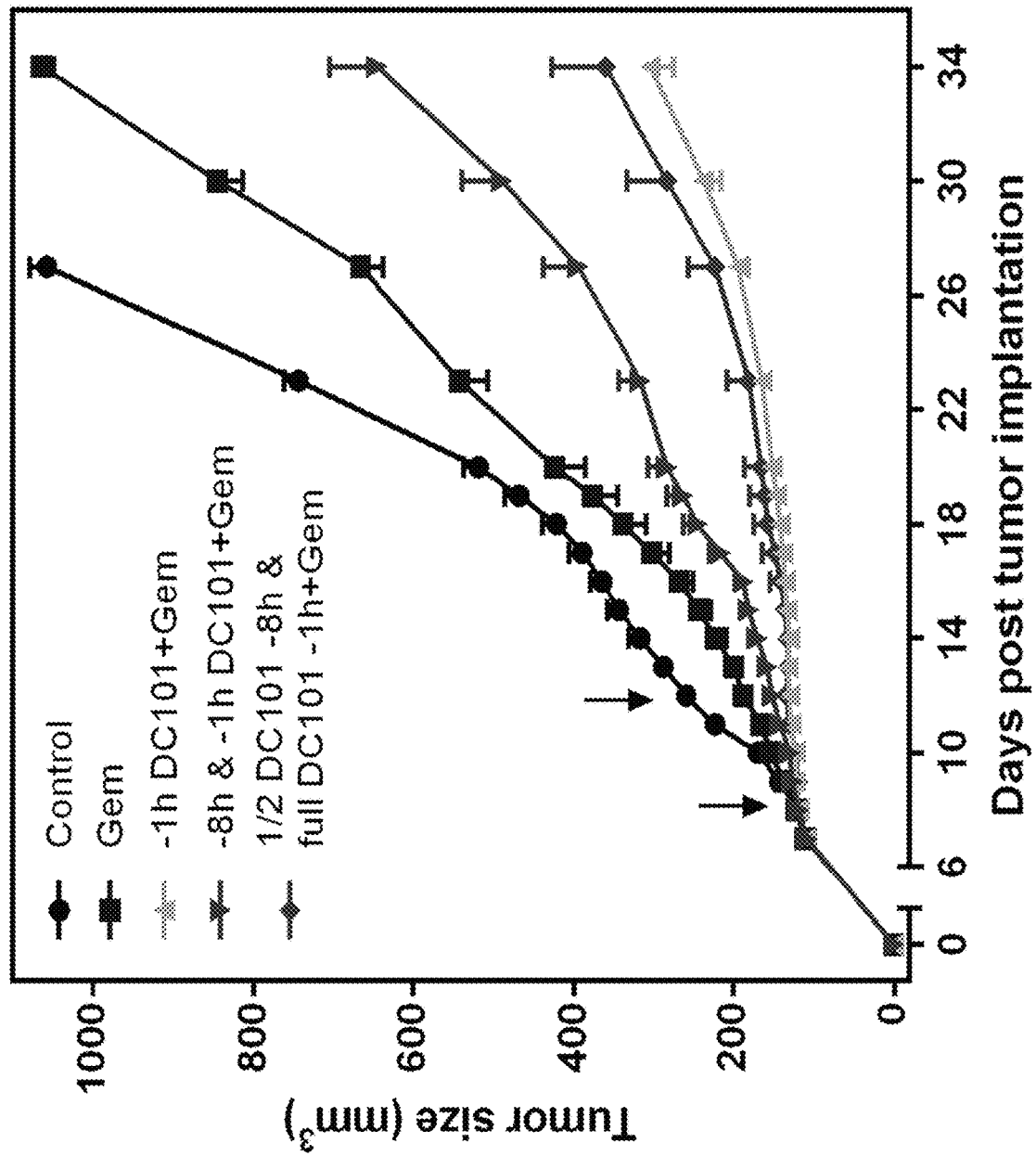

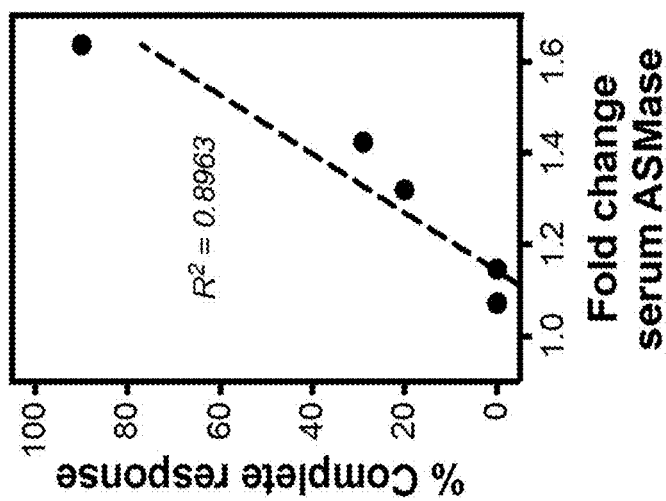
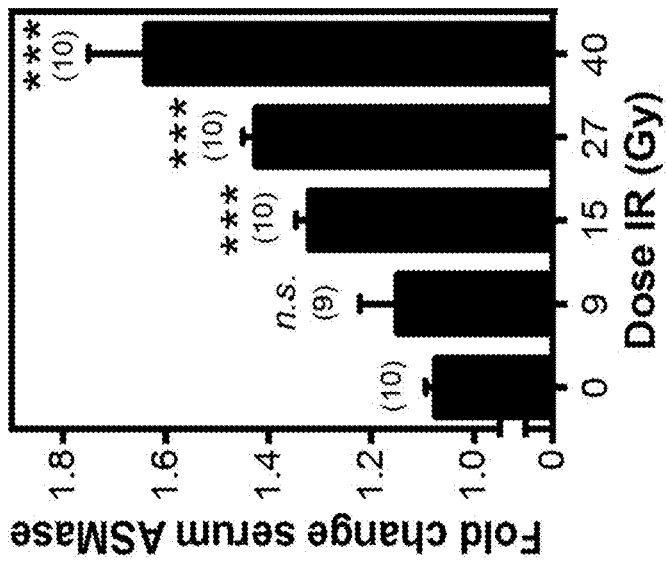
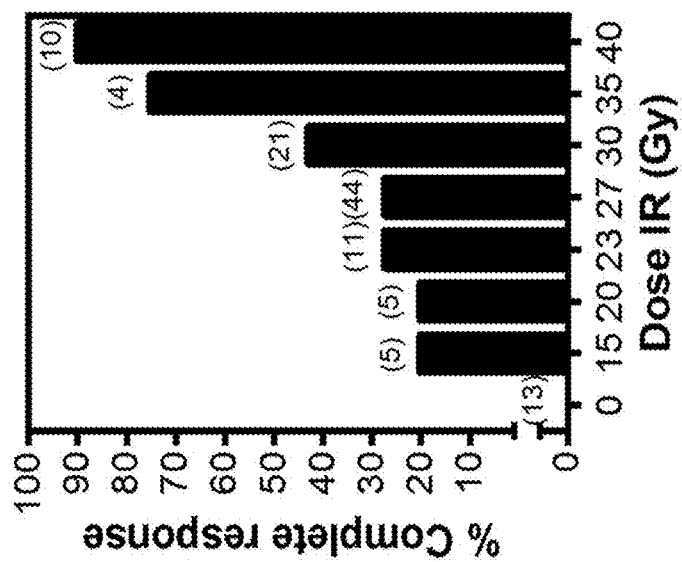

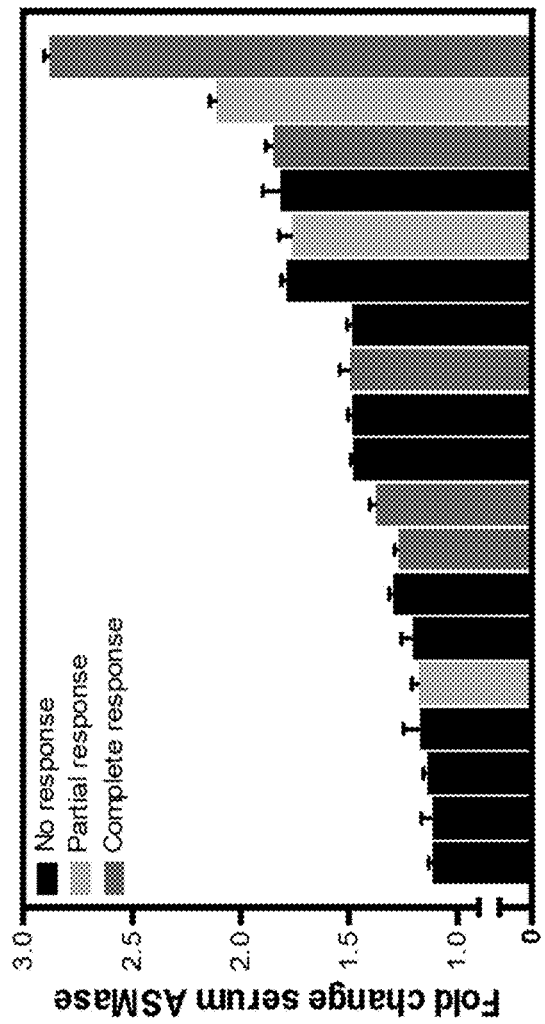
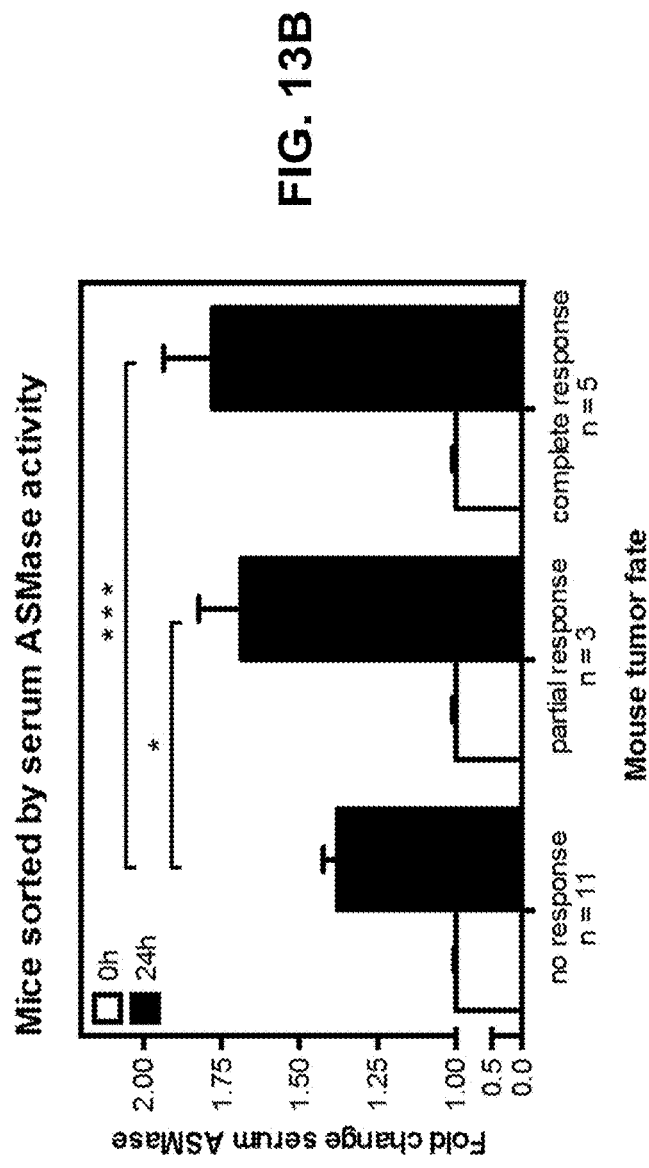
FIG. 13A
FIG. 13B

ENHANCEMENT OF TUMOR RESPONSE TO CHEMOTHERAPY BY ACTIVATION OF THE ASMASE/CERAMIDE PATHWAY THROUGH TIMED ADMINISTRATION OF A SHORT-ACTING ANTI-ANGIOGENIC AGENT

STATEMENT OR RELATED APPLICATIONS

This patent application is a continuation of U.S. patent application Ser. No. 15/525,856, filed May 10, 2017, which is a U.S. National Stage of PCT Application No. PCT/US2015/060486, filed Nov. 12, 2015, which claims the benefit of and priority to U.S. Provisional Patent Application No. 62/078,280, filed Nov. 11, 2014, the entire contents of each of which are incorporated herein by reference.

GOVERNMENT SUPPORT

This invention was made with government support under CA105125 and CA158367 awarded by the National Institutes of Health. The government has certain rights in the invention.

BACKGROUND OF THE DISCLOSURE

Technical Field

The present disclosure relates to the field of cancer therapy using anti-angiogenic agents, not as anticancer therapeutics per se, but as chemosensitization agents—to make patients more sensitive to chemotherapy, thereby increasing the effect of chemotherapeutic drugs. The present disclosure also relates to the development of biomarkers to monitor dosage, timing and effectiveness of such combined therapy.

Background and Description of Related Art

The main approaches to cancer treatment include radiation therapy, surgery, chemotherapy, immunotherapy and hormonal therapy. Chemotherapeutic agents can be grouped into several general classes based on their mechanism of action: taxanes, alkylating agents, antitumor antibiotics, topoisomerase inhibitors (e.g., topoisomerase II inhibitors), endoplasmic reticulum stress inducing agents, antimetabolites, and mitotic inhibitors.

While chemotherapeutic agents can be of substantial therapeutic benefit in many patients, their effectiveness is limited in many types of cancer. Moreover, chemotherapy resistance remains a major hindrance in cancer treatment. In order to improve clinical outcomes, a deeper understanding of the mechanisms that regulate chemotherapy sensitivity and resistance is necessary. Furthermore, the development of biomarkers that could be used to predict the efficacy of chemotherapy and to optimize dosage and administration regimens could contribute significantly to such improved outcomes.

Angiogenesis, a process whereby new blood vessels are formed from the pre-existing ones, is a hallmark of tumor development and metastasis. During tumorigenesis, as cancer cells rapidly proliferate, tumors expand beyond the support capacity of the existing vasculature, leading to hypoxia, depletion of nutrients and accumulation of metabolic wastes. Tumor cells in turn adapt to these conditions by upregulating pro-angiogenic factors, such as vascular endothelial growth factor (VEGF), basic fibroblast growth factor (bFGF), and platelet-derived endothelial growth factor (PDGF). These factors cause activation of endothelial cells, promoting the growth of new blood vessels. Since tumors require a vascular supply to grow, the inhibition of tumor growth by anti-angiogenic drugs has long been identified as an important target for research and approach to treatment and has spurred the development of several anti-angiogenic agents (AAA).

The first FDA-approved AAA, bevacizumab, is a monoclonal antibody that targets circulating VEGF A and has been approved for the treatment of numerous cancer types, including for example metastatic colorectal cancer, non-small cell lung cancer, kidney cancer and recurrent-progressive glioblastoma (as monotherapy) or for some of the same as well as additional cancers in combination with chemotherapeutic drugs.

Despite high early promise, the addition of anti-angiogenics to conventional chemotherapy drugs has had limited success. In fact, bevacizumab was originally approved for breast cancer but that approval was eventually withdrawn for lack of effectiveness. Thus, additional study of the detailed mechanism of anti-angiogenic response, and of the reasons for its failure, is needed in order to more effectively harness AAAs as a therapeutic modality. Additionally, development and validation are needed of biomarkers suitable for monitoring administration and effectiveness of AAAs as well as for determining improved dosage and administration regimen of the chemotherapy arm of combination therapies.

Rao, S. S. et al, *Radiotherapy and Oncology* 111 (2014) 88-93 (2014) (available online 29 Apr. 2014 incorporated by reference) reports that the short-acting AAA axitinib administered shortly before single dose radiation therapy (SDRT) increases acute tumor endothelial cell apoptosis and increases tumor response compared to SDRT administered alone. Rao specifically reports that the radiosensitization is dependent on the relative timing of administration of the two modalities with the optimum time being axitinib preceding SDRT by one hour in mice and producing no significant additive effect when this particular anti-angiogenic agent is administered 2 or more hours earlier than SDRT, or when administered at a point subsequent to SDRT. The authors draw parallels between previously reported anti-angiogenic de-repression of acid sphingomyelinase driven radiosensitization using anti-VEGF and anti-VEGFR2 antibodies and the radiosensitization observed by use of axitinib in combination with SDRT.

However, prior to the work described in this disclosure, the foregoing article had no implications for chemotherapy as the various chemotherapeutic agents have very different mechanisms of action as outlined above. Moreover, unlike the SDRT response which is known to be mediated in significant part by the endothelial cell ASMase/ceramide pathway, ceramide-mediated endothelial apoptosis has not been reported or proposed for chemotherapy. (Nor has acute ceramide-mediated vasoconstriction leading to ischemia reperfusion injury been previously proposed for RT or for chemotherapy.)

Dietrich, J et al, Expert Opin Investig Drugs. October 2009; 18(10): 1549-1557 doi: 10.1517/13543780903183528 review the use of cediranib, a short-acting anti-angiogenic agent in the treatment of glioblastoma. The authors generally rate the use of cediranib as promising for treatment of glioblastoma but note the absence of biomarkers for anti-angiogenic therapies. Further, the authors note the phenomenon of transient vascular normalization that follows treatment with anti-angiogenic agents and suggest that a specific treatment window might exist (related to vascular normalization) during which chemotherapy and radiation may be most effective. However, vascular normalization is a relatively slow-developing event, taking days to become manifest and thus this paper does not point to a second modality treatment window developing very close to AAA administration. Lastly, the authors comment that the reasons for re-establishment of pathologic vascularization (after the transient normalization stage) are poorly understood but if they can be elucidated may offer an explanation for failure of treatments with anti-angiogenic factors precipitated by up-regulation of alternate pro-angiogenic factors which are not targets of the administered anti-angiogenic agent.

As illustrated by the foregoing, anti-angiogenic drugs have not been successful and an acute need exists to find methods for increasing their contribution to clinical outcome. Moreover, a general need exists to improve clinical outcomes in cancer therapy in general.

SUMMARY OF THE DISCLOSURE

Disclosed is a method for enhancing the tumor response to chemotherapy comprising: (a) administering a short-acting anti-angiogenic agent (AAA) to a subject afflicted with a solid tumor, thereby creating a time interval of increased susceptibility of said tumor to at least one chemotherapeutic agent; (b) administering said at least one chemotherapeutic agent that has the property of activating the ASMase/ceramide signaling pathway to said subject at a time point within said interval; hereby enhancing the effect of the at least one chemotherapeutic agent against said tumor. Enhancement can be assessed by comparison to the chemotherapeutic agent being used (i) without the anti-angiogenic agent or (ii) at a time point outside the interval of increased susceptibility (chemosensitization interval).

In some embodiments the foregoing interval has been predetermined for a population of subjects or for a particular subject. In some embodiments, the interval has been determined by using IVIM DW-MRI, or by direct or indirect measurements of ASMase activity (for example by measurement of surrogates thereof) to determine an interval of acute increase following an administration of AAA, wherein the interval of acute ASMase activity increase is the interval of increased susceptibility of the subject to chemotherapy.

In some embodiments, the amount of the anti-angiogenic agent is effective to cause a substantial increase in ASMase activity in the subject during said interval. In some embodiments, ASMase activity is assessed by dynamic intravoxel incoherent motion (IVIM)-based diffusion-weighted magnetic resonance imaging (DW-MRI). In some embodiments, ASMase activity is assessed by measuring ASMase activity, or deducing ASMase activity by measuring a surrogate, such as one or more pro-apoptotic ceramides. Suitable pro-apoptotic ceramides include C16:0 ceramide and C18:0 ceramide.

In some embodiments, the amount of anti-angiogenic agent administered is one causing maximal ASMase activity increase provided that such amount does not exceed a maximum tolerated dose of the AAA.

In some embodiments, following a first administration of AAA and said at least one chemotherapeutic agent, the subject is administered a second dose of AAA after the lapse of a time interval at least sufficient for the AAA from the first administration to decay to an extent sufficient for the responsiveness to ASMase in said subject to a second administration of AAA to be reset (reestablishing ASMase sensitivity). The second administration of AAA is followed by a second administration of said at least one chemotherapeutic agent within an interval of increased susceptibility of said tumor created by the second administration of AAA. Any subsequent administration of AAA and chemotherapeutic will follow the method of the second administration.

In some embodiments, the tumor is selected from the group consisting of adrenal (e.g., adrenocortical carcinoma), anal, bile duct, bladder, bone (e.g., Ewing's sarcoma, osteosarcoma, malignant fibrous histiocytoma), brain/CNS (e.g., astrocytoma, glioma, glioblastoma, childhood tumors, such as atypical teratoid/rhabdoid tumor, germ cell tumor, embryonal tumor, ependymoma), breast (including without limitation ductal carcinoma in situ, carcinoma, cervical, colon/rectum, endometrial, esophageal, eye (e.g., melanoma, retinoblastoma), gallbladder, gastrointestinal, kidney (e.g., renal cell, Wilms' tumor), heart, head and neck, laryngeal and hypopharyngeal, liver, lung, oral (e.g., lip, mouth, salivary gland) mesothelioma, nasopharyngeal, neuroblastoma, ovarian, pancreatic, peritoneal, pituitary, prostate, retinoblastoma, rhabdomyosarcoma, salivary gland, sarcoma (e.g., Kaposi's sarcoma), skin (e.g., squamous cell carcinoma, basal cell carcinoma, melanoma), small intestine, stomach, soft tissue sarcoma (such as fibrosarcoma), rhabdomyosarcoma, testicular, thymus, thyroid, parathyroid, uterine (including without limitation endometrial, fallopian tube), and vaginal tumor and the metastasis thereof. In some embodiments, the tumor is selected from the group consisting of breast, lung, GI tract, skin, and soft tissue tumors. In some further embodiments the tumor is selected from the group consisting of breast, lung, GI tract and prostate tumors.

In some embodiments, the short-acting AAA is at least one AAA selected from the group consisting of cediranib, axitinib, anginex, sunitinib, sorafenib, pazopanib, vatalanib, cabozantinib, ponatinib, lenvatinib, and SU6668. In some embodiments the short-acting AAA has an average half-life of up to about 120 hours. Cetuximab is not considered short acting AAA.

In some embodiments, suitable classes of chemotherapeutic agents include, but not limited to taxanes, DNA alkylating agents, topoisomerase inhibitors, endoplasmic reticulum stress inducing agents, anti-tumor antibiotics, and antimetabolites.

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-8951f, MAG-CPT, amsacrine, etoposide, etoposide phosphate, teniposide, doxorubicin, paclitaxel, docetaxel, gemcitabine, baccatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephaolmannine, and mixtures thereof.

In some embodiments, the chemotherapeutic agent is selected from the group consisting of gemcitabine, paclitaxel, docetaxel, and etoposide, and mixtures thereof.

In some embodiments, the chemotherapeutic agent is a taxane.

In some embodiments the chemotherapeutic agent is selected from the group consisting of baccatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, and mixtures thereof.

In some embodiments the chemotherapeutic agent is a DNA alkylating agent. In further embodiments the chemotherapeutic agent is selected from the group consisting of nitrogen mustards, nitrosoureas, and alkylsulfonates.

In some embodiments the chemotherapeutic agent is selected from the group consisting of cyclophosphamide, chlorambucil, melphalan, bendamustine, uramustine, estramustine, carmustine, lomustine, nimustine, ranimustine, streptozotocin; busulfan, mannosulfan, and mixtures thereof.

In some embodiments the chemotherapeutic agent is a topoisomerase I inhibitor. In further embodiments the chemotherapeutic agent is selected from the group consisting of SN-38, ARC, NPC, camptothecin, topotecan, 9-nitrocamptothecin, exatecan, lurtotecan, lamellarin D9-aminocamptothecin, rubifen, gimatecan, diflomotecan, BN80927, DX-8951f, MAG-CPT, and mixtures thereof.

In some embodiments the chemotherapeutic agent is a topoisomerase II inhibitor. In further he chemotherapeutic agent is selected from the group consisting of amsacrine, etoposide, etoposide phosphate, teniposide, daunorubicin, mitoxantrone, amsacrine, ellipticines, aurintricarboxylic acid, doxorubicin, and HU-33 land combinations thereof.

In some embodiments the chemotherapeutic agent is an antimetabolite. In further embodiments the chemotherapeutic agent is selected from the group consisting of 5-fluorouracil (5-FU), 6-mercaptopurine (6-MP), capecitabine, cytarabine, floxuridine, fludarabine, gemcitabine, hydroxyurea, methotrexate, pemetrexed, and mixtures thereof.

In some embodiments the tumor is selected from the group consisting of adrenal, anal, bile duct, bladder, bone, brain/CNS, breast, cervical, colon/rectum, endometrial, esophageal, eye, gallbladder, gastrointestinal, kidney, heart, head and neck, laryngeal and hypopharyngeal, liver, lung, oral mesothelioma, nasopharyngeal, neuroblastoma, ovarian, pancreatic, peritoneal, pituitary, prostate, retinoblastoma, rhabdomyosarcoma, salivary gland, sarcoma, skin, small intestine, stomach, soft tissue sarcoma, rhabdomyosarcoma, testicular, thymus, thyroid, parathyroid, uterine, and vaginal tumors and metastases thereof. In further embodiments the tumor is selected from the group consisting of breast, lung, GI tract and prostate tumors.

In some embodiments the AAA has a half-life of less than about 120 hours, less than about 110 hours, less than about 100 hours, less than about 90 hours, less than about 80 hours, less than about 70 hours, less than about 60 hours, less than about 50 hours, less than about 40 hours, less than about 35 hours, less than about 30 hours, less than about 25 hours, less than about 20 hours, less than about 18 hours, less than about 15 hours, less than about 12 hours, less than about 10 hours, or less than about 8 hours. In some embodiments the AAA has a decay period that is about the same as the half-life of the AAA.

In some embodiments the AAA is administered at the maximum tolerated dose of the AAA, about 90% of the tolerated dose of the AAA, about 80% of the tolerated dose of the AAA, about 70% of the tolerated dose of the AAA, about 60% of the tolerated dose of the AAA, about 50% of the tolerated dose of the AAA, about 40% of the tolerated dose of the AAA, about 30% of the tolerated dose of the AAA, about 20% of the tolerated dose of the AAA, or about 10% of the tolerated dose of the AAA.

In some embodiments the AAA is administered at the approved dose for daily administration, about twice the approved dose for daily administration, about three times the approved dose for daily administration, about four times the approved dose for daily administration, about five times the approved dose for daily administration, about six times the approved dose for daily administration, about seven times the approved dose for daily administration, about eight times the approved dose for daily administration, about nine times the approved dose for daily administration, or about ten times the approved dose for daily administration.

In some embodiments the chemotherapeutic agent is administered about 0.5 to 5 hours, about 0.5 to 4 hours, about 0.5 to 3 hours, about 0.5 to 2 hours, about 0.5 to 1.5 hours, about 0.5 to 1 hour, 1 to 5 hours, about 1 to 4 hours, about 1 to 3 hours, about 1 to 2 hours, about 1 to 1.5 hour, 1.5 to 5 hours, about 1.5 to 4 hours, about 1.5 to 3 hours, about 1.5 to 2 hours, 2 to 5 hours, about 2 to 4 hours, about 2 to 3 hours, about 3 to 5 hours, about 3 to 4 hours, or about 4 to 5 hours after administration of the AAA.

In further embodiments the chemotherapeutic agent is administered no more than about 2 hours or no more than about 1.5 hours or no more than about 1 hour after administration of the AAA or the administration of the chemotherapeutic agent is commenced within a half-hour after administration of the AAA.

Disclosed is also a method for predicting tumor response or monitoring efficacy or timing of treatment of a patient to a chemotherapeutic agent, the patient being afflicted with a malignant solid tumor, the method comprising: using diffusion-weighted magnetic resonance imaging (DW-MRI) and in more particular embodiments dynamic intravoxel incoherent motion (IVIM)-based diffusion-weighted magnetic resonance imaging (DW-MRI) shortly following administration of the chemotherapeutic agent to determine the extent of rapid perfusion alterations in the tumor vasculature following administration of the chemotherapeutic agent, wherein an increased amount of alterations over baseline is indicative of tumor response to said chemotherapeutic agent or of appropriate timing and/or efficacy of treatment.

Other aspects of the present disclosure are directed to:
a. Methods for predicting tumor response or monitoring timing and/or efficacy of treatment in a patient afflicted with a malignant tumor to a chemotherapeutic agent, comprising:
  measuring an ASMase level or activity in the patient following administration of the chemotherapeutic agent to the patient wherein an increase in said level or activity compared to baseline is indicative of tumor response to the chemotherapeutic agent or confirms the efficacy and/or appropriate timing of treatment (and wherein, conversely, an absence of such decrease carries no such prediction); and
b. Methods for predicting tumor response or monitoring timing of treatment in a patient to a chemotherapeutic agent, the patient being afflicted with a malignant solid tumor, the method comprising:
  using diffusion-weighted magnetic resonance imaging (DW-MRI) and preferably dynamic intravoxel incoherent motion (IVIM)-based DW-MRI to measure perfusion alterations following administration of the chemotherapeutic agent to determine the extent of rapid perfusion defects in the tumor vasculature following administration of the chemotherapeutic agent, wherein an increased level of said alterations over baseline is indicative of tumor response to said chemotherapeutic agent or of efficacy or appropriate timing of treatment (and wherein, conversely, an absence of such perfusion alterations carries no such indication).

BRIEF DESCRIPTION OF THE FIGURES

FIGS. 1A and 1B are plots, respectively of ASMase activity (nmols/mg/hr) and ceramide levels (pmols/$10^6$ cells) in BAEC against time after treatment of endothelial cells with a chemotherapeutic agent, paclitaxel (100 nM).

FIGS. 1D and 1E are plots, respectively of ASMase activity (nmols/mg/hr) and ceramide levels (pmols/$10^6$ cells) in BAEC, against time after treatment of bovine endothelial cells with the chemotherapeutic agent etoposide (50 FIG. 1F is a bar graph showing ceramide levels (pmols/$10^6$ cells) over time (min) in HCAEC treated with 50 μM etoposide.

FIGS. 2A and 2B are plots of incidence of apoptosis (% apoptosis) against time (hrs) in BAEC treated with paclitaxel (100 nM) (FIG. 2A) or etoposide (50 μM) (FIG. 2B). FIG. 2C is a bar graph showing incidence of apoptosis (% apoptosis) at increasing doses of cisplatin in BAEC.

FIG. 3 is a bar graph showing incidence of apoptosis (% apoptosis) in BAEC pre-incubated with bFGF (2 ng/mL), VEGF (2 ng/mL) or nystatin (30 μg/mL) prior to treatment with etoposide (50% apoptosis was determined was evaluated after 8 hours of etoposide treatment.

FIG. 5A shows tumor volume over time in SCID$^{asmase+/+}$ or SCID$^{asmase-/-}$ mice harboring HCT116 tumors (50-70 mm$^3$) and treated with paclitaxel (15/20/25 mg/kg i.p.) three times biweekly. Arrows indicate days of paclitaxel treatment. Data (mean±SD) are collated from 5 mice per group. FIG. 5B shows tumor volume over time in SCID$^{asmase+/+}$ mice harboring HCT116 tumors (50-70 mm$^3$) and treated with etoposide (35/35/50 mg/kg i.p.) biweekly in the presence of anti-ceramide or isotype control antibody. Arrows indicate days of etoposide treatment. Data (mean±SD) are collated from 5 mice per group.

FIG. 6A shows anti-angiogenic chemosensitization of HCT116 tumors in SCID$^{asmase+/+}$ mice treated with DC101 (1.6 mg per mouse i.v.) 1 hour prior to paclitaxel treatment. FIGS. 6B and 6C show effect of timing of DC101 relative to paclitaxel on the response of HCT116 tumors. DC101 (800 μg/25 gm mouse i.v.) was provided either before (FIGS. 6B and 6C) or after (FIG. 6C) paclitaxel treatment.

FIGS. 7E and 7F are the same types of plots as 7C and 7D for the same patients after two cycles of treatment with bevacizumab and gemcitabine administered as for FIGS. 7C and 7D.

FIG. 9 are plots that demonstrate SDRT induced microvascular changes in patients. FIG. 9A shows two values obtained by IVIM DW-MRI representing the fraction of moving blood (f) and the velocity of blood (D*) in the microcirculation. Shown is a schematic representation of the calculation of f and D* from the biexponential decay diffusion curve. FIGS. 9B and 9D are dot plots showing a baseline, pre-SDRT D* and f values for all patients in each patient cohort.

FIG. 10 shows that serum ASMase activity changes in patients receiving SDRT in a dose dependent manner. FIG. 10C shows age, gender and tumor type for patients in each cohort.

FIG. 11A is a plot of MCA/129 fibrosarcoma tumor volume versus days post tumor implantation showing that long acting anti-angiogenic drugs (such as DC101) render tumors refractory to subsequent anti-angiogenic ASMase-mediated chemotherapy chemosensitization. Data (mean±SEM) were collated from 5 mice/group.

FIG. 12C is a bar graph depicting a relationship between radiation dose and ASMase activity changes 24 hours following IR. FIG. 12D shows a correlation between change in ASMase activity 24 hours post-IR, and tumor control. Number of mice is indicated in parentheses in 12B and 12C. *P<0.05, P<0.01, *P<0.001. Two tailed, unpaired, student's t test was used in 12C. Pearson's Correlation Coefficient was used in 12D.

FIG. 13 indicates that changes in ASMase activity predict tumor responses to SDRT. FIG. 13A shows changes in ASMase activity 24 hours post-IR (27 Gy in each mouse (total of 19 animals), ranked by induced activity. Means (±SE) of 3 serum measurements are displayed. FIG. 13B is a bar graph indicating a relationship between induced ASMase activity and ultimate tumor responses. Two tailed, unpaired t tests were used in FIG. 13B. *P<0.05, P<0.01, *P<0.001.

FIG. 14A is a graph of vascularity (Fp) over time in fibrosarcoma tumors.

DETAILED DESCRIPTION

The present disclosure is based on the following discoveries:

The ASMase/ceramide pathway is activated in endothelial cells by chemotherapeutic agents that belong to distinct classes of chemotherapeutic agents, such as: taxanes, topoisomerase inhibitors, and nucleoside analog metabolic inhibitors. Paclitaxel, etoposide and gemcitabine were shown to activate ASMase signaling and generation of ceramide in cultured bovine aortic endothelial cells (BAEC) and human coronary artery endothelial cells (HCAEC). Activation of ASMase/ceramide pathway leads to the formation of ceramide-rich microdomains (CRMs). Cisplatin failed to elicit apoptosis in BAEC but it is known to induce apoptosis and to increase ASMase in human cells (Lacour et al. *Cancer Res.* 15; 64(10):3593-8 (2004); Maurmann et al. *Apoptosis,* 20:7, 960-974 (2015). Based on this, cisplatin therapy is also expected to take advantage of chemosensitization according to the present disclosure.

Figure 14B:
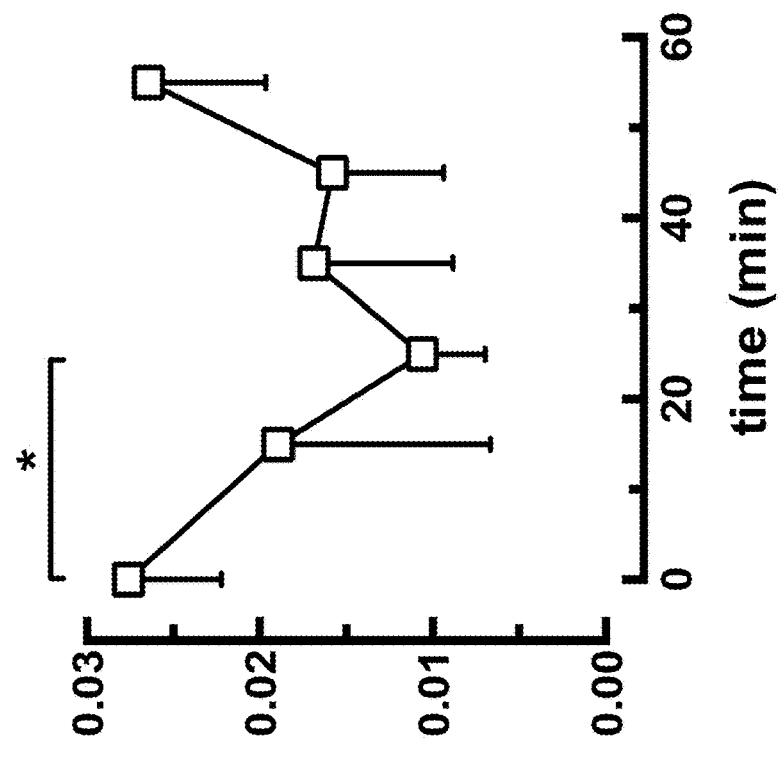
FIG. 14B is a graph of diffusion over time in fibrosarcoma tumors.
Figure 14A:
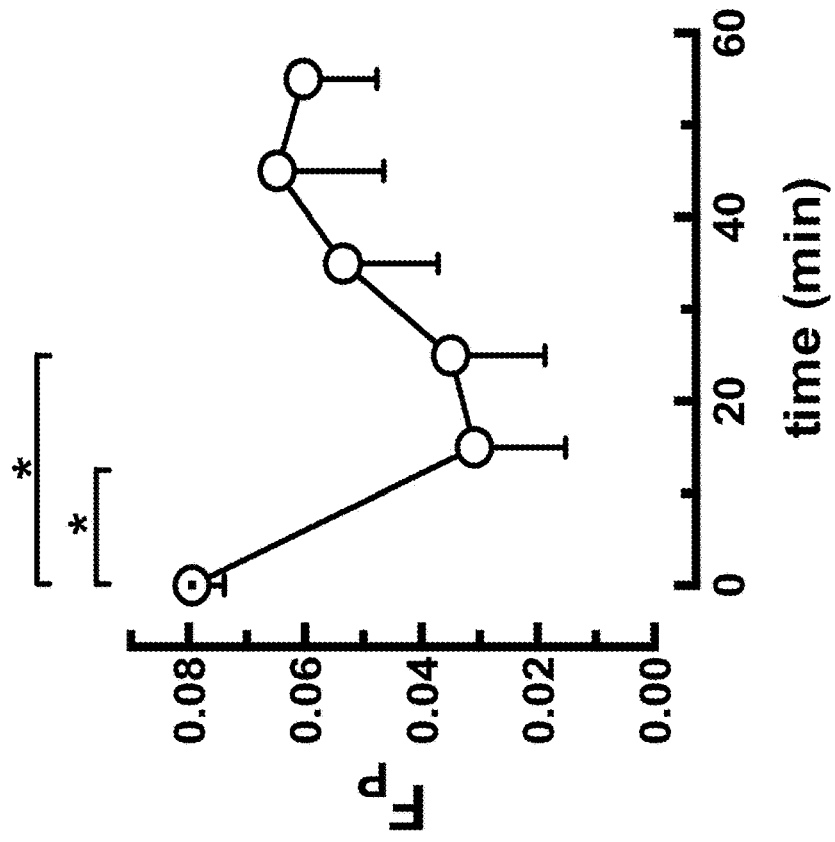
FIG. 14A shows that gemcitabine rapidly reduces vascular perfusion in fibrosarcoma tumors and that gemcitabine activates ASMase in a dose dependent manner.
Figure 14D:
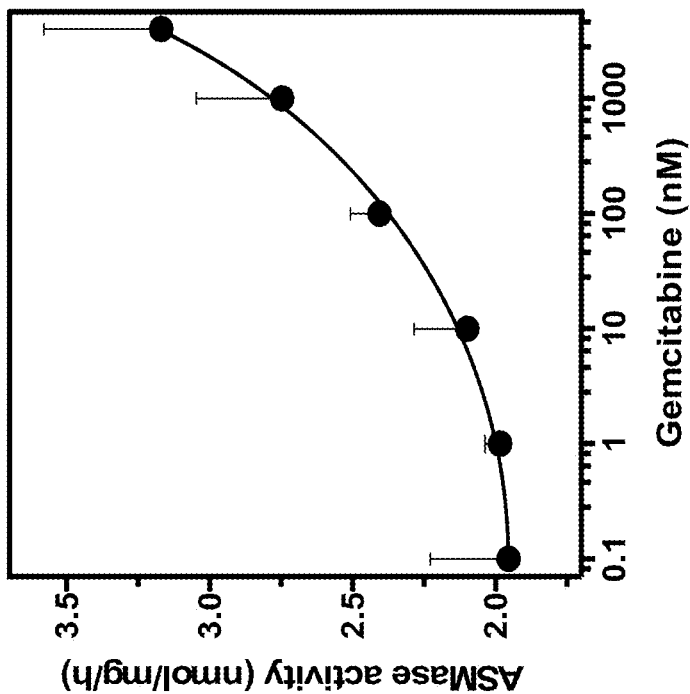
FIG. 14D is a graph of ASMase activity following the treatment of bovine aortic endothelial cells with increasing doses of gemcitabine (measurements taken at 5 minutes following the treatment).

1. Paclitaxel, etoposide and gemcitabine also trigger endothelial dysfunction, as evident by endothelial apoptosis both in vitro and in vivo. Cisplatin also induces apoptosis in human endothelial cells.
2. Endothelial apoptosis is inhibited by pre-incubation of cells with pro-angiogenic factors that prevent ASMase activation and ceramide generation, such as VEGF, bFGF, and nystatin.
3. ASMase signaling is required for chemotherapy-induced apoptotic response in vivo. Furthermore, the t ASMase/ceramide pathway mediates tumor growth delay caused by chemotherapy agents that have the ability to activate ASMase/ceramide signaling.
4. Human HCT-116 colon cancer and MCA/129 murine sarcoma xenografts implanted in wild-type asmase$^{+/+}$ mice undergo endothelial, but not tumor cell, apoptosis following the treatment with chemotherapeutic agent paclitaxel or etoposide. Additionally, chemotherapy treatment results in significant tumor growth delay in wild-type asmase$^{+/+}$ mice. The opposite is observed when xenografts are implanted in asmase$^{-/-}$ mice. Tumors generated in mice deficient in ASMase signaling show lack of endothelial cell apoptosis and no significant tumor response when treated with paclitaxel or etoposide. Finally, intravenous injection of anti-ceramide IgM 1 hour prior to administration of chemotherapeutic agents abrogates or attenuates the benefits of chemotherapy on tumor growth in these models. Collectively, these results indicate that ASMase signaling and ceramide formation are required for chemotherapy-induced endothelial cell apoptosis and optimal tumor response.
5. Anti-VEGFR2 antibody DC101, which de-represses endothelial ASMase inhibited by VEGF, shows a synergistic tumor response when used in combination with paclitaxel or gemcitabine in HCT116 tumors and MCA/129 fibrosarcomas, but only when administered 1-2 hours prior to, and not immediately preceding, chemotherapy treatment. However, the synergistic effect of anti-angiogenic agent and chemotherapy is completely abolished when HCT-116 and MCA/129 xenografts were implanted in host asmase$^{-/-}$ mice that provide injury-resistant microvasculature to tumors. Together, these observations indicate the existence of a previously unreported chemotherapy-induced tumor microvascular response mechanism that acts synergistically with chemotherapeutic impact on tumor cells and that is required for optimal tumor response.
6. Anti-angiogenic chemosensitization is contingent on precise timing of anti-angiogenic delivery, and activity of the ASMase/ceramide pathway. Chemosensitization occurs only if anti-angiogenic agent was delivered within the acutely increased ASMase activity window (chemosensitization window) following administration of AAA. In the systems of experiments described here, this window was observed to have a duration of 1-2 hours preceding chemotherapy, but at no other time preceding or after chemotherapy. Thus, there is a chemosensitization interval or window following the administration of anti-angiogenic agent during which treatment with chemotherapy should occur.
7. Synchronized timing of AAA with chemotherapy, where AAA is delivered prior to the administration of chemotherapy such that chemotherapy is administered (or at least its administration is commenced) within the chemosensitization window, significantly improves tumor response to chemotherapy. Overall, clinical outcome in the studies presented here represents proof-of-principle that ASMase signaling can be engaged for therapeutic benefit. These results also support that ASMase signaling can be established as a biomarker for predicting tumor response and in any event for adjusting timing and dosage of the AAA, optimum timing of the chemotherapeutic drug (relative to the AAA administration) and dosage of the chemotherapeutic drug.
8. Long-acting anti-angiogenic agents (drugs) render tumors refractory to subsequent anti-angiogenic ASMase-mediated tumor chemosensitization, where the strength of inhibition intensifies as the amount of long-acting anti-angiogenic agent present in the subject increases. Thus, these experiments support the proposition that short-acting anti-angiogenic drugs are preferred for ASMase/ceramide pathway-based chemosensitization compared to long-acting anti-angiogenics such as bevacizumab or DC101.
9. Phase II human clinical trial data show that bevacizumab delivery (on day zero of a three-week cycle) 1 hour before the administration of chemotherapy agent gemcitabine in patients treated for metastatic sarcoma, followed by administration of docetaxel on day 8 significantly improves tumor response.
10. Single dose radiotherapy (SDRT) induces microvascular vasoconstriction in MCA/129 murine sarcomas and B16 melanomas implanted in asmase$^{+/+}$ mice following 20 Gy SDRT. On the contrary, MCA/129 murine sarcomas and B16 melanomas implanted in asmase null animals do not exhibit perfusion dysfunction following the same exact treatment. These findings suggest a causal relationship between ASMase activity and vascular dysfunction.
11. A clinical study including 15 patients with bone metastases showed that SDRT induces perfusion reduction or ischemia reperfusion injury (attributed to microvascular vasoconstriction) following 24 Gy SDRT. These results suggest that perfusion alterations can be used as a biomarker indicative of effective treatment. Furthermore, development of such perfusion alterations as a biomarker can be used to dose de-escalate SDRT.
12. ASMase activity follows the same trend as perfusion alterations due to microvascular vasoconstriction in patients treated with 24 Gy. ASMase levels in the serum of 18 patients increased following the 24 Gy SDRT, suggesting that ASMase activity can serve as a serum biomarker of clinical success. These results are consistent with the findings in pre-clinical animal models, which revealed that perfusion alterations are dependent on ASMase activity. It is anticipated that a similar microvascular vasoconstriction manifest as perfusion alterations (likely developing at a somewhat slower pace) will be observed if chemotherapy, rather than radiation, is used as a second therapeutic modality.
13. The intensity of ASMase serum activity increase correlates directly with dose-dependent probability of complete response after SDRT of MCA/129 fibrosarcoma. These findings indicate that ASMase levels and/or activity may serve as a serum biomarker in human cancer management.
14. Microvascular vasoconstriction occurs immediately following administration of a chemotherapeutic agent activating ASMase signaling in animal model of fibrosarcoma, and Gemcitabine activates ASMase in a dose-dependent manner. It is anticipated that other ASMase activating chemotherapeutics will perform qualitatively the same.
15. Ionizing radiation results in translocation of ASMase to the plasma membrane, generating ceramide and ceramide-rich platforms. VEGF inhibits ASMase activation through VEGFR2 receptor signaling whereas anti-angiogenics can de-repress ASMase activation if given 1-2 hours prior to radiation. Secretion of ASMase into the blood may serve as a biomarker of upstream ASMase activation. Ceramide-rich platforms lead to downstream endothelial cell dysfunction, including decreased tumor microvascular perfusion which can be observed with IVIM DW-MRI and likely other imaging modalities.
16. As shown here, an increase in SDRT dose was directly proportional to the observed increase in serum ASMase activity, which in turn directly correlated with percent SDRT-induced complete tumor response (FIG. 12). Similarly, an increase in gemcitabine dose proportionally increased ASMase activity (FIG. 14D). These observations indicate that therapeutic targeting of factors known to inhibit ASMase, such as angiogenic growth factors (for example VEGF signaling) would lead to an increase in ASMase activity, which in turn results in enhanced responses to SDRT or chemotherapy. Thus, use of anti-angiogenic agents followed by SDRT or chemotherapy delivered within the time window of acute ASMase activation will increase tumor response proportional to the intensity of ASMase activation. Hence, it would be desirable to use the highest dosage of anti-angiogenic agent feasible and safe, to maximize ASMase activation and the consequently increased SDRT or chemotherapy response if delivered within the restricted ASMase-activation time window. Whereas SDRT and chemotherapy are often administered at or near their maximum tolerated dose to maximize the anti-tumor effect, tumor response radiation or chemosensitization by maximal anti-angiogenic dosage is expected to increase the beneficial effect of the combined therapy disclosed herein and may even enable de-escalation of the radiation or chemotherapy dose, titrated to the radiation or anti-cancer drug dose required to achieve local and/or systemic tumor cure when used in properly timed combination with anti-angiogenic therapy.

Based on the foregoing, the present inventors have devised treatment modifications to take advantage of these observations and developed biomarkers for assessing and predicting treatment outcome and monitoring treatment efficacy and relative timing of administration of anti-angiogenic agents and chemotherapeutic drugs.

Definitions

As used herein, the following terms and abbreviations shall have the meaning ascribed to them below unless the context clearly indicates otherwise.

"AAA" means and is used interchangeably with "anti-angiogenic agent."

"CRM" means "ceramide-rich macrodomain."

"Decay" in connection with an administered AAA means the inactivation, binding or clearance of such agent in or from the body of a patient such that the agent can no longer exert substantial activity.

"Subject" means a patient (human or veterinary) or an experimental animal, such as a mouse or other rodent.

"Synergistic effect," "synergy," or "synergistic tumor response" means the effect of two or more active agents administered as described herein is greater than the sum of the effects each agent would produce had the agent been administered alone. With specific reference to timing, a "synergistic effect" is a therapeutic effect of two or more active agents wherein a second-administered agent is administered (or its administration is at least commenced) within a chemosensitization interval created by administration of the first such that the effect of the appropriately timed administration is greater than the effect of an inappropriately timed administration wherein the second administered therapeutic agent is administered outside the chemosensitization window created by the first agent.

"Time interval of increased susceptibility" or "chemosensitization interval" refers to the period of time after administration of the AAA wherein the tumor response to chemotherapy is increased or wherein ASMase activity/ceramide signaling is acutely increased.

"Substantial" with particular reference to an increase in ASMase activity, perfusion alteration, increase in ceramide level or other measured or derived parameter will mean an increase or other change that is rapid and clearly observable. For example a change reaching statistical significance would be considered substantial. A statistically significant ASMase activity increase in response to a chemotherapeutic agent can be qualitatively similar to that of FIG. 14C. Furthermore, ceramide levels (C16:0, C18:0) undergoing a statistically significant increase following chemotherapy would increase in a manner qualitatively similar to that of FIG. 8.

"Restoration of biologic output" of ASMase or ceramide or any other measured parameter refers to a reestablishment of the ability in the endothelium of the host to undergo an increase in ASMase (or other parameter) activity or expression upon a second administration of AAA after decay of a first administration of AAA.

Short-Term Acting Anti-Angiogenic Agents (AAA)

Anti-angiogenic agents (AAA) suitable for use in the present method are short-acting AAAs with shorter average decay periods as compared to long-acting AAAs such as bevacizumab, which has an active half-life in the body of a patient of approximately three weeks, and DC101. As used herein, a decayed anti-angiogenic agent shall no longer be available at levels sufficient to cause ASMase in the patient to become substantially refractory (and consequently not substantially increase in response) to a subsequent AAA treatment. In other words, the decay of the AAA should be sufficient to reset ASMase sensitivity to a new administration of AAA. The decay period of an AAA is assessed by measuring one or more of serum levels of said agent, restoration of biologic output of ASMase, restoration of biologic output of ceramide or perfusion alteration.

Short-acting AAAs suitable for use in the present invention have considerably shorter average decay periods measured in hours (up to about 120 hours). Suitable AAAs include, but are not limited to: cediranib (average plasma half life of about 22 to 27 hours and a peak plasma concentration of 2-8 hours after administration), axitinib (average half-life 2.5 to 6 h), anginex (half-life ~50 minutes), sunitinib (average half-life of 40-60 hours), sorafenib (average half-life of about 25-48 hours), pazopanib (average half-life of about 30 hours), vatalanib (average half-life of 4.7 hours), cabozantinib (average half-life of 55 hours), ponatinib (average half-life of 24 hours); lenvatinib (average half-life of 28 hours) and SU6668 (average half-life of 3.6 hours). Half-life is an indicator of decay period although decay (such that a residual amount remaining from a first administration will not be enough to foreclose ASMase activation upon a subsequent administration of AAA) is also dependent on the dose administered.

In certain embodiments of the invention, the AAA has a decay period of less than about 120 hours, less than about 110 hours, less than about 100 hours, less than about 90 hours, less than about 80 hours, less than about 70 hours, less than about 60 hours, less than about 50 hours, less than about 40 hours, less than about 35 hours, less than about 30 hours, less than about 25 hours, less than about 20 hours, less than about 18 hours, less than about 15 hours, less than about 12 hours, less than about 10 hours, or less than about 8 hours.

In further embodiments of the invention, the AAA has a decay period from about 1 to 3 hours, from about 1 to 5 hours, from about 1 to 7 hours, from about 1 to 10 hours, from about 1 to 15 hours, from about 1 to 20 hours from about 1 to 25 hours, from about 1 to 30 hours, from about 1 to 40 hours, from about 1 to 50 hours, from about 1 to 60 hours from about 1 to 70 hours, from about 1 to 80 hours, from about 1 to 90 hours, from about 1 to 100 hours, from about 2 to 3 hours, from about 2 to 5 hours, from about 2 to 7 hours, from about 2 to 10 hours, from about 2 to 15 hours, from about 2 to 20 hours from about 2 to 25 hours, from about 3 to 5 hours, from about 3 to 7 hours, from about 3 to 10 hours, from about 3 to 15 hours, from about 3 to 20 hours from about 3 to 25 hours, from about 3 to 30 hours, from about 5 to 7 hours, from about 5 to 10 hours, from about 5 to 12 hours, from about 5 to 15 hours, from about 5 to 20 hours from about 5 to 25 hours, from about 5 to 30 hours, about 5 to 40 hours, from about 5 to 50 hours, from about 5 to 60 hours from about 5 to 70 hours, from about 5 to 80 hours, from about 5 to 90 hours, from about 5 to 100 hours, from about 7 to 10 hours, from about 7 to 12 hours, from about 7 to 15 hours, from about 7 to 20 hours from about 7 to 25 hours, from about 7 to 30 hours, from about 7 to 35 hours, from about 7 to 40 hours, from about 10 to 12 hours, from about 10 to 15 hours, from about 10 to 20 hours, from about 10 to 25 hours, from about 10 to 30 hours, about 10 to 40 hours, from about 10 to 50 hours, from about 10 to 60 hours from about 10 to 70 hours, from about 10 to 80 hours, from about 10 to 90 hours, from about 10 to 100 hours, from about 20 to 25 hours, from about 20 to 30 hours, about 20 to 40 hours, from about 20 to 50 hours, from about 20 to 60 hours from about 20 to 70 hours, from about 20 to 80 hours, from about 20 to 90 hours, or from about 20 to 100 hours.

It is an important aspect of the present disclosure that short-acting AAA's will be advantageous for use in the timed combination of AAA administration and chemotherapy such that the AAA sensitizes the patient to chemotherapy and wears off before a subsequent dose of AAA is given. If the prior dose has not worn off, as can be the case with, e.g., bevacizumab or DC101, the ASMase signaling of the patient becomes refractory and no longer responds to a fresh dose of AAA.

Another important aspect of this disclosure is that, based on the showing by the inventors that ASMase activation correlates with survival of subjects including human patients, the optimum amount of short-acting AAA administered is anticipated to be several times higher than the currently approved dose designed for daily administration and may be as high as the maximum tolerated dose of AAA. This amount is of course subject to optimization, which can be achieved using the teachings provided herein to achieve maximal ASMase activation (subject to any dose-limiting toxicity).

Chemotherapeutic Agents

Chemotherapeutic agents suitable for use in the methods and uses described below include agents that have the property of activating ASMase/ceramide signaling in a patient (for example, in endothelial cells). As is shown below, representatives of several but not all classes of chemotherapeutic agents have this property. In any event, a procedure for ascertaining this property is described herein. See, for example below, Materials and Methods and Example 1.

In certain embodiments, suitable chemotherapeutic agents include, but are not limited to taxanes, topoisomerase inhibitors and antimetabolites (e.g., nucleoside analogs acting as such, for example, gemcitabine). Other classes of chemotherapeutics may be included contingent on their possessing the property of activating ASMase. Nonlimiting examples to be considered include alkylating agents, antimetabolites, anti-tumor antibiotics, mitotic inhibitors, and other chemotherapeutic agents capable of activating ASMase/ceramide signaling pathway.

In certain embodiments, suitable chemotherapeutic agents exclude platinum containing chemotherapeutics. In further embodiments of the invention, suitable chemotherapeutic agents exclude cisplatin.

In still further embodiments, more than one chemotherapeutic agent may be administered. In certain embodiments, a first chemotherapeutic agent may be administered within the chemosensitization interval of the AAA and a second chemotherapeutic agent may be administered after this window. In other embodiments, more than one chemotherapeutic agent may be administered within the chemosensitization interval of the AAA. For example, in Example 21, both gemcitabine and docetaxel would be administered although only one, gemcitabine, is administered during the increased ASMase activity or signaling interval or window. However, if co-administration or immediately sequential administration of a second chemotherapeutic is indicated, such administration may be advantageously effected during the increased ASMase signaling interval. Alternatively, if the process is repeated such that administration of AAA is repeated after substantial decay of the AAA in the subject's body (and the sensitivity to AAA-induced acute ASMase activation is reset). The second (and any subsequent) AAA administration creates a new increased ASMase window. The chemotherapeutic can then be administered during that window of chemosensitization and if a second chemotherapeutic agent is indicated, it can be administered substantially simultaneously within the same window of chemosensitization or in alternating cycles within successive windows of chemosensitization), with administration of a chemotherapeutic agent always following closely administration of AAA so as to be within the window.

Thus, based on the findings of the present disclosure, many chemotherapeutic agents and their derivatives and/or functional analogues are expected to possess ASMase activating property, including, but not limited to taxanes, DNA alkylating agents, topoisomerase inhibitors, endoplasmic reticulum stress inducing agents, anti-tumor antibiotics, antimetabolites, etc.

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-8951f, MAG-CPT, amsacrine, etoposide, etoposide phosphate, teniposide, doxorubicin, paclitaxel, docetaxel, gemcitabine, baccatin III, 10-deacetyltaxol, 7-xylosyl-10-deacetyltaxol, cephalomannine, 10-deacetyl-7-epi-taxol, 7-epitaxol, 10-deacetylbaccatin III, 10-deacetyl cephalomannine, and combinations thereof.

In some embodiments, the chemotherapeutic agent is selected from the group consisting of gemcitabine, paclitaxel, docetaxel, and etoposide, and combinations thereof.

In particular embodiments, the methods described herein can be used in the treatment of various types of solid tumors. Examples of solid tumors include, but are not limited to tumors of the following organs: the skin, breast, brain, cervix, testis, heart, lung, gastrointestinal tract, genitourinary tract, liver, bone, nervous system, reproductive system, and adrenal glands.

Malignant tumors which can be treated by methods described herein can be used in the treatment of cancer, include without limitation adrenal tumors (e.g., adrenocortical carcinoma), anal, bile duct, bladder, bone tumors (e.g., Ewing's sarcoma, osteosarcoma, malignant fibrous histiocytoma), brain/CNS (tumors e.g., astrocytoma, glioma, glioblastoma, childhood tumors, such as atypical teratoid/rhabdoid tumor, germ cell tumor, embryonal tumor, ependymoma), breast tumors (including without limitation ductal carcinoma in situ, carcinoma, cervical, colon/rectum, endometrial, esophageal, eye (e.g., melanoma, retinoblastoma), gallbladder, gastrointestinal, kidney (e.g., renal cell, Wilms' tumor), heart, head and neck, laryngeal and hypopharyngeal, liver, lung, oral (e.g., lip, mouth, salivary gland) mesothelioma, nasopharyngeal, neuroblastoma, ovarian, pancreatic, peritoneal, pituitary, prostate, retinoblastoma, rhabdomyosarcoma, salivary gland, sarcoma (e.g., Kaposi's sarcoma), skin (e.g., squamous cell carcinoma, basal cell carcinoma, melanoma), small intestine, stomach, soft tissue sarcoma (such as fibrosarcoma), rhabdomyosarcoma, testicular, thymus, thyroid, parathyroid, uterine (including without limitation endometrial, fallopian tube), and vaginal tumor and the metastases thereof. In some embodiments, the tumor is selected from the group consisting of breast, lung, GI tract, skin, and soft tissue tumors.

Dosage, Relative Timing and Administration

AAA Dosage:

As discussed above, in certain embodiments, the AAA dose can be up to several times higher than the currently approved dose designed for daily administration and could be as high as the maximum tolerated dose of that particular AAA. In certain embodiments of the invention, the AAA is administered at the maximum tolerated dose of the AAA, about 90% of the tolerated dose of the AAA, about 80% of the tolerated dose of the AAA, about 70% of the tolerated dose of the AAA, about 60% of the tolerated dose of the AAA, about 50% of the tolerated dose of the AAA, about 40% of the tolerated dose of the AAA, about 30% of the tolerated dose of the AAA, about 20% of the tolerated dose of the AAA, or about 10% of the tolerated dose of the AAA. In further embodiments of the invention, the AAA is administered at the approved dose for daily administration, about twice the approved dose for daily administration, about three times the approved dose for daily administration, about four times the approved dose for daily administration, about five times the approved dose for daily administration, about six times the approved dose for daily administration, about seven times the approved dose for daily administration, about eight times the approved dose for daily administration, about nine times the approved dose for daily administration, or about ten times the approved dose for daily administration. Accordingly the effective dose range of AAA as a chemosensitization agent will be broader than that of AAA as currently approved or, if not yet approved, contemplated for therapy.

The dosage of anti-angiogenic agent to be employed for chemosensitization can be ascertained by conducting studies, such as that described in Example 21. However, if not additional increase in ASMase activity (for example by measuring ASMase directly or sphingolipid or ceramide) is observed with an incremental increase in AAA dose, no additional drug should generally be administered as detailed in Example 21.

The approved dosages of several short-acting AAAs are provided below as additional guidance. Based on clinical results available and approved dosage information for axitinib, it is anticipated that a dosage range of axitinib will exceed 20 mg, up to a dose that induces maximal ASMase activation but not higher than a maximum tolerated dose (MTD) will be effective. 20 mg is the current daily dose used in metastatic renal cancer therapy. Of course, this range is subject to adjustment and optimization in order to obtain as high ASMase activation as possible. For example, this can be done as outlined in Example 21. Similarly, dosage determination of sunitinib would start with oral administration of an amount between 2.5 mg and higher up to the MTD mg and escalated in such increments, proceeding otherwise outlined in the preceding sentences.

TABLE 1

Published Amounts of Short-Acting Anti-angiogenic Agents

| AAA | Approved or Clinically Used Dosage(s) |
| --- | --- |
| Axitinib | Starting dose 5 mg BID (starting dose can be increased or reduced by 1 or 5 mg increments |
| Sunitinib | 37.5/day or 50 mg/day depending on indication (adjustments available in 12.5 mg increments) |
| Cediranib | Not FDA approved: 30 mg/day has been used in an NIH clinical study |
| Pazopanib | 800 mg/day (if tolerated can be increased) in 200 mg increments |

Any suitable method of administration oral or parenteral indicated for the AAA may be used. In certain embodiments, the AAA is administered orally. In further embodiments, the AAA is administered parenterally.

Chemotherapeutic Agent Dosage

In certain embodiments of the disclosure, the amount of chemotherapeutic agent will be no higher than a dose-limiting toxicity amount. For example, the chemotherapeutic agents provided below are indicated (in their FDA labels) to be dosed at the following amounts:

| Chemotherapeutic Agent | Recommended Dosage |
| --- | --- |
| Paclitaxel | 135 mg/m2 to 175 mg/m2 (although dosages up to 420 mg/m2 have been used in safety studies) infused i.v. over 3 or 4 hours (and up to 24 hours) every three weeks |
| Docetaxel | from 60 to 100 mg/m2 with 75 mg/m2 being a commonly prescribed amount for various indications |
| Etoposide | Oral or iv administration. IV: 5 to 100 mg/m2 every day or every other day for 5 days; oral dose is generally 2x times the iv amount. |
| Gemcitabine | From 1000 mg/m2 to 12000 mg/m2 depending on indication and tolerance (can be adjusted in 200 mg increments) |

As described in Example 17, ASMase activation occurs in a dose-dependent manner upon administration of a chemotherapeutic (FIG. 14D). Furthermore, ASMase activation has been shown by the present inventors to correlate with survival. This indicates that the dose of chemotherapy drug, like the dose of SDRT, should be increased to the point where maximal ASMase activity is achieved provided of course that the maximum tolerated dose is not reached earlier.

Frequency and Timing:

The timing of chemotherapy administration should be arranged to fall within the increased ASMase activity. In particular embodiments of the invention, the chemotherapeutic agent is administered about 0.5 to 5 hours, about 0.5 to 4 hours, about 0.5 to 3 hours, about 0.5 to 2 hours, about 0.5 to 1.5 hours, about 0.5 to 1 hour, 1 to 5 hours, about 1 to 4 hours, about 1 to 3 hours, about 1 to 2 hours, about 1 to 1.5 hour, 1.5 to 5 hours, about 1.5 to 4 hours, about 1.5 to 3 hours, about 1.5 to 2 hours, 2 to 5 hours, about 2 to 4 hours, about 2 to 3 hours, about 3 to 5 hours, about 3 to 4 hours, or about 4 to 5 hours after administration of the AAA. In certain embodiments of the invention, the chemotherapeutic agent is administered no more than about 2 hours after administration of the AAA. In further embodiments of the invention, the chemotherapeutic agent is administered no more than about 1.5 hours after administration of the AAA. In still further embodiments of the invention, the chemotherapeutic agent is administered no more than about 1 hour after administration of the AAA. In yet further embodiments the administration of the chemotherapeutic agent is commenced within a half-hour after administration of the AAA. The duration of chemotherapy infusion will generally be monitored for that which produces the best synergy with the AAA, again attempting different rates of infusion, using ASMase signaling (or perfusion alteration) as a biomarker and/or monitoring tumor response.

In certain embodiments, chemotherapy administration takes place in terms of dosage, frequency, and duration accordance with the indication of the particular chemotherapeutic agent used. The frequency of administration will generally be once on the day of treatment and the space between treatments with AAA will be determined taking into account the decay time of the anti-angiogenic agent as mentioned above and the time period between cycles of the chemotherapy. Typically chemotherapeutic agents that are administered parenterally are infused over a period of time ranging from about 20 minutes up to about an hour.

EXAMPLES

Materials and Methods:

Cell Culture

BAEC were established from the intima of bovine aorta as described[1]. Stock cultures were grown in 100-mm dishes in Dulbecco's modified Eagle's medium (DMEM) supplemented with glucose (1 g/liter), 5% heat-inactivated calf serum (CS), penicillin (50 units/ml), and streptomycin (50 µg/ml). Purified human recombinant bFGF (1 ng/ml; R&D Systems, Inc., Minneapolis, Minn.) was added every other day during the exponential growth phase. After 8-10 days in culture, cells reach confluence and exhibit features of contact-inhibited monolayers. These plateau phase cells were either used for experiments, or further sub-cultured (up to a maximum of 10 times) at a split ratio of 1:8. For sub-culturing, monolayers were dissociated with STV (0.05% trypsin and 0.02% EDTA in PBS) for 2-3 min at 22° C., washed twice in 5% CS-DMEM, and resuspended in DMEM with supplements as above. These mild conditions of trypsinization were sufficient to detach cells but not injure, stimulate, or affect cell function in a detectable way. BAEC were maintained at 37° C. in 10% $CO_2$ humidified incubators.

HCAEC were obtained from Clonetics™ Coronary Artery Endothelial Cell Systems (Cambrex Bio Science Inc.). For HCAEC culturing and sub-culturing Clonetics cell system components were used: EBM®-2, Endothelial Cell Basal Medium-2 with addition of Clonetics EGM-2-MV SingleQuots containing growth supplements (Cambrex) (Biomedical Technologies, Inc.). For sub-culturing, monolayers were dissociated with Clonetics® Trypsin/EDTA solution for 2-3 min at 22° C. at a split ratio of 1:4 to expand the cell population for experiments. HCAEC cultures were maintained at 37° C. in 5% $CO_2$ humidified incubators.

Apoptosis In Vitro

Apoptosis was assessed in vitro by examining morphologic changes in nuclear chromatin using bis-benzimide trihydrochloride (Hoechst #33258; Sigma-Aldrich, Milwaukee Wis.). BAEC and HCAEC monolayer cultures were first detached using 0.25% trypsin and 0.02% EDTA in HBSS and then combined with the floating population of cells. The cell pellet was washed in PBS, resuspended in 3% paraformaldehyde, and incubated for 10 min at 22° C. Following the removal of fixative, cells were resuspended in PBS containing 8 µg/ml of Hoechst-33258. Following a 15-min incubation at 22° C., cells were placed on a glass slide, and scored for the incidence of apoptotic chromatin changes using fluorescence microscope. Cells exhibiting at least three apoptotic bodies were counted as apoptotic.

Ceramide Quantitation

After treatment, cells were placed on ice, washed with cold PBS, and lipids were extracted by addition of scraped cells in methanol to an equal volume of chloroform and 0.6 volume of buffered saline/EDTA solution (135 mM NaCl, 4.5 mM KCl, 1.5 mM $CaCl_2$, 0.5 mM MgCl2, 5.6 mM glucose, 10 mM HEPES pH 7.2, 10 mM EDTA). Lipids in the organic phase extract were dried under $N_2$ and subjected to mild alkaline hydrolysis (0.1 N methanolic KOH for 1 hour at 37° C.) to remove glycerophospholipids. Samples were re-extracted, and the organic phase was dried under $N_2$. Ceramide contained in each sample was resuspended in a 100 µl reaction mixture containing 150 µg of cardiolipin, 280 µM diethylenetriaminepentaacetic acid, 51 mM octyl-β-D-glucopyranoside (Calbiochem), 50 mM NaCl, 51 mM imidazole, 1 mM EDTA, 12.5 mM $MgCl_2$, 2 mM dithiothreitol, 0.7% glycerol, 70 µM β-mercaptoethanol, 1 mM ATP, 10 µCi of [γ-$^{32}$P]ATP, 35 µg/ml *Escherichia coli* diacylglycerol kinase (Calbiochem) at pH 6.5. After 30 minutes at room temperature, the reaction was stopped by extraction of lipids with 1 ml of chloroform:methanol:1 N HCl (100:100:1), 170 µl of buffered saline solution (BSS) (135 mM NaCl, 1.5 mM $CaCl_2$), 0.5 mM MgCl2, 5.6 mM glucose, and 10 mM HEPES (pH 7.2), and 30 µl of 100 mM EDTA. The lower organic phase was dried under $N_2$. Ceramide-1 phosphate was resolved by thin-layer chromatography on silica gel 60 plates (Whatman) using a solvent system of chloroform:methanol:acetic acid (65:15:5, v/v/v) and detected by autoradiography, and incorporated $^{32}$P was quantified by liquid scintillation counting. The level of ceramide was determined by comparison with a standard curve generated concomitantly of known amounts of ceramide.

ASMase Activity Assay

ASMase activity was quantified by radioenzymatic assay using [$^{14}$C-methylcholine]sphingomyelin (Amersham) as substrate as described (Schissel et al. *J Biol Chem*, 271, 18431-18436, 1996). Cell lysates were incubated with [$^{14}$C-methylcholine]-sphingomyelin substrate (0.026 mCi/9.5 nmol) in 250 mM sodium acetate, pH 5.0 supplemented with 0.1% Triton X-100 and 1 mM EDTA or 0.1 mM ZnCl.

Reactions were terminated after 1 h with CHCl3:MeOH:1N HCl (100:100:1, v/v/v), and [$^{14}$C-methylcholine]phosphocholine product in the aqueous layer of the Folch extract was quantified using a Beckman Packard 2200 CA Tricarb scintillation counter. For detection of ASMase activity in patients, 10 µl of serum was used.

CRM Detection by Confocal Microscopy

BAEC were grown on CC2-treated chamber slides (Nalge Nunc International Corp., Naperville, USA) and then exposed to etoposide or paclitaxel with or without pre-incubation with Nystatin (30 µg/ml, Sigma) for 30 min. BAEC were then washed in cold PBS, fixed for 15 min in fresh 2% paraformaldehyde, washed 2× with cold PBS, and blocked with 5% FBS in PBS for 20 min at room temperature. Cells were stained with anti-ceramide MID 15B4 IgM (Alexis Corporation) at 1:50 dilution for 1 hour at room temperature, washed 3× in PBS, and thereafter with Texas Red-conjugated secondary antibody (Jackson Immunoresearch Laboratories, Inc.) at 1:500 dilution for 1 hour at room temperature. Nonspecific fluorescence was excluded using isotype control IgM (BD Biosciences). Cells were washed 3×, stained with DAPI and mounted in 0.1% para-phenylenediamine. Fluorescence was detected using Leica TCS SP2 AOBS 1- and 2-photon laser scanning confocal (DMRXA2 upright stand) microscope coupled with Meta-Morph 7.5 (Molecular Devices). Number of CRMs in membranes of endothelial cells was analyzed using MetaMorph 7.5 software that allowed outlining of regions containing CRMs based on two criteria: 1) CRM size (≥500 nm); 2) Intensity of ceramide staining. Mice: asmase$^{-/+}$ and asmase$^{-/-}$ mice, maintained in a SCID background, were propagated using heterozygous breeding pairs and genotyped as previously described (Santana et al. *Cell*, 86, 189-199, 1996; Grassme et al. *Nat Med* 9, 322-330 (2003). 6-12 week-old C57BL6/SV129 male mice, purchased from The Jackson Laboratory (Bar Harbor).

Tumor Animal Models

Human HCT-116 colon cancer cells and MCA/129 murine sarcoma cells were maintained in DMEM with 10% fetal bovine serum, with 100 u/ml penicillin and 100 µg/ml streptomycin. Cells were grown as monolayers in 75 cm$^2$ culture flasks at 37° C. in 10% $CO_2$ humidified incubators. Cells were trypsinized, washed in PBS and diluted in Matrigel/PBS solution (40:60 v/v) for HCT-116 xenografts or in PBS for MCA/129 syngeneic tumor grafts. Cells (3×10$^6$ for HCT-116 or 1×10$^6$ for MCA129) were injected subcutaneously into the flanks of mice (Garcia-Barros et al. *Science* 300, 1155-1159, 2003).

Tumor Response In Vivo

SCID$^{asmase+/+}$ and SCID$^{asmase-/-}$ mice harboring HCT-116 tumors (50-100 mm$^3$) were treated with three i.p. injections of 35-50 mg/kg etoposide (Novaplus®), or 15-25 mg/kg paclitaxel (Hospira), or 1-6 mg/kg cisplatin (APP Pharmaceuticals, LLC) in a bi-weekly schedule with or without i.v. DC101 (1600 µg/25 gm mouse), or control IgG. For sarcoma studies, Sv129/B16 mice harboring MCA/129 tumors (100-150 mm$^3$) were treated with three i.p. injections of 240 mg/kg gemcitabine on a bi-weekly schedule with or without i.v. DC-101. Tumor volume, based on caliper measurements (length and width in millimeters), was calculated daily using the following formula: 0.5×length×width$^2$.

Apoptosis In Vivo

To evaluate acute endothelial apoptosis, tumors were grown in mice and treated with drugs as above. After the first treatment, tumors were harvested at specified times, placed into formalin overnight and paraffin-embedded the next day. Paraffin-embedded sections (5 µm) were co-stained for apoptotic endothelium using TUNEL and the endothelial-specific monoclonal antibody MECA-32 (Developmental Studies Hybridoma Bank, developed under the auspices of the NICHD and maintained by The University of Iowa, Iowa).

Phase II Trial of Gemcitabine and Docetaxel with Bevacizumab in Selected Sarcoma Subtypes Patients with metastatic or locally-recurrent leiomyosarcoma, pleomorphic undifferentiated sarcoma, pleomorphic liposarcoma, rhabdomyosarcoma or angiosarcoma, were treated on a phase II trial of gemcitabine, docetaxel and bevacizumab. Initially the trial was a double-blind, placebo-controlled, randomized trial of gemcitabine and docetaxel with or without bevacizumab, which was modified to a single-arm, open-label, non-randomized study of gemcitabine, docetaxel and bevacizumab. The protocol was approved by the Institutional Review Board of Memorial-Sloan Kettering Cancer Center, and all patients provided written informed consent (Clinicaltrials.gov identifier NCT00887809).

Patients were treated with bevacizumab 15 mg/kg on day 1 of each 21-day cycle intravenously over 30 min with gemcitabine 900 mg/m$^2$ over 90 min on day 1 and 8 and docetaxel 75 mg/m$^2$ over 60 min on day 8. Initially, gemcitabine was administered immediately following bevacizumab. However, based on the results of our pre-clinical studies, the protocol was later amended so that gemcitabine was administered at 1 hour after bevacizumab.

Volumetric measurement of tumors was performed on an exploratory basis as the original study was not designed or powered to specifically investigate the clinical application of timed anti-angiogenic therapy as a method of tumor chemosensitization. In light of the results from our animal studies, which were made part way through the clinical study period, volumetric measurements were proposed to more ideally facilitate comparison with our pre-clinical data. Furthermore, they likely provide a more meaningful assessment of tumor response than the RECIST based evaluation for soft tissue sarcoma. Therefore, on completion of the study, volumetric analysis was performed by a study radiologist (R.L.) blinded to assignment of patients to the bevacizumab administration schedule or the initial placebo cohort. Baseline CT or MM was used to identify a dominant target lesion for measurement. Follow-up scans were evaluated for best response. Tumor contours were defined manually and summed across all axial slices to calculate a total volume measurement. Tumor response was defined as at least a 30% reduction in tumor volume. Both a two-tailed Fisher's Exact Test and the Mann-Whitney Rank-Sum test were employed to evaluate significance in patient volumetric response rates at the first interval treatment scan (week 6) and at time of maximum treatment response.

Microvascular Vasoconstriction as Ascertained for Example by Perfusion Alterations Microvascular vasoconstriction was assessed by in situ tumor perfusion measurements using DCE-MRI with Gd-DTPA (Cho et al. Neoplasia 11, 247-259, 2009). A syringe filled with the contrast agent Gd-DTPA (0.2 mM Gd/kg, Magnevist; Berlex Laboratories, Inc., Wayne, N.J.) was connected to the three-way stopcock through Gd-DTPA-filled tubing. The entire assembly including the anesthetized animal was positioned inside the magnet using a spirit level and the axial MR profile. Respiration was monitored during the MR experiment. The MRI coil was tuned and matched to the proton frequency, followed by shimming of the sample. Tissue perfusion was calculated according to a model developed by Hoffmann et al. (Hoffmann et al. *Society of Magnetic Resonance in Medicine* 33, 506-514, 1995). This model is based on the linear relationship between measured saturation recovery MR signal and the concentration of Gd-DTPA in the tissue. Akep value is analogous to the slope of time-dependent MR signal enhancement and is considered an approximate measure of blood flow/perfusion of the tumor tissue. Akep maps were generated each of the tumor slices. Additionally, quantification analysis of DCE-MRI studies and their clinical applications are discussed by Padhani and Husband in *Dynamic contrast-enhanced MRI studies in oncology with an emphasis on quantification, validation and human studies* (*Clin Radiol.* 2001 August; 56(8): 607-20.)

Perfusion Measurements Using Hoechst 33342

The fluorescent dye Hoechst 33342 (5 mg/mL in physiologic saline; 15 mg/kg; nominal injected volume, 0.1 mL; Sigma-Aldrich) was administered via tail vein injection at indicated times before and after treatment.

EPR Imaging

EPR imaging which measures oxygen levels in the tumor was carried out as described previously (Epel et al. *Concepts in magnetic resonance. Part B, Magnetic resonance engineering* 33B, 163-176, 2008). The spin probe used for the EPR imaging was a 1 mM solution of OX063H radical (methyltris[8-carboxy-2,2,6,6-tetrakis[(2-hydroxyethyl] benzo[1,2-d:4,5-d']bis[1,3]dithiol-4-yl]-trisodium salt, from GE Healthcare. The spin probe was enclosed in a borosilicate glass cylinder. Samples were deoxygenated by multiple-cycle freeze-pump-thaw technique and flame-sealed. Samples were then placed into the resonator, along the resonator's axis of symmetry and centered in the axial plane of the resonator.

IVIM DW-MRI

IVIM DW-MRI was first described by Le Bihan et al. (MR imaging of intravoxel incoherent motions: application to diffusion and perfusion in neurologic disorders. *Radiology* 1986; 161: 401-407). The novelty of our approach lies in repeatedly acquiring IVIM data over time (e.g. "dynamic" IVIM) to monitor the acute effects of radiation (or chemotherapy), a strategy which has not been previously reported. No intravenous contrast administration is required, and IVIM parameters can be measured many times, allowing us to define kinetics of vascular dysfunction after radiation or chemotherapy. Other alternatives, such as DCE-MRI or $^{15}$O-PET, would not serve our purpose as well: although they may be highly reflective of tissue vascularity they cannot be re-injected into a patient to serially monitor changes in vascularity over time. IVIM parameters including perfusion fraction (f), pseudo-diffusion coefficient (D*) and diffusion coefficient (D) were calculated for each lesion, using a biexponential signal decay model and incorporating a correction to account for differences in the T1 and T2 relaxation times of tissue and blood, respectively.

In addition to DCE-MRI and IVIM DW-MRI, perfusion can be determined using any of the methods known in the art. ASMase or apoptotic ceramide levels can be used as surrogates.

Ceramide Mass Spectrometry

Pro-apoptotic ceramide species (C16:0, C18:0) and anti-apoptotic species (C24:0) were measured for the studies included in this disclosure in the MSKCC Mass Spectrometry Core Facility according to standard procedures (see, e.g., Merrill, A. H. Jr., 2011, Chem. Rev. 111:6387-6642).

Example 1

Chemotherapeutic Agents Activate ASMase/Ceramide Pathway in Endothelial Cells

Figure 1C:
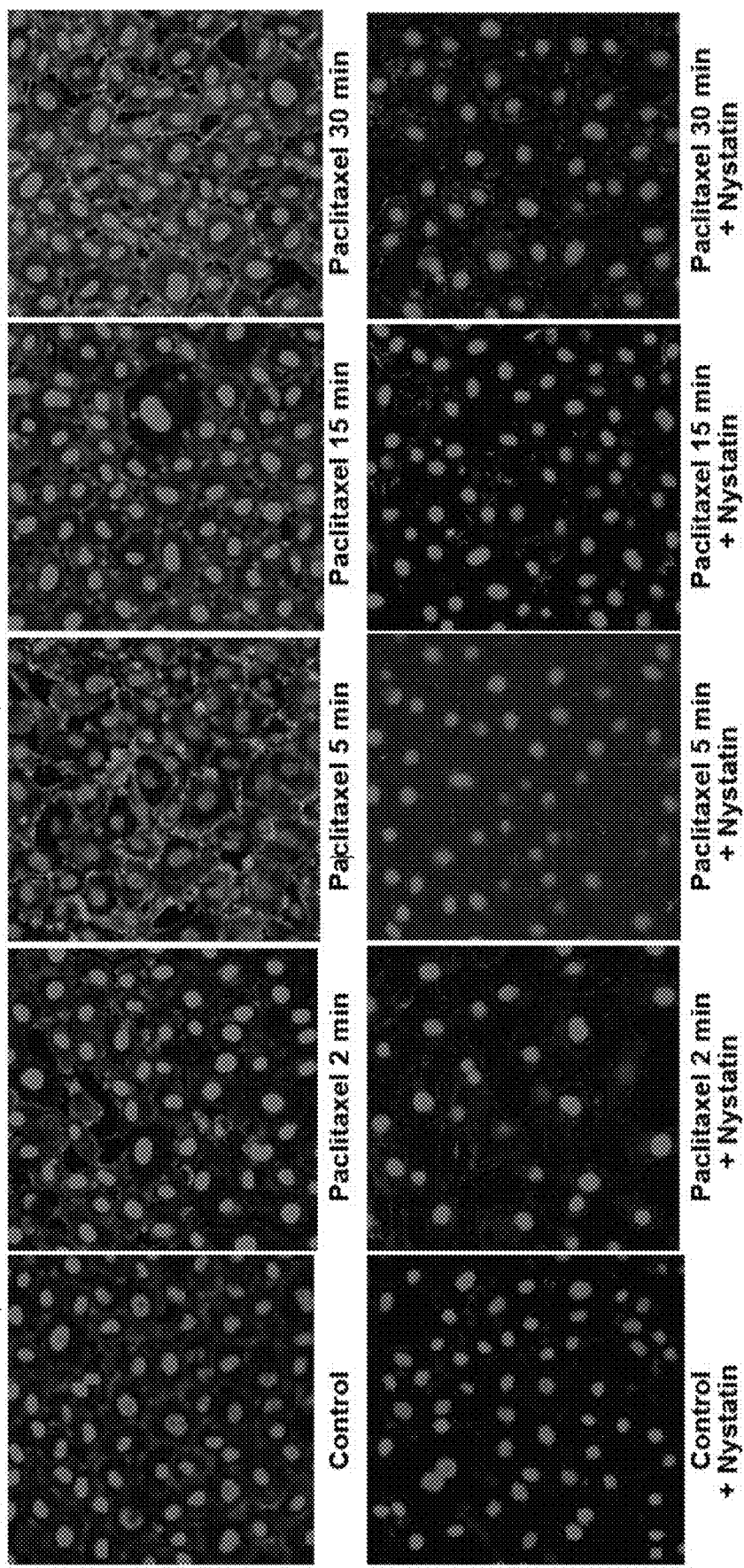
FIG. 1C is a series of microphotographs showing the formation of CRM over time in BAEC monolayers exposed to paclitaxel (100 nM), in the absence (upper panel) or presence (lower panel) of 30 μg/mL nystatin (30 min pretreatment). BAEC were co-stained with anti-ceramide antibody (which binds to the cell membrane as indicated by the grey area between the cell nuclei most prominent in the upper right three panels of FIG. 1C, wherein the cell nuclei appear as discreet the latter appearing as discrete globules and DAPI (to stain nuclei which appear as globules) in order to localize CRMs to plasma membranes.

To test the effect of chemotherapy on ASMase signaling and ceramide production, BAEC were treated with paclitaxel (100 nM) and ASMase activity was determined by radioenzymatic assay (Rotolo et al, infra) using [$^{14}$C-methylcholine] sphingomyelin (Amersham) as substrate (FIG. 1A). Induction of ASMase activity was observed within 5 minutes after treatment, and the activation continued for 30 minutes. Ceramide generation was monitored using the diacylglycerol kinase assay (Stancevic et al. PLoS ONE 8, e69025, 2013). Consistent with what was observed with ASMase activity, ceramide generation peaked within minutes following the treatment, and persisted for 30 minutes (FIG. 1B). Since ceramide generation is associated with the formation of CRMs, BAEC monolayers were stained with anti-ceramide antibody (MID 15B4 IgM (Alexis Corporation) and CRM's were visualized using confocal microscopy (FIG. 1C). As anticipated, CRM formation peaked at 5 minutes, and remained elevated for 30 minutes (FIG. 1C). Nystatin is a cholesterol-depleting agent which disrupts sphingomyelin-rich cell surface raft microdomains, thus inhibiting ASMase targeting of sphingomyelin, and CRM formation. Treatment of BAEC with both paclitaxel and nystatin prevented the formation of CRMs (FIG. 1C), showing that nystatin's interference with ASMase substantially obliterates paclitaxel-mediated ceramide generation and confirms the chemotherapeutic agent's proapoptotic action through ASMase signaling and ceramide production. In further support of this, pre-incubation of BAEC with nystatin prior to treatment with chemotherapy inhibits chemotherapy-induced apoptosis (FIG. 3).

To determine the generality of the results observed, experiments were carried out using an additional endothelial cell line, human coronary artery endothelial cells (HCAEC); experiments were also performed using a different chemotherapeutic agent. Treatment of BAEC with etoposide (50 μM) resulted in activation of ASMase and ceramide formation within a few minutes and the effects remained for 30 min (FIGS. 1D and 1E). Next, HCAEC were treated with paclitaxel (100 nM) (data not shown) and etoposide (50 μM) (FIG. 1F), and ceramide generation was evaluated. Consistent with the results noted when BAEC cells were treated with paclitaxel and etoposide, treatment of HCAEC with either paclitaxel or etoposide leads to the generation of ceramide (FIG. 1F).

To further establish the generality of ASMase activation by various chemotherapeutic agents, BAEC and HCAEC were treated with increasing doses of cisplatin (0.1-50 μM) (data not shown). However, on contrary to the other agents tested, cisplatin treatment failed to activate ASMase and result in generation of ceramide. The cisplatin data notwithstanding, taken together, these results confirm that various chemotherapeutic agents having different mechanisms of action induce ASMase activation and generation of ceramide. The ASMase/ceramide pathway was activated by chemotherapeutic agents that belong to different classes of chemotherapeutic agents, such as: taxanes, topoisomerase inhibitors, and nucleoside analog metabolic inhibitors. Since such chemotherapy agents are characterized by distinct mechanisms of action in tumor cells, it is surprising that a group of such distinct agents converges on a common molecular (ASMase/ceramide) axis in endothelium. The present confirmation that distinct chemotherapeutic agents activate the ASMase/ceramide pathway permits the present inventors to take into account the results of experiments using single dose radiotherapy, which has been reported to activate the same pathway (Rao, S. S. et al., Axitinib sensitization of high Single Dose Radiotherapy. *Radiotherapy and Oncology: Journal of the European Society for Therapeutic Radiology and Oncology* 111, 88-93, doi: 10.1016/j.radonc.2014.02.010 (2014)).

Example 2

ASMase Signaling is Required for Chemotherapy-Induced Endothelial Cell Apoptosis In Vivo Since the ASMase/ceramide pathway is known to play a critical role in endothelial injury and dysfunction, BAEC and HCAEC were treated with paclitaxel (100 nM), etoposide (50 μM), and cisplatin (0.1-50 μM), and endothelial apoptosis was assessed. Treatment of cells with paclitaxel and etoposide induced apoptosis within 2 hours of drug exposure (FIGS. 2A and 2B). On contrary, cisplatin failed to trigger an appropriate apoptotic response in bovine endothelial cells in this experiment even at high concentrations (50 μM) (FIG. 2C).

Taken together, these results suggest that ASMase is a determinant component of chemotherapy-induced endothelial cell death.

Example 3

Pro-Angiogenic Factors Inhibit Chemotherapy-Induced Endothelial Cell Apoptosis

Various pro-angiogenic factors have been shown to inhibit ASMase activation in endothelial cells. To set the basis for experiments involving evaluation of anti-angiogenic therapy in combination with chemotherapy, and the role of ASMase/ceramide pathway in this process, the effects of various factors on the chemotherapy induced cell death were assessed. BAEC were pre-incubated for 30 min with bFGF (2 ng/mL), VEGF (2 ng/mL) or nystatin (30 μg/mL) prior to treatment with etoposide (50 and apoptosis was evaluated after 8 hours using bis-benzamide trihydrochloride staining (FIG. 3). While treatment with etoposide alone significantly induces apoptosis, as seen in the control sample, pre-incubation of BAEC with either basic fibroblast growth factor (bFGF; 2 ng/ml), vascular endothelial growth factor (VEGF; 2 ng/mL), or nystatin (30 μg/ml) substantially inhibits etoposide-induced apoptosis (FIG. 3).

Example 4

Figure 4B:
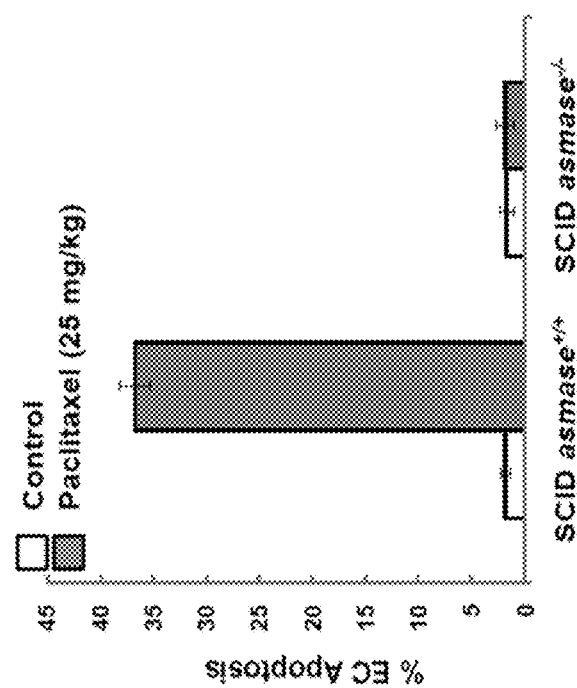
FIG. 4B is a bar graph showing quantification of endothelial cell apoptosis after single dose of paclitaxel.
Figure 4A:
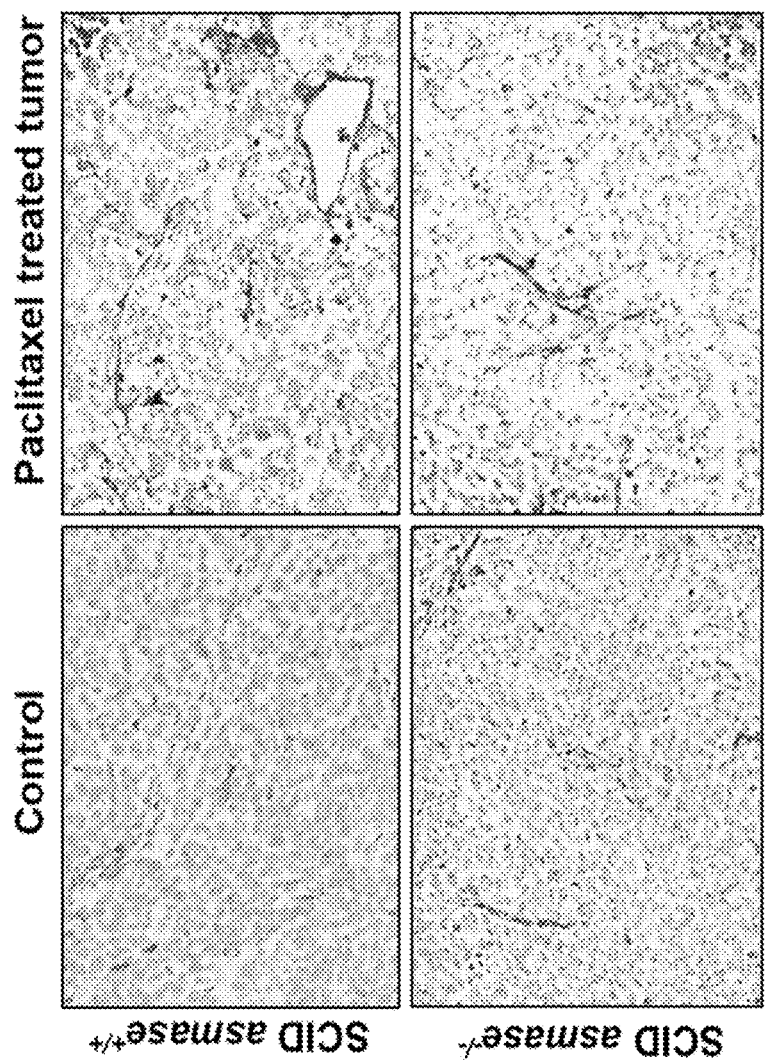
FIG. 4A is a panel of representative 5-μm histologic tumor sections obtained either from controls (left panel) or at 4 hours after exposure of tumor-bearing mice to a single dose of paclitaxel (25 mg/kg i.p., right panel), and stained for endothelial surface marker MECA-32 and TUNEL.

ASMase Signaling is Required for Chemotherapy-Induced Endothelial Cell Apoptosis In Vivo To assess the role of ASMase signaling in in vivo chemotherapy response, two mouse models were used, where two distinct cancer cell lines were implanted in wild type and ASMase deficient mice. First, HCT116 human colorectal cancer xenografts were implanted into immunodeficient wild-type SCID$^{asmase+/+}$ and ASMase deficient SCID$^{asmase-/-}$ mice. Tumor-bearing mice were treated for 4 hours with a single dose of paclitaxel (25 mg/kg), and tumor sections were fixed and double-stained for endothelial surface marker MECA-32 (dark grey plasma membrane) and TUNEL (nuclear dark grey stain) (FIG. 4A). FIG. 4B shows the quantification of endothelial cell apoptosis. While tumors generated in SCID$^{asmase+/+}$ animals exhibited robust endothelial apoptosis, tumors xenografted in SCID$^{asmase-/-}$ littermates were resistant to chemotherapy-induced endothelial cell apoptosis.

Figure 4D:
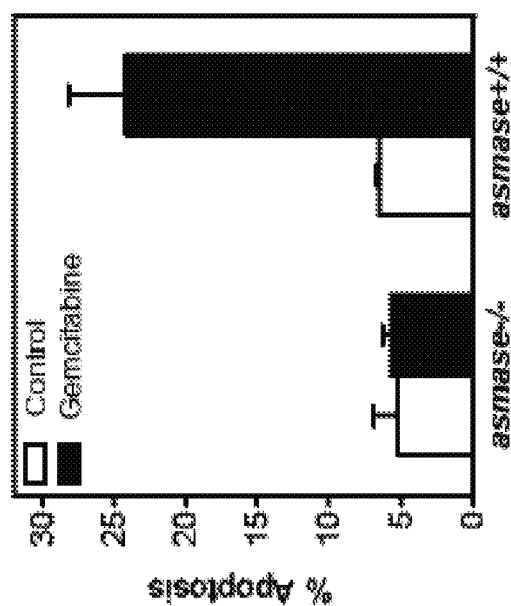
FIG. 4D is quantification of endothelial cell apoptosis in MCA/129 tumors at 4 hours after treatment as in FIG. 4C.
Figure 4C:
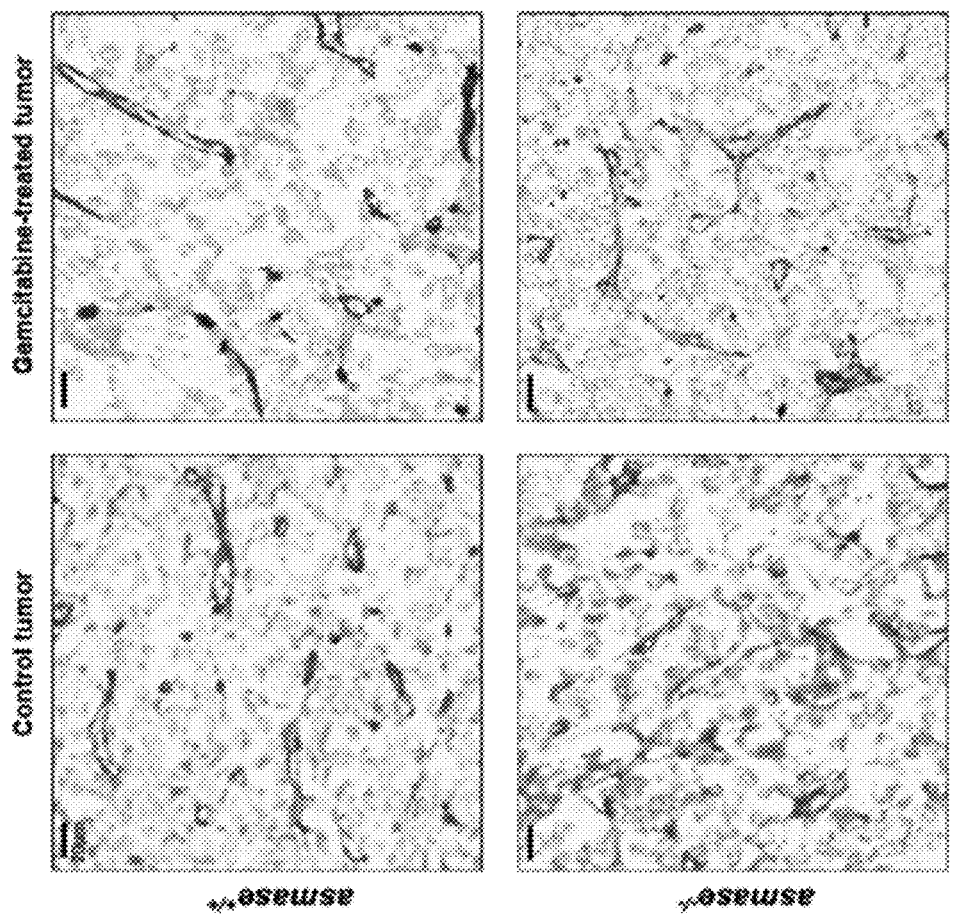
FIG. 4C is a panel of histologic MCA/129 fibrosarcoma sections obtained either from untreated controls (left panel) or at 4 hours after exposure to single dose of gemcitabine (240 mg/kg i.p., right panel), and stained for endothelial surface marker MECA-32 and TUNEL.

Next, a mouse model of MCA/129 fibrosarcomas was used to test the ability of a different chemotherapeutic agent, gemcitabine, to induce apoptosis in ASMase deficient animals. Similar to results obtained using the colorectal cancer model, gemcitabine (240 mg/kg) induced time-dependent endothelial cell apoptosis in Sv129/BL6$^{asmase+/+}$ but not Sv129/BL6$^{asmase-/-}$ mice (FIGS. 4C and 4D). Gemcitabine treatment did not cause tumor cell apoptosis, indicating that the effects are specific to the endothelial cell compartment.

Collectively, these observations indicate that ASMase signaling is required for chemotherapy-induced endothelial cell apoptotic response in vivo. Furthermore, it is observed that ASMase/ceramide pathway mediates tumor growth delay caused by chemotherapy agents that have the ability to activate ASMase/ceramide signaling.

Example 5

Figure 5B:
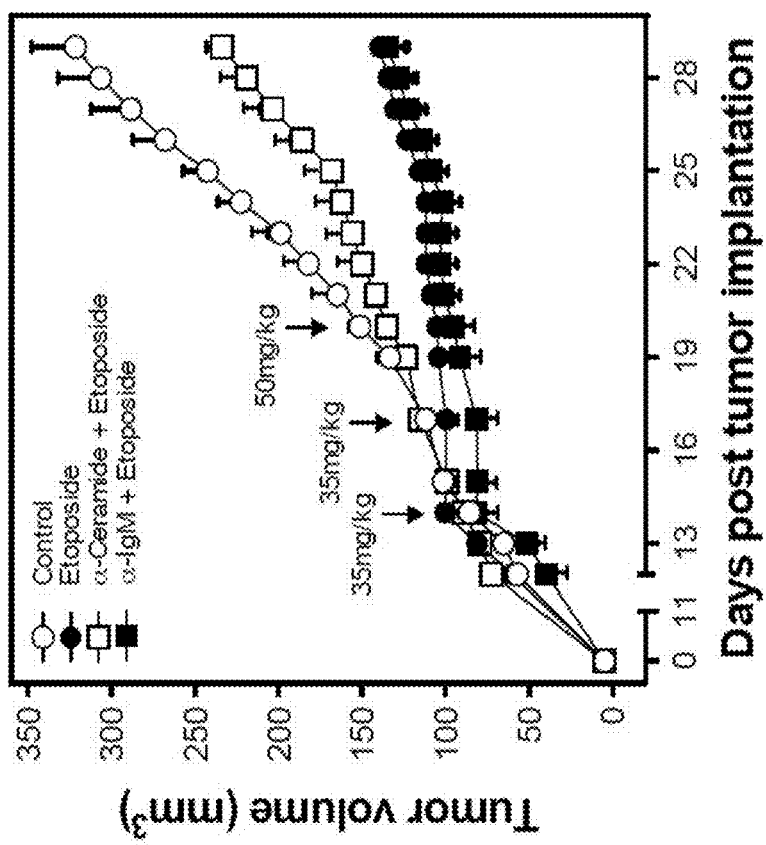
FIGS. 5A and 5B are plots of tumor volume (mm$^3$) versus days post tumor implantation.
Figure 5A:
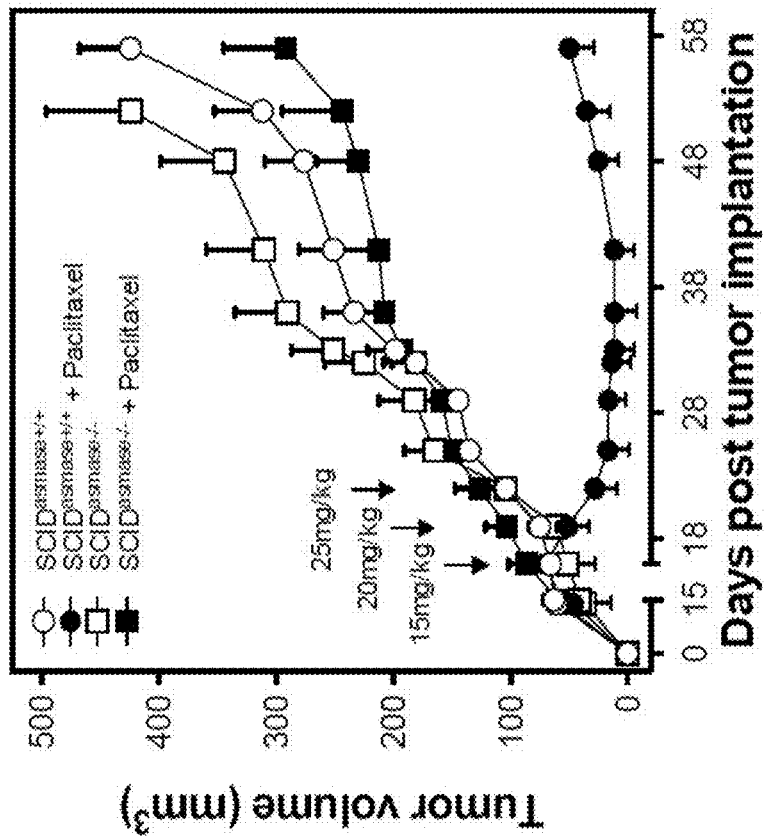

ASMase Signaling is Required for Tumor Response to Chemotherapy in Animal Models Tumor response to chemotherapy in the colorectal HCT116 xenograft model was evaluated. SCID$^{asmase+/+}$ or SCID$^{asmase-/-}$ mice harboring HCT116 tumors (50-70 mm$^3$) were treated with paclitaxel (15/20/25 mg/kg i.p.) three times biweekly. Consistent with the requirement for ASMase signaling in endothelial cell apoptosis, activity of ASMase pathway was required for the effect of chemotherapy on tumor growth delay. HCT116 xenografts in SCID$^{asmase+/+}$ mice treated with paclitaxel exhibited complete tumor response after 10±1 days, while there was no significant tumor response in xenografts in SCID$^{asmase-/-}$ littermates (FIG. 5A). To test that the ASMase requirement is mediated by the generation of ceramide, SCID$^{asmase+/+}$ mice harboring tumors as in FIG. 5A were treated with etoposide (35/35/50 mg/kg i.p.) biweekly in the presence of anti-ceramide or isotype control antibody. As shown in FIG. 5B, intravenous injection of anti-ceramide IgM 1 hour before each etoposide injection resulted in attenuation of tumor growth delay compared to animals treated with isotype control antibody. These results indicate mandatory engagement of endothelial ASMase signaling in parenchymal tumor response to chemotherapeutic agents.

To further test the ability of cisplatin to affect endothelial cell apoptosis and tumor response in vivo, effects of cisplatin on tumor growth were evaluated. In this tumor model, high dose cisplatin treatment (3×6 mg/kg) did not induce significant HCT116 tumor growth delay (FIG. 6F) nor tumor endothelial apoptosis (data not shown).

Example 6

Angiogenic In Vivo Tumor Chemosensitization is Dependent on Timing

Figure 6B:
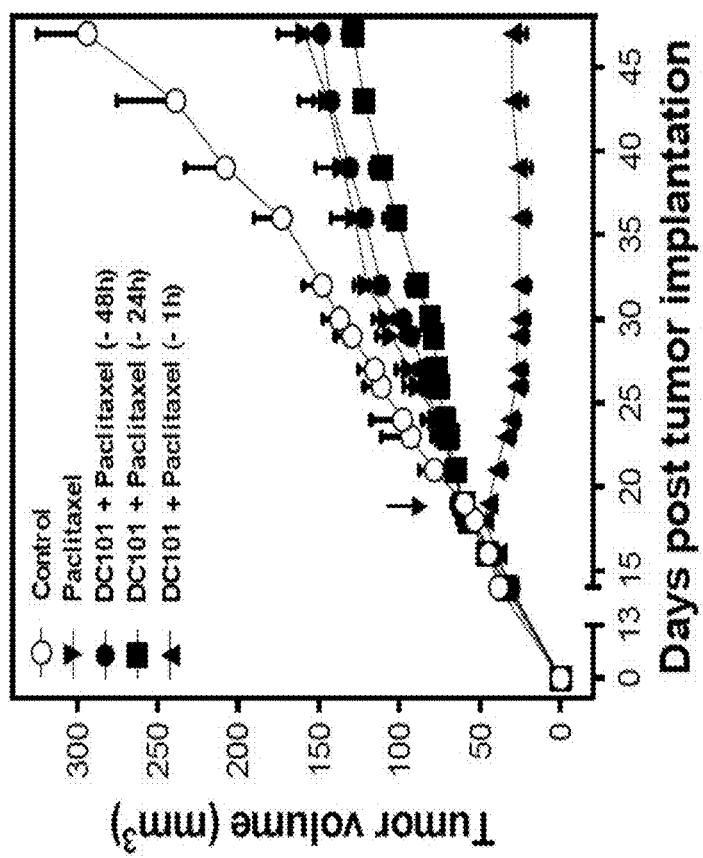
FIGS. 6A, 6B, and 6C are plots of HCT116 tumor volume (mm$^3$) in SCID$^{asmase+/+}$ mice versus days post tumor implantation.
Figure 6A:
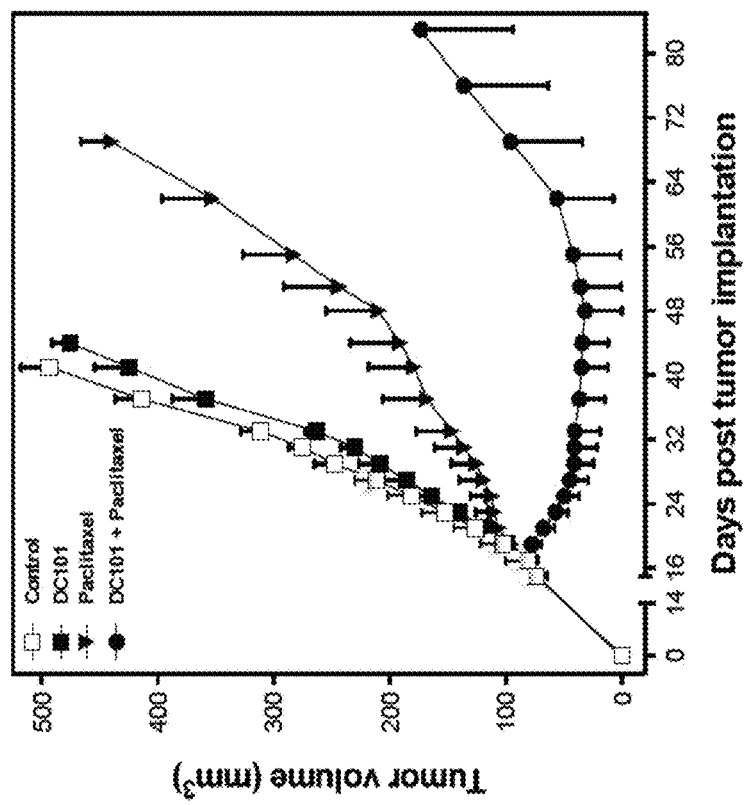
Figure 6D:
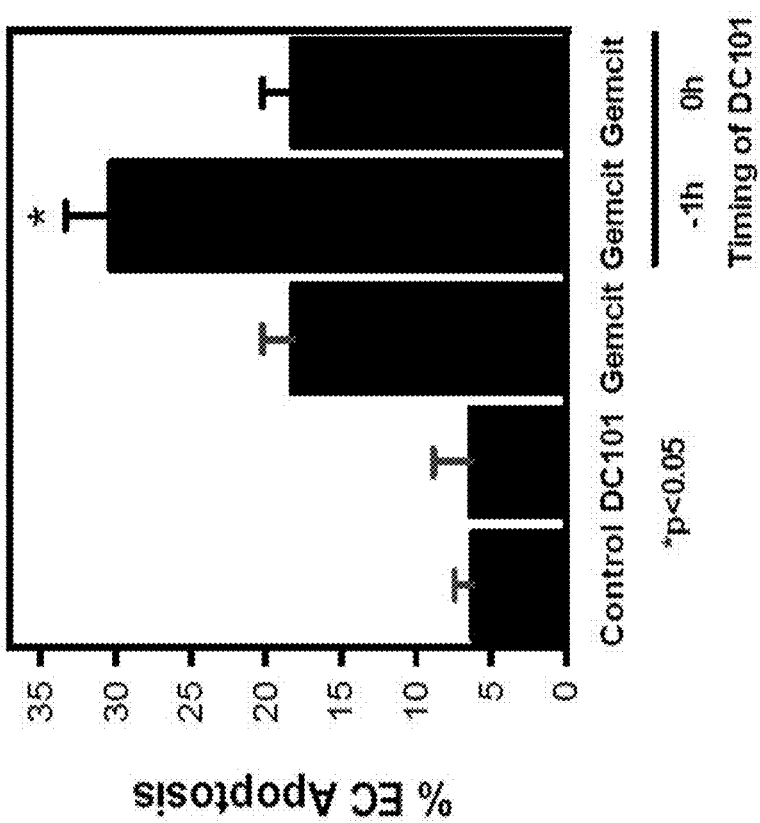
FIG. 6D is a bar graph showing percent of endothelial cell apoptosis following the administration of DC101 (1.6 mg/25 gm mouse i.p.) in combination with gemcitabine (240 mg/kg i.p.) to MCA/129 tumors implanted in sv129/B16$^{asmase+/+}$ mice.
Figure 6C:
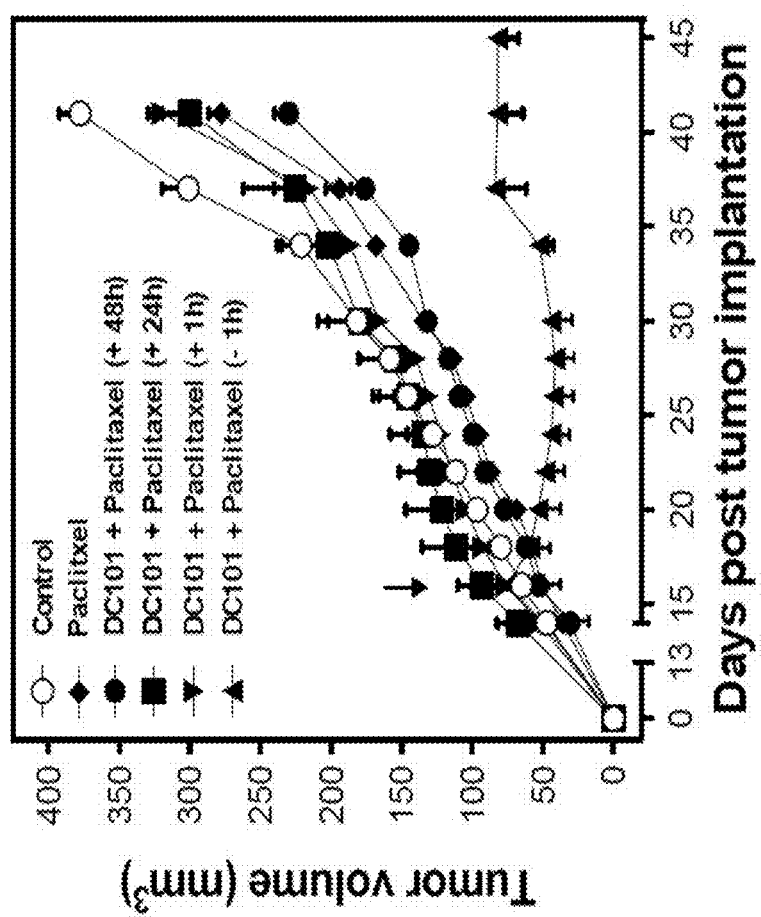
Figure 6F:
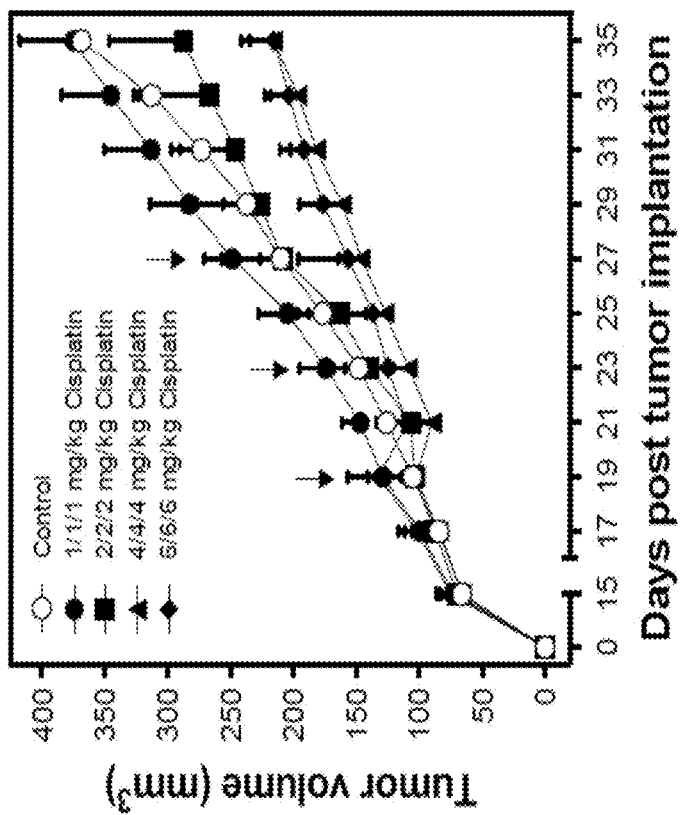
FIG. 6F is a plot of HCT116 tumor volume versus days post tumor implantation in mice treated with various doses of cisplatin.

Virions reports have demonstrated additive effects or synergy when AA As are combined with chemotherapy. A previous study has shown that anti-VEGFR2 IgG antibody DC101 temporarily de-represses endothelial ASMase inhibited by VEGF, which is ubiquitously produced in tumors via hypoxia-mediated HIF-1α transcriptional activation of angiocrines (Truman et al. *PLoS ONE* 5, 2010). Thus, to further explore the notion of endothelial ASMase signaling requirement in response to chemotherapy, DC101 was used in combination with paclitaxel treatment. HCT116 tumors in SCID$^{asmase+/+}$ mice, while slightly affected by 3×15 mg/kg paclitaxel or 1600 μg DC101 alone, exhibited a synergistic tumor response when used together (40% complete responses) (FIG. 6A). Interestingly, anti-angiogenic synergism with chemotherapeutic agents depended on synchronized delivery of agents. No chemosensitization was observed following a single dose of 15 mg/kg paclitaxel if DC101 was injected 3-48 hours prior to paclitaxel (FIG. 6B, cisplatin data not shown). Likewise, there was no added benefit to that of chemotherapy alone if DC101 was injected at any time from 1-48 hours post paclitaxel treatment (FIG. 6C). The synergism was observed only when anti-angiogenic agent was injected 1-2 hours prior to chemotherapy treatment (this interval can be considered within the range 0.5 to 2 hours post AAA administration).

Figure 6E:
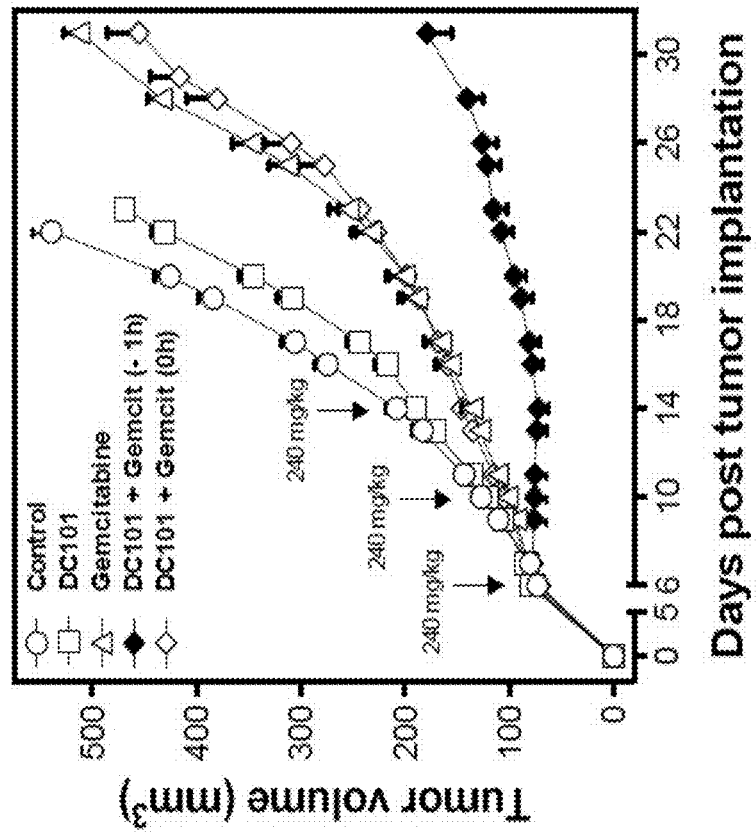
FIG. 6E shows the impact of timing of DC101 relative to gemcitabine on the response of MCA/129 tumors. Experiments were performed as in (FIG. 6D) with DC101 timed either 1 hour before or immediately preceding each dose of gemcitabine (240 mg/kg i.p.). Data (mean±SEM) are collated from 5 mice/group.

Similar results were observed using MCA/129 murine fibrosarcoma tumors implanted in Sv129/Bl6$^{asmase+/+}$ mice. DC101 (1.6 mg/25 gm mouse i.p.) was provided either 1 hour prior to or immediately preceding exposure to gemcitabine (240 mg/kg i.p.). After 4 hours of treatment, tumors were harvested and endothelial cell apoptosis quantified. DC101 was successful in augmenting endothelial apoptosis and tumor growth response only when delivered 1 hour before, but not immediately preceding, each gemcitabine dose (FIGS. 6D and 6E).

The results presented here indicate that chemosensitization occurred only if anti-angiogenic agent was delivered 1-2 hours preceding chemotherapy, but at no other time preceding or after chemotherapy. Thus, there is a chemosensitization interval or window following the administration of anti-angiogenic agent during which treatment with chemotherapy should occur.

Example 7

Figures 7A, 7B:
FIG. 7A includes demographics of patients with metastatic sarcoma treated with bevacizumab, gemcitabine, and docetaxel on a prospective phase II study at MSKCC.
FIG. 7B shows representative CT images of an abdominal wall metastasis at baseline (left), 3 months (center) and 6 months (right) in patient #8 in the 1-hour interval bevacizumab cohort (FIG. 7D).

Synchronized Timing of Bevacizumab with Gemcitabine Improves Tumor Response in Patients with Sarcoma Results shown in Examples 1-6 revealed a significant role of ASMase/ceramide pathway in mediating and facilitating tumor response to chemotherapy. In order to elucidate a role of ASMase in clinical tumor chemotherapy, an Institutional Review Board-approved, prospective phase II clinical trial of gemcitabine and docetaxel with the anti-angiogenic drug bevacizumab in advanced soft tissue sarcoma was carried out at Memorial Sloan Kettering Cancer Center between June 2009 and April 2012(MSKCC 09-015; Clinicaltrials.gov identifier NCT00887809). Patients enrolled in the trial had metastatic or recurrent leiomyosarcoma, pleomorphic undifferentiated sarcoma, pleomorphic liposarcoma, rhabdomyosarcoma or angiosarcoma (FIG. 7A).

A total of 38 patients were treated. A subset of patients received placebo instead of bevacizumab. All other patients were treated on day 1 of each 21-day cycle with bevacizumab (15 mg/kg) delivered intravenously and gemcitabine (900 mg/m$^2$ over 90 min). On day 8, gemcitabine (900 mg/m$^2$ over 90 min) was administered followed by docetaxel (75 mg/m2 over 60 min), without bevacizumab. 16 patients were treated on the immediate bevacizumab-gemcitabine schedule (bevacizumab was delivered intravenously over 30 min, followed by intravenous gemcitabine), 14 were on the 1-hour interval schedule (bevacizumab was delivered 1 hour prior to gemcitabine), while 8 patients received placebo rather than bevacizumab. Volumetric analysis of tumor response in the patients was performed by a study radiologist blinded to assignment of patients to the bevacizumab/gemcitabine administration schedule. Baseline CT scan or MM was used to identify a dominant target lesion for volumetric measurement, followed by volumetric assessment on initial post-treatment follow-up scan (2 months) and over the treatment course (representative CT time course of abdominal metastasis is shown in FIG. 7B showing regression of metastatic tumor).

Figure 7D:
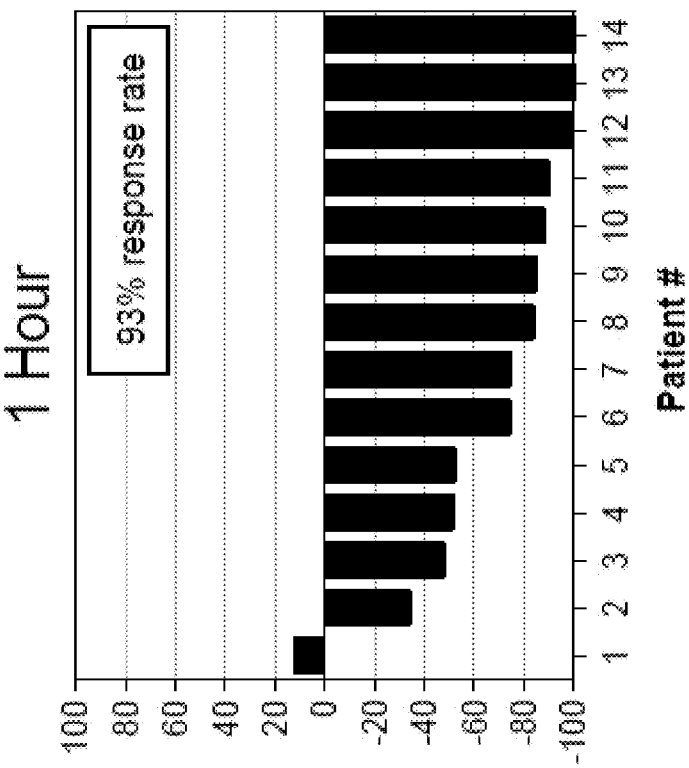
FIGS. 7C and 7D are waterfall plots demonstrating best tumor response based on volumetric change for each patient treated with bevacizumab immediately before (FIG. 7C) or 1 hour before (FIG. 7D) gemcitabine.
Figure 7C:
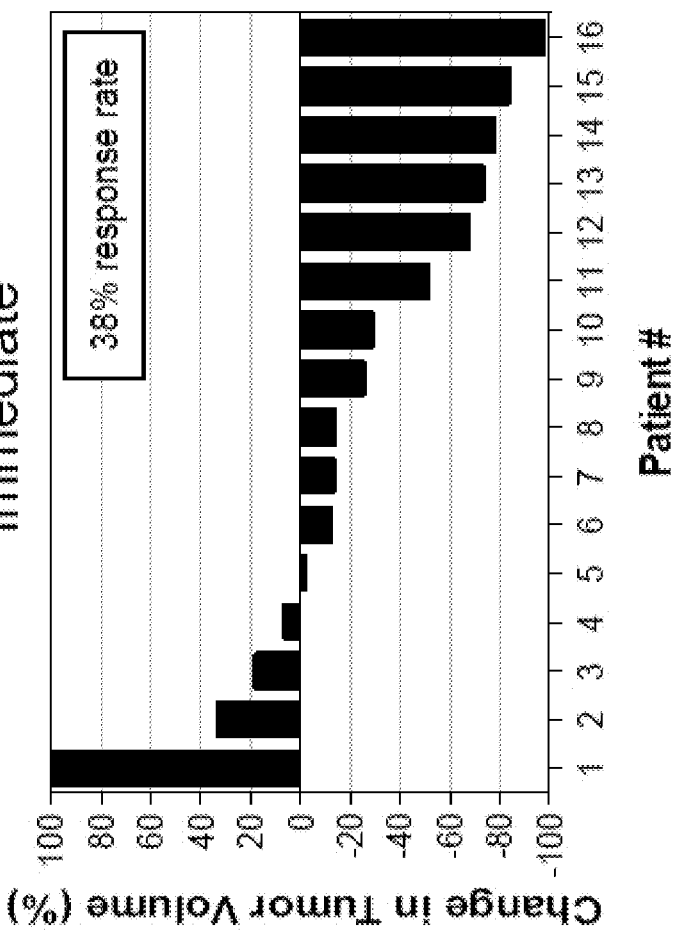

While 38% of patients that received immediate consecutive bevacizumab-gemcitabine delivery exhibited significant tumor response (defined as >30% reduction in tumor volume), the response was not statistically different from the 25% volumetric response observed in the 8-patient placebo control group (FIG. 7C).

However, nearly all patients, 13 of 14 (93%), in the bevacizumab-gemcitabine 1-hour interval schedule cohort had a significantly higher tumor response (FIG. 7D). Volumetric analysis was further performed on the initial post-treatment follow-up scan (after two 3-week treatment cycles). 4 of 16 patients or 25% of those receiving immediate consecutive bevacizumab-gemcitabine delivery exhibited significant tumor response (≥30% reduction in tumor volume), while 9 of 14 (64%), in the bevacizumab-gemcitabine 1-hour interval schedule cohort displayed >30% tumor reduction.

These studies establish that synchronized timing of bevacizumab with gemcitabine, where bevacizumab is delivered 1 hour prior to the administration of gemcitabine, significantly improves tumor response to chemotherapy in patients diagnosed with sarcoma. Overall, clinical outcome of soft tissue sarcoma patients in this trial represents proof-of-principle that ASMase signaling can be engaged for therapeutic benefit. These results also support that ASMase signaling can be established as a biomarker for predicting tumor response and in any event for adjusting timing and dosage of the AAA, optimum timing of the chemotherapeutic drug (relative to the AAA administration) and dosage of the chemotherapeutic drug.

Example 8

Long-Acting Anti-Angiogenic Drugs Render Tumors Refractory to Subsequent Anti-Angiogenic ASMase-Mediated Tumor Sensitization As patients undergo multiple rounds of long-acting anti-angiogenic drug treatments in combination with chemotherapy, there is a progressive increase in the accumulated long-acting anti-angiogenic drug. Thus, the inventors tested whether the first round of long-acting anti-angiogenic drug would impact the response of a second round, delivering full dose of long-acting anti-angiogenic drug in each cycle. Thus, the premise was to evaluate whether a second round of attempted vascular chemosensitization at a time when bevacizumab levels would have decayed to half the level achieved after the first dose, exactly mimicking the first and second rounds of bevacizumab.

Briefly, $1\times10^6$ MCA/129 fibrosarcoma cells were implanted into the right flank of SW129/Bl6$^{JAx}$ mice and tumor volume was measured daily according to the formula described by Kim et. al. (*Cancer Res*, 46, 1120-1123 (1986). Mice were treated with gemcitabine (Gem) at 240 mg/kg i.p. twice at 4 day intervals (black arrows). Certain animals received DC101 (1600 mg/mouse=full dose) at 8 h and/or 1 h before each Gem treatment, as indicated in FIG. 11A. Data (mean±SEM) were collated from 5 mice/group. Another group of animals received either 0 or half of the dose of DC101 at 8 h hours prior to Gem treatment, and full dose of DC101 at 1 hour prior to Gem treatment.

Figure 11B:
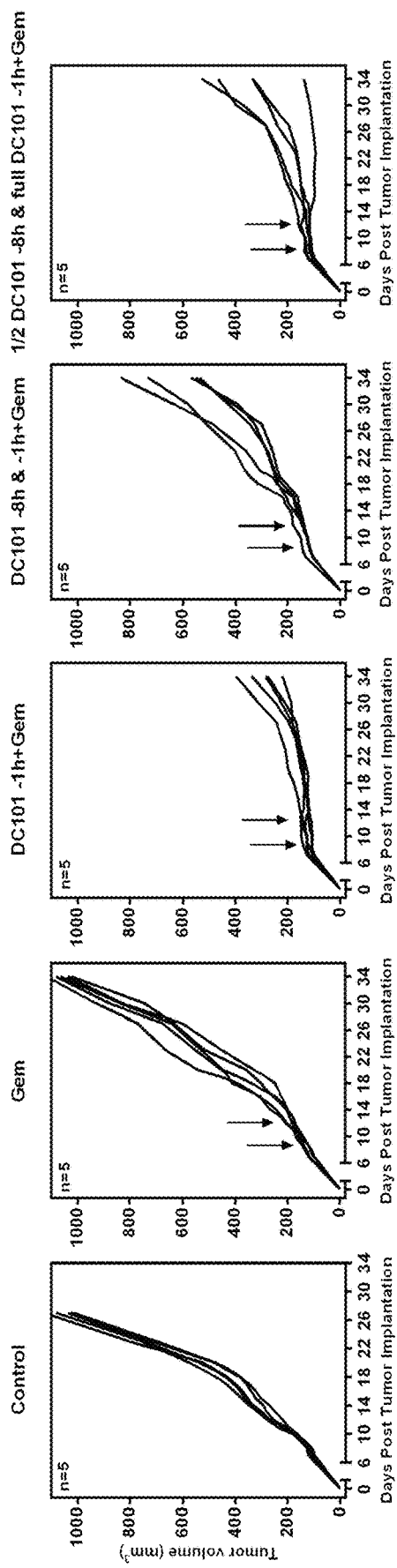
FIG. 11B is a series of plots of MCA/129 fibrosarcoma tumor volume versus days post tumor implantation, where the data depict the individual tumor response profile collated in FIG. 11A.

As shown in FIG. 11A, ASMase-based anti-angiogenic sensitization is attenuated when a full dose of a long-acting anti-angiogenic drug (such as DC101) is already present in the subject at the time of attempted ASMase-based anti-angiogenic chemosensitization. On the contrary, when only half of the DC101 dose (800 mg/mouse) is present in the subject, the impact is minimal, and the inhibitory effect observed with the full dose of DC101 is no longer detected. FIG. 11B shows the individual tumor response profiles as collated in FIG. 11A.

This study mimics the effects of accumulated long-acting anti-angiogenic agents such as bevacizumab, which occur during the successive rounds of multi-cycle clinical trial of a long-acting anti-angiogenic drugs in combination with chemotherapy. For example, at round two of a three-week cycle, there would be half the dose of bevacizumab present in a subject at the time of attempted ASMase-based chemosensitization. Furthermore, at round 4 of a three-week cycle, there would be even higher levels of accumulated long-acting anti-angiogenic drug, where the levels would correspond to approximately 88% of a full dose. At round 5, the levels of accumulated long-acting anti-angiogenic drug would reach approximately 94% of a full dose. These estimates are based on the fact that half-life ($t_{1/2}$) of an IgG, which bevacizumab is one of, is 4 days in mice, and 21 days in humans.

This study provides evidence that long-acting anti-angiogenic agents (drugs) render tumors refractory to subsequent anti-angiogenic ASMase-mediated tumor chemosensitization, where the strength of inhibition intensifies as the amount of long-acting anti-angiogenic agent present in the subject increases. Thus, these experiments support the proposition that short-acting anti-angiogenic drugs with an average half-life of about 120 hours or less are preferred for ASMase/ceramide pathway-based chemosensitization compared to long-acting anti-angiogenics such as bevacizumab or DC101.

Example 9

Kinetics and Dose Dependence of Gemcitabine-Induced ASMase/Ceramide Pathway Activation Pre-clinical models and clinical trial data presented in Examples 1-7 showed that anti-angiogenic agents can substantially improve response of different tumors to different chemotherapy agents that activate ASMase/ceramide pathway, when they are administered using a specific schedule that increases the activity of ASMase/ceramide pathway within the tumor microvasculature. In order to gain a more detailed understanding of principles that govern anti-angiogenic chemosensitization, studies testing the timing and dose dependence of gemcitabine induction of sphingolipid signaling events in A19 BAEC will be performed. 4 different readouts of ASMase/ceramide signaling in BAEC will be determined using standard protocols for these assays: 1) secretory ASMase activity, 2) ceramide generation, and 3) CRM formation within 60 min of gemcitabine administration, and 4) apoptosis at 2-24 h. Zn-dependent secretory ASMase activity will be measured by a radioenzymatic assay that uses [N-methyl-$^{14}$C]sphingomyelin as substrate, under conditions that obey rules of Michaelis-Menten kinetics. When [$^{14}$C]sphingomyelin is hydrolyzed, [$^{14}$C]phosphocholine is released into the aqueous phase of a Folch extraction, which is quantified by scintillation counting (Rotolo et al. *J. Clin. Invest.* 122: 1786-1790, 2012). Cellular ceramide levels will be measured after Bligh and Dyer lipid extraction and analysis via liquid chromatography electrospray tandem mass spectrometry (Kasumov et al. Anal. Biochem. 401:154-161, 2010). CRPs will be detected using confocal microscopy of fixed BAEC cells incubated with anti-ceramide MID 15B4 IgM (Alexis Corporation) (Garzotto et al. Cancer Res. 58: 2260-2264, 1998).

Using a 90% lethal dose ($LD_{90}$) of gemcitabine, the time of maximum activation for each readout will first be determined. Based on prior studies, it is anticipated that ASMase/ceramide/CRP generation will peak within 5-15 min of gemcitabine administration and apoptosis will peak at 6-8 hours. The experimentally determined peak times for each of the 4 events will then be used to generate gemcitabine dose response curves, using a range of effective gemcitabine doses e.g., up to a 100 nM (Laquente et al. *Mol. Cancer Ther.* 2008; 7:638-647. Controls for ASMase specificity will include pharmacologic ASMase inactivation using imipramine (50 μM) and pre-treatment with the raft-disruptor nystatin (30 μg/ml). To delineate the order of early sphingolipid events, anti-ceramide 2A2 antibody, which does not block ASMase activation-ceramide generation, but prevents ceramide coalescence into CRPs and apoptosis, will be used. In order to distinguish between ASMase signaling and de novo ceramide synthesis, the well-defined ceramide synthase inhibitor, Fumonisin B1, will be used (50 Collectively, these experiments will provide detailed information regarding the kinetics of gemcitabine-induced sphingolipid death response in endothelial cells. It is expected that ASMase activity will exhibit a statistically significant increase in response to gemcitabine qualitatively similar to that of FIG. 14C. Furthermore, ceramide levels (C16:0, C18:0) are expected to undergo a statistically significant increase following chemotherapy qualitatively similar to that of FIG. 8. This can be tested as described in Example 20.

Example 10

Determining the Timing of Anti-Angiogenic Administration and Peak of Gemcitabine Sensitization Timing of DC101 and axitinib (selective inhibitor of VEGF receptors 1, 2, and 3) chemosensitization of apoptosis will be optimized in cultured BAEC. Cells will be treated with DC101 (5 μg/ml) or axitinib (50 nM) in a time window encompassing −24 h to +24 h relative to the administration of for example an $LD_{40}$ dose of gemcitabine. After that, the ability of DC101 vs. axitinib to sensitize the dose-response curve for the four readouts will be assessed.

Example 11

Effect of Anti-Angiogenic Agents on a Subsequent Cycle of Chemotherapy

The clinical trial described in Example 7 above as well as preliminary animal data (not shown) prompted the hypothesis that prolonged anti-angiogenesis likely causes ASMase to become refractory to a subsequent round of anti-VEGF and chemotherapy treatment until decay of the anti-angiogenic effect re-sets ASMase sensitivity. For example, in the Example 7 study, the majority of the benefit was achieved after one cycle of AAA+chemotherapy such that the second round of two-modality treatment was either of no additional benefit or minimal additional benefit. See FIGS. 7E and 7F. This hypothesis was confirmed in the experiment of Example 8.

In order to further test the effects of anti-angiogenics on a subsequent cycle of chemotherapy, BAEC will be treated with maximal dose of the long-acting AAA DC101 or the short-acting AAA axitinib, plus $LD_{40}$ gemcitabine, according to the timing information obtained in Example 10. In order to remove endogenous anti-angiogenic agents, culture media will be replaced at varying intervals (6 h to 2 days), after which cells will be re-treated with gemcitabine±DC101 or axitinib. The effects of successive cycles of therapy on all four readouts described in Example 9 will be evaluated. It is anticipated that these studies will determine a minimum time window necessary related to the decay time of the AAA and needed to re-set ASMase sensitivity to anti-angiogenic derepression.

Example 12

Effects of Long-Acting Vs. Short-Acting Anti-Angiogenic on a 2nd Cycle of Chemotherapy Since prolonged anti-angiogenic treatment renders ASMase refractory to a subsequent cycle of anti-VEGF treatment until decline in anti-angiogenic effect re-sets ASMase sensitivity, it is possible that persistence of circulating long-acting anti-angiogenic from treatment cycle 1 will attenuate sphingolipid-based anti-angiogenic chemosensitization in cycle 2. Thus, if this is the case, short-acting angiogenic drugs are likely to be superior for ASMase/ceramide pathway based chemosensitization compared to long-lasting anti-angiogenics such as bevacizumab or DC101.

In vivo experiments using a mouse model of MCA/129 fibrosarcoma will be used to directly assess and compare the impact of both long and short-acting anti-angiogenics on a subsequent round of chemotherapy.

For long-lasting anti-angiogenics, different intervals between the treatment cycles will be tested, where the range evaluated will vary from 0.25-4 DC101 half-lives (1-16 days, half-life 4 days in mice). It is important to note that half-life of IgG in mice is shorter than in humans, 4 days vs. 21 days. Readouts of ASMase/ceramide pathway activity will be determined, as well as the tumor growth response between the two cycles (assessed by standard caliper measurement as per Kim et al. (*Cancer Res,* 46, 1120-1123 (1986). In the initial set of experiments, animals will be treated with gemcitabine for 6 hours prior to the assessment of tumor endothelial apoptosis. Results from these interval timing studies of anti-angiogenic chemosensitization of endothelial apoptosis will be validated by examining full tumor response at 90 days, employing the same DC101 half-life regimen used for endothelial apoptosis, noting complete response and tumor growth delay.

Based on the findings presented in this disclosure, it is anticipated that gemcitabine-induced endothelial apoptosis is going to correlate with tumor responses.

Example 13

ASMase Activity Predicts Tumor Response Outcomes Following High Single Doses of Radiation in the Murine MCA/29 Fibrosarcoma Model Single dose radiotherapy (SDRT) has proven successful in treating cancers previously considered radioresistant. While the exact mechanism of SDRT response has not been completely characterized, it is known that the endothelial cell ASMase/ceramide pathway plays a significant role in mediating this response. Radiation induces rapid endothelial cell ASMase activation, and radiation-induced apoptosis is ASMase-dependent, as mouse endothelium lacking ASMase is resistant to apoptosis. Furthermore, the defect in apoptosis is rescued by addition of exogenous ceramide.

Figure 12A:
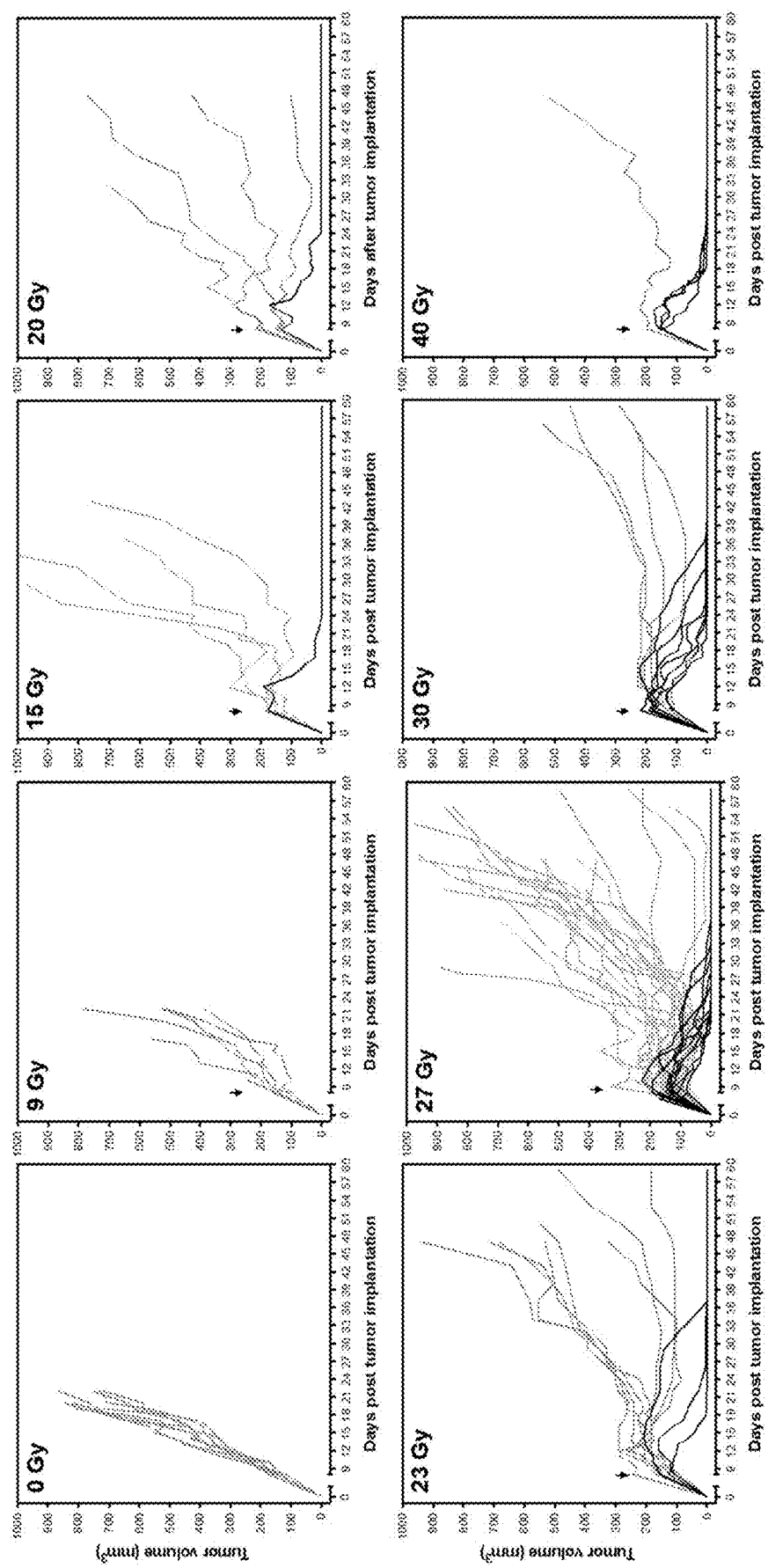
FIG. 12A is a series of graphs showing tumor profiles (tumor volume over days post tumor implantation). Complete responses, defined as no palpable tumor at 30 days post-IR, are summarized in FIG. 12B.

In this Example, the inventors evaluated serum ASMase levels in a MCA/129 fibrosarcoma mouse model in commercial Sv129/BL6 mice following irradiation. As shown in FIGS. 12A and 12B, serum ASMase activity increases in a dose dependent manner following irradiation. Detailed control dose studies determined the 50% tumor control dose ($TCD_{50}$) to be 29.8 Gy+/−0.9 Gy as defined by complete response (no palpable tumor at 30 days post-irradiation). As the time course experiment demonstrated elevations in ASMase at all time points from 1-72 hours post-irradiation, the 24 hour time point was elected for further evaluation. Significant differences in serum ASMase activity elevation at 24 hours post-radiation were observed when 15, 27, and 40 Gy were applied, but no significant changes occurred after 9 Gy (FIG. 12C). Importantly, the SDRT-induced serum ASMase activity increased linearly over the range of 15 to 40 Gy and correlated closely to complete response ($R^2$=0.89, FIG. 12D), suggesting serum ASMase as a potential biomarker of ASMase/ceramide pathway activity in clinical SDRT scenarios.

In the second part of the study, the inventors tested a hypothesis that ASMase/ceramide pathway can be used as a biomarker in SDRT response. Using a uniform dose of 27 Gy, slightly below the $TCD_{50}$ of the MCA/129 model in Sv129/BL6 mice (in an extended cohort of Sv129/BL6 mouse mice (n=19)) the inventors evaluated whether induced serum ASMase activity at 24 hours predicted tumor response at 30 days. In these studies, five mice exhibited complete response, while three additional mice exhibited palpable tumors that did not grow for >15 days following radiation, defined as partial response. The remainder of the cohort continued to grow and were defined as no response. Every mouse exhibited an increase in serum ASMase activity post irradiation, ranging from a 1.1 to 2.7 fold increase (FIG. 13A). However, for tumors that exhibited a complete or partial response to SDRT (light gray and dark grey bars, FIG. 13A), higher fold changes in ASMase activity were observed (FIGS. 13A, 13B), directly linking response to ASMase/ceramide pathway activation.

As shown here, the increase in ASMase serum activity was proportional to SDRT response. This is important as it indicates that targeting factors known to inhibit ASMase, such as angiogenic growth factors (for example VEGF signaling) would lead to further increase in ASMase, which in turn would result in an enhanced response to SDRT. Thus, use of anti-angiogenic agents (shortly before SDRT treatment) capable of further increasing and/or activating ASMase during the SDRT treatment is highly desirable. In order to achieve even greater ASMase activation, it would be attractive to use a higher dosage of anti-angiogenic agent which has also been shown here to increase ASMase activity during a short-duration window (especially since the other therapeutic modality, SDRT or chemotherapy, is often administered at or near the maximum tolerated dose). For example, the maximal ASMase increasing dose of the AAA (subject to any dose-limiting toxicity) can be assessed and administered. It is anticipated that this will be substantially higher than the low daily dose formulations currently available.

Accordingly, increase of ASMase activity as much as feasible without inducing toxicity in the treated subject emerges as a goal of treatment optimization, by dosage adjustment of ASMase stimulating agents, whether it be the AAA or the SDRT or the chemotherapy modality or both.

It emerges from the foregoing data that activation of the ASMase pathway which leads to ischemia reperfusion injury and permits tumor regression and subject survival is common to both HDRT and chemotherapy. The ability of AAA to attenuate ASMase and therefore attenuate the intensity of ischemia reperfusion, except if given at the appropriate time relative to the second modality, is also established. Accordingly, results described herein regarding ASMase activation and ischemia reperfusion intensity are applicable to either combination: AAA+SDRT or AAA+chemotherapy Example 14

Single Dose Radiotherapy Induces Microvascular Vasoconstriction in Animal Models Recent studies have shown that anti-angiogenic drugs can de-repress ASMase/ceramide pathway to enhance ceramide-mediated endothelial apoptosis, but only if delivered prior but close to the time of SDRT, e.g., an hour and in any event less than two hours before SDRT (Rao et al. *Radiotherapy and oncology: journal of the European Society for Therapeutic Radiology and Oncology* 111, 88-93, 2014). In animal models, xenograft responses to SDRT combined with anti-angiogenic treatment are significantly attenuated when tumors are implanted in $asm^{-/-}$ mice. Similar effects are observed when $asm^{+/+}$ mice bearing xenografts are pre-treated with an inhibitory anti-ceramide antibody. These results indicate that host endothelium is an important component of SDRT-induced tumor responses combined with direct effects of radiation on tumor cells.

Single dose radiotherapy (SDRT) has proven successful in treating cancers previously considered radioresistant. While the exact mechanism of SDRT response has not been completely characterized, it is known that the endothelial cell ASMase/ceramide pathway plays a significant role in mediating this response. Radiation induces rapid endothelial cell ASMase activation, and radiation-induced apoptosis is ASMase dependent, as endothelium of mice lacking ASMase is resistant to apoptosis. Furthermore, the defect in apoptosis is rescued by addition of exogenous ceramide.

Recent studies have shown that anti-angiogenic drugs can de-repress ASMase/ceramide pathway to enhance ceramide-mediated endothelial apoptosis, but only if delivered prior but close to the time of SDRT, e.g., an hour and in any event less than two hours before SDRT (Rao et al. *Radiotherapy and oncology: journal of the European Society for Therapeutic Radiology and Oncology* 111, 88-93, 2014). In animal models, xenograft responses to SDRT combined with anti-angiogenic treatment are significantly attenuated when tumors are implanted in $ASMase^{-/-}$ mice. Similar effects are observed when $asmase^{+/+}$ mice bearing xenografts were pre-treated with an inhibitory anti-ceramide antibody (data not shown). These results indicate that host endothelium is an important component of SDRT-induced tumor responses combined with direct effects of radiation on tumor cells. To gain a better understanding of the biological processes that govern vascular dysfunction caused by SDRT, it was postulated that ASMase/ceramide pathway mediates microvascular vasoconstriction as an acute injury response on a pathway to apoptotic death. Thus, tumor microvascular vasoconstriction (measured, e.g., by perfusion alterations) was evaluated following different doses of SDRT.

SDRT induced vascular dysfunction was assessed by in situ tumor perfusion measurements using DCE-MRI with Gd-DTPA (Cho et al. Neoplasia 11, 247-259, 2009). Tissue perfusion was calculated according to a model developed by Hoffmann et al. (Hoffmann et al. *Society of Magnetic Resonance in Medicine* 33, 506-514, 1995). Akep values of the whole tumor sections were determined, wherein a decrease in Akep values was indicative of perfusion reduction and hence tumor hypoxia or ischemia. A short time (30 min) after radiation, tumor samples (two different tumor types were tested) from the asm$^{+/+}$ host displayed significant perfusion reduction, while no reduction was detected in the sample from the asm−/− host. Similar perfusion dysfunction was not detected in the asm−/− host. Timing of ASMase-regulated vasoconstriction was quantified in the MCa allogeneic breast cancer model, wherein perfusion was decreased at 30 minutes and 100 minutes post-SDRT. The results were confirmed by measuring tumor capillary perfusion which significantly decreased within a short time (30 min) after SDRT in asm$^{+/+}$ mice while it was not changed in asm$^{-/-}$ mice. (Data not shown.) Electron paramagnetic resonance (EPR) spectroscopic 02 levels, showed 29% reduction in B16 melanoma $O_2$ tension post 20 Gy SDRT of tumors in asmase$^{+/+}$ mice, abrogated in asmase−/− littermates.

Collectively, these results suggest acute perfusion deficits accompanied by 02 decrements after SDRT. These observations put forward a plausible mechanism by which ASMase-mediated endothelial dysfunction determines tumor response, in which apoptosis per se does not account for tumor response; rather ASMase-mediated acute vascular dysfunction distinguishes SDRT from conventional fractionated radiotherapy. These observations can be extrapolated to chemotherapy as ASMase is also increased in response to chemotherapy.

Example 15

Microvascular Vasoconstriction Occurs within 1-2 Hours Following 24 Gy Single Dose Radiotherapy Vascular dysfunction in patients with metastatic disease was assessed using a non-invasive imaging technique known as intravoxel incoherent motion (IVIM) diffusion-weighted magnetic resonance imaging (IVIM DW-MRI). In biologic tissues, microscopic motion detected by standard DW-MRI includes (i) diffusion of water molecules, influenced by structural components of tissue, and (ii) microcirculation of blood in the capillary network (perfusion). In tissues characterized by high cellular density, such as tumors, motion of water molecules is more constrained than in normal tissues.

Figure 9D:
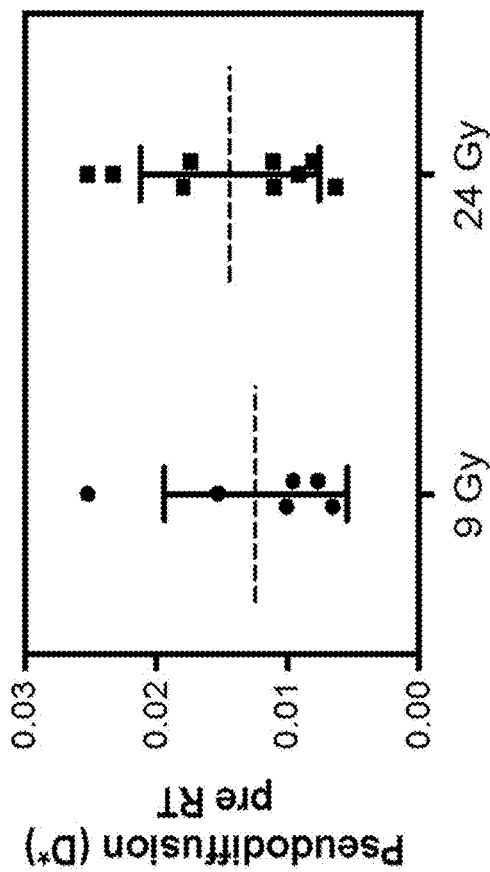
Figure 9C:
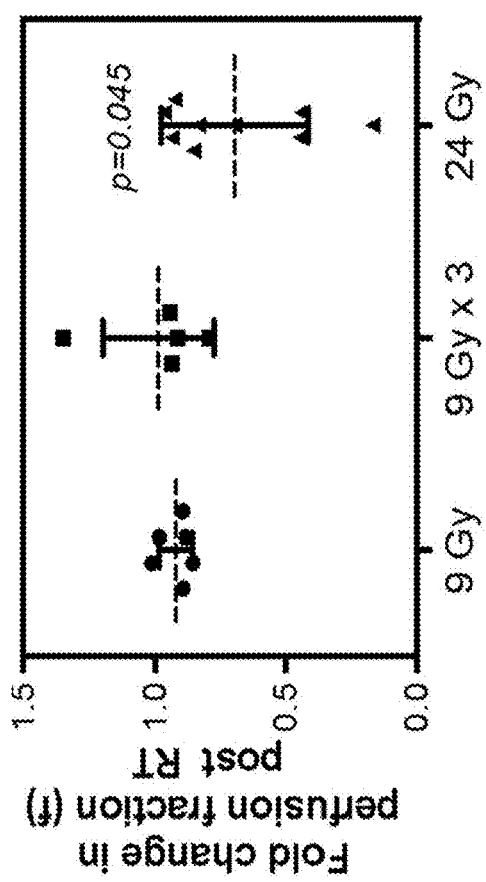
FIG. 9C and FIG. 9E are dot plots showing fold changes in f and D* after RT. Each point represents one patient with value expressed as the f or D* value as a fraction of that patient's pre-radiation value. Up to 16 repeated measurements of D* and f were used to determine the pre- and post-SDRT values. Mean and standard deviations of the 9 Gy and 24 Gy cohorts are shown. Two-tailed, unpaired t tests with Welch's correction were used in FIGs D and E.
Figure 9E:
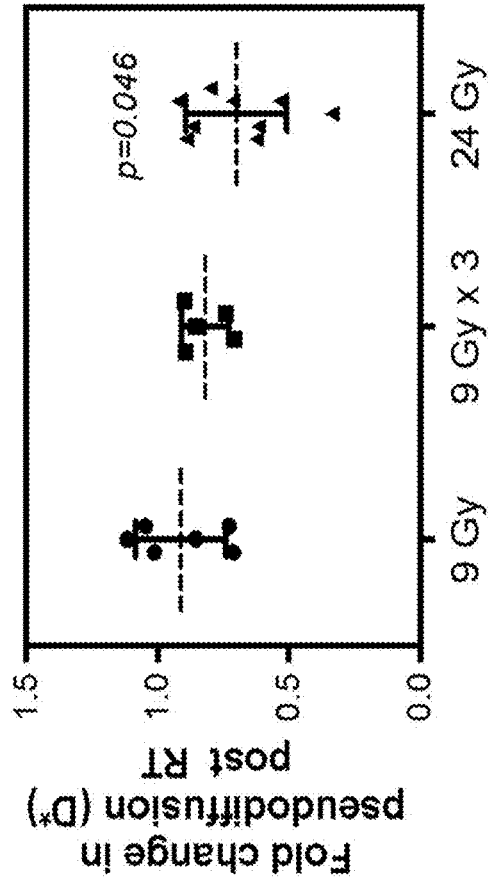

IVIM-DW-MRI allows for acquisition of multiple measurements over a short time period. In IVIM DW-MRI, multiple b-values are applied, reflecting different strengths and timing of the diffusion gradient. The relationship between the MR signal intensity (S) within a tumor at different b values exhibits a bi-exponential pattern with a steep slope at low b-values and a shallower slope at higher b-values. The steepness of the initial curve at low b-values reflects the effect of microvascular events on diffusion. The initial slope of the curve represents an estimate of flow velocity (pseudodiffusion, $D^*$) within the microvasculature and 1 minus the Y-intercept of the later portion of the curve represents the perfusion fraction (f), i.e. the volume of blood within the microvasculature. Thus, both parameters provide related measures of microvascular function. In 15 patients (10 of whom also elected to participate in the serum collection), IVIM DW-MRI was performed before radiation and repeated within 0.5-2 hours following radiation, a time frame selected based on the pre-clinical data that demonstrates ASMase-dependent reduction in perfusion at 0.5-2 hours following SDRT. The IVIM image was acquired at several consecutive time points with 4 min intervals between acquisitions. An experienced radiologist placed a volume of interest (VOI) on the irradiated lesion on the IVIM DW-MRI images, using anatomic (T1- and T2-weighted) MRI sequences as a reference (FIG. 9A). $D^*$ and f values were calculated within each pixel of the VOI and averaged to produce a mean tumor $D^*$ and f. Up to 16 repeated mean tumor $D^*$ and f measurements were obtained pre- and post-SDRT. The pre-radiation IVIM-DW MRI $D^*$ and f values exhibited considerable heterogeneity between tumors, reflecting differing baseline tumor microvascular perfusion (FIGS. 9B and 9C). To compare changes in microvascular perfusion, mean tumor $D^*$ and f are expressed as a fraction of the each tumor's pre-SDRT mean tumor $D^*$ and f (FIGS. 9D, 9E). In the 9 patients receiving 24 Gy SDRT, there was significant decrease in IVIM parameters f (mean−30%) and $D^*$ (mean−24%). In contrast, in the 6 patients that underwent IVIM imaging before and after 9 Gy, mean $D^*$ and f were not substantially changed. These results suggest MRI detectable perfusion deficits may serve to biomark the tumor biology of SDRT.

These findings could be expanded to include more doses, which would then allow for the establishment of minimum and maximum doses of SDRT that induce tumor microvascular vasoconstriction.

Example 16

Increased ASMase Activity is Detected in Serum of Patients 1-2 Hours Following 24 Gy SDRT Recent studies have shown that anti-angiogenic drugs can de-repress ASMase/ceramide pathway to enhance ceramide-mediated endothelial apoptosis when delivered 1-2 hours before SDRT (Rao et al. *Radiotherapy and oncology: journal of the European Society for Therapeutic Radiology and Oncology* 111, 88-93, 2014). As the data presented here indicate that SDRT leads to microvascular vasoconstriction after 24 Gy, ASMase was measured following SDRT.

Figure 10B:
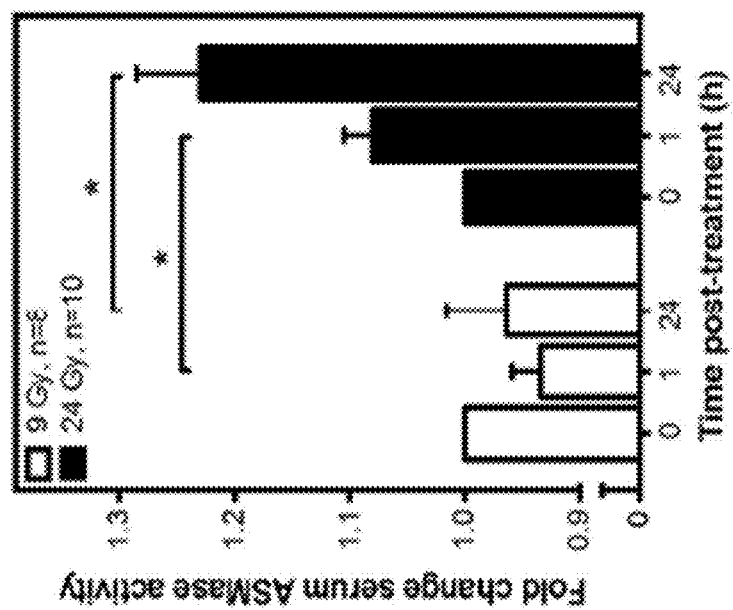
FIG. 10B is a bar graph showing mean fold changes in serum ASMase activity in the two patient cohorts. Two tailed, unpaired t tests in B. *P<0.05.
Figure 10A:
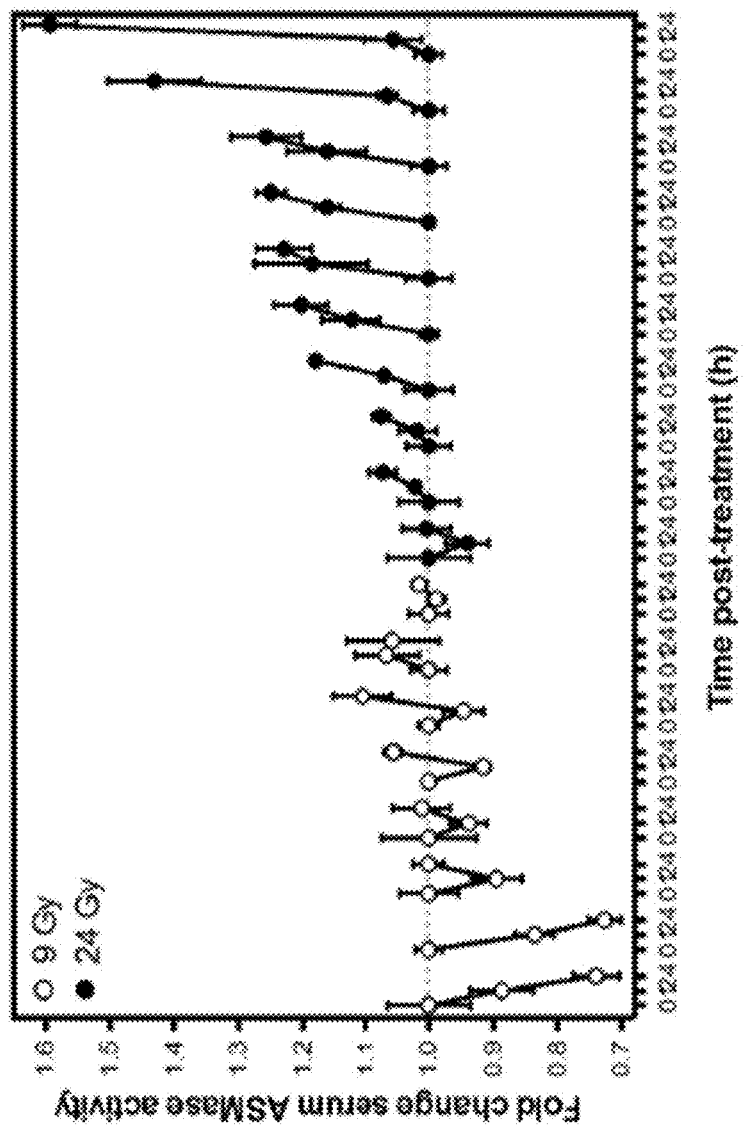
FIG. 10A is a graph showing normalized fold changes in ASMase activity 24 hours after 9 or 24 Gy. Three data points are represented for each patient: 0(pre-RT), 1 hour and 24 hours post RT. Error bars represent the standard error of 3 technical replicates of ASMase measurements for each sample.

Several dose and fractionation schemes are used in clinical treatment of bone metastases to the spine. Common regimens include single doses of 16-24 Gy and hypofractionated regimens such as 9 Gy×3 fractions. It is not known whether one regimen is superior to another in terms of local tumor control. This question is the focus of an ongoing multi-institutional randomized trial (NCT01223248) comparing 24 Gy×1 fraction to 9 Gy×3 fractions for patients with bone metastases of any solid tumor histology with the primary endpoint of local control. In a subset of patients from this trial who consented to a nested biomarker study, serum samples were collected before, and at 1 and 24 hours following radiation treatment. For the 9 Gy×3 arm, serum was collected after the first 9 Gy radiation dose. This strategy allowed for direct testing of the hypothesis, developed pre-clinically, that there is a dose threshold for activation of the ASMase/ceramide pathway. In the 18 patients accrued to the biomarker substudy, 10 were accrued within the 24 Gy cohort and 8 within the 9 Gy×3 cohort (FIG. 10C). As hypothesized, there was an elevation in serum ASMase activity following 24 Gy, but no change following 9 Gy (FIGS. 10A, 10B). Seven of 10 patients in the 24 Gy group exhibited increases in ASMase activity (1.2 to 1.5 fold increases, FIG. 10A). Elevations were most prominent and consistent at the 24 hour time point (FIG. 10B), but nonetheless mean values were elevated at both 1 and 24 hours post-SDRT, consistent with our observations in the MCa/129 murine fibrosarcoma model.

To examine whether an induced serum ASMase activity increase might occur after the total cumulative radiation dose reached a specific threshold in the range of 24 Gy, we examined ASMase activity levels in 5 patient samples at 1 and 24 hours following the $3^{rd}$ fraction of 9 Gy (cumulative dose of 27 Gy). No significant ASMase serum changes were seen above baseline at 1 hour (mean 1.04±0.06 fold change) or at 24 hours (mean 1.02±0.07 fold change) after the third dose of 9 Gy. These studies provide strong support for the hypothesis that rapid release of ASMase into the circulation can biomark the biologic impact of SDRT in patients.

Thus, measured ASMase activity may constitute an alternative to IVIM DW-MRI as a biomarker of SDRT clinical response.

Example 17

Microvascular Vasoconstriction Occurs Immediately Following Administration of a Chemotherapeutic Agent Activating ASMase Signaling in Animal Model Based on the results described in Example 14, wherein the activation of the ASMase/ceramide pathway by radiotherapy mediates vasoconstriction and given the results of Example 14, it was postulated that vasoconstriction and ensuing vascular perfusion defects also occur following administration of chemotherapeutic agents that activate the same pathway. In order to confirm this, vascular dysfunction was assessed by measuring perfusion/permeability as described in Example 14.

Briefly, MCA/129 fibrosarcoma tumors were implanted in the rear mouse hip, and subjected to intravoxel incoherent motion (IVIM) MRI when tumors reached a size of 150-300 $mm^3$. After i.p. injection of gemcitabine (240 mg/kg) both vascularity (Fp, FIG. 14A) and diffusion (D*, FIG. 14B) were reduced in a reversible manner over a 1 hour time period, where the peak of vascularity and diffusion reduction was observed between 15-30 minutes following the treatment with gemcitabine (p<0.05, Bonferroni correction applied). Data (mean±SEM) are collated from 6 animals per group.

Figure 14C:
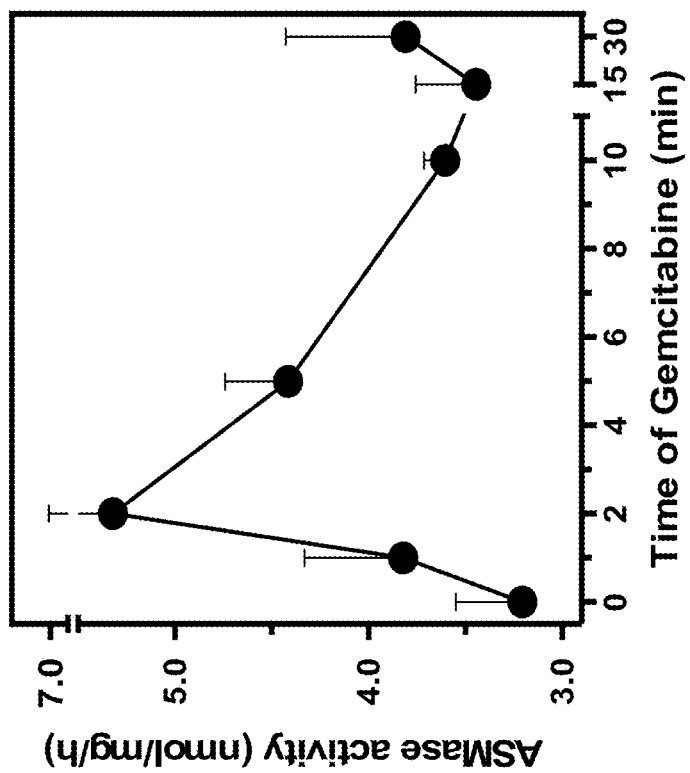
FIG. 14C is a graph of ASMase activity over time following the treatment of cultured bovine aortic endothelial cells with 100 nM gemcitabine.

Gemcitabine was able to activate ASMase in cultured endothelial cells. The experiment was conducted in order to study the time-course of ASMase activity after addition of 100 nM gemcitabine to bovine aortic endothelial cells. As shown in FIG. 14C, gemcitabine triggered rapid cellular activation of ASMase. Furthermore, the activation of ASMase occurred in a dose-dependent manner as evident in FIG. 14D, which represents a dose-response curve of ASMase activation at 5 minutes. ASMase activity was determined on total cell lysates. Data (mean±SEM) are collated from 3 separate experiments.

The fact that ASMase activation occurs in a dose-dependent manner as shown in FIG. 14D is of importance, as it suggests that higher doses of chemotherapy drugs might be needed in order to take full advantage of ASMase-mediated chemosensitization. Further studies are needed in order to determine the optimal dose required and feasible.

Example 18

Establishing Vasoconstriction Immediately Following Administration of a Chemotherapeutic Agent Activating ASMase Signaling in Asmase$^{-/-}$ Animals Given the findings that microvascular vasoconstriction occurs immediately following administration of a chemotherapeutic agent (FIGS. 14A and 14B) the following study will confirm the role of ASMase signaling in an additional animal model using asmase$^{-/-}$ animals.

MCA/129 fibrosarcoma and B16 melanoma tumor models will be generated in asmase$^{+/+}$ or asmase$^{-/-}$ animals, followed by the treatment of mice with X (e.g., 1, 2, 3) doses of various chemotherapeutic agents that activate ASMase/ceramide signaling, such as paclitaxel, etoposide, and/or gemcitabine. Blood perfusion/permeability in tumor tissue will be determined at time intervals immediately prior to and within 0.5-24 hours following injection of a bolus of chemotherapeutic agent. Perfusion reduction following the administration of chemotherapeutic agent in tumors implanted in asmase$^{+/+}$ but not asmase$^{-/-}$ animals will confirm that activation of the ASMase-ceramide pathway mediates microvascular vasoconstriction-dysfunction and therefore interferes with the ability of the tumor to recover from the direct cytotoxic effects of the therapeutic agent.

In addition to MM detection, chemotherapy-induced perfusion defects will be characterized using Hoecht Dye Extravasation (Chaplin et al. Cancer Research, 47, 597-601, 1987). Briefly, Hoecht 33342 will be injected via tail vein into asmase$^{+/+}$ or asmas$^{-/-}$ mice bearing MCA/129 fibrosarcomas and B16 melanomas following the treatment with chemotherapy. Mean fluorescence of tumor sections will be used as a measurement of tumor capillary perfusion. Measurements will be taken at various time-points post chemotherapy treatment.

Vascular perfusion will be determined using a third technology, where electron paramagnetic resonance (EPR) spectroscopic $O_2$ levels will be quantified by direct imaging of tumors in vivo (Epel et a. Concepts in magnetic resonance. Part B, Magnetic resonance engineering 33B, 163-176, 2008).

Collectively, these studies will provide detailed information regarding the timing and dosage of chemotherapy and corresponding vasoconstriction, as well as the involvement of the ASMase-ceramide pathway in this process. It is anticipated that these experiments will confirm that this pathway (through direct or indirect measurement (or derivation) of ASMase, sphingolipid, or ceramide) will provide important biomarkers of chemotherapy effectiveness.

Example 19

Testing Whether IVIM Diffusion-Weighted MRI can Quantitatively Assess Tumor Vascular Dysfunction Immediately after Chemotherapy and Serve as a Biomarker to Predict Tumor Response Clinical trial data presented in Example 7 underscore the importance of timing the administration of an anti-angiogenic agent with that of a chemotherapeutic agent that activates the ASMase-ceramide pathway in order to improve tumor response in patients. As disclosed herein, anti-angiogenic agent administration should be timed as to result in ASMase-ceramide pathway activation. It is hypothesized that in addition to mediating endothelial cell apoptosis, ASMase-ceramide-signaling may govern acute vascular dysfunction leading to rapid reduction in tumor perfusion followed by re-perfusion. This hypothesis was initially tested in animal models as described above in Example 17 and Example 18. Next, the occurrence of vascular dysfunction following timed anti-angiogenic and chemotherapy treatment in patients will be investigated.

Vascular dysfunction will be assessed using dynamic IVIM diffusion-weighted magnetic resonance imaging (IVIM DW-MRI). In biologic tissues, microscopic motion detected by standard DW-MRI includes (i) diffusion of water molecules, influenced by structural components of tissue, and (ii) microcirculation of blood in the capillary network (perfusion). In tissues characterized by high cellular density, such as tumors, motion of water molecules is more constrained than in normal tissues. One of the important advantages of IVIM DW-MRI is that it allows repeated "dynamic" measurement of perfusion and diffusion-related surrogate metrics every few minutes, without the need for intravenous contrast agent. While standard DW-MRI is typically performed using a single-shot spin-echo echo planar imaging (SE-EPI), a modified method will be used in these studies. A technique will be adapted as to allow for (i) acquisition of multiple contiguous 2D slices, (ii) multiple b-values, and (iii) data censorship and off-line averaging. Since IVIM parameters can be measured many times over a short period of time (45-60 minutes), IVIM DW-MRI can be used to obtained detailed kinetics of tumor vascular dysfunction following the administration of chemotherapy. While other alternatives, such as dynamic contrast-enhanced (DCE)-MRI or $^{51}$O-PET could also be used to assess tissue vascularity, these methods are not suitable for the purposes of the proposed study, as they cannot be re-injected into a patient to serially monitor changes in vascularity over time.

Patients treated for metastatic disease to bone or soft tissue at MSKCC will be recruited for the study. The following inclusion criteria will be used: (i) histologically proven metastatic disease; (ii) patients deemed clinically appropriate for chemotherapy treatment; (iii) life expectancy >6 months; (iv) age >18 years. Exclusion criteria: (i) unable to give informed consent; (ii) unable to comply with the protocol, (iii) MRI is contraindicated; (iv) tumors involving visceral organs, brain or spinal cord; (v) platelet count <75,000/µl, HgB level <9 g/dl, WBC <3500/µl; (vi) metastases in the upper thoracic spine (to avoid MM artifacts due to cardiac motion); (vii) lesions <1.5 cm (to ensure robust measurements). Currently, patients with bone and soft tissue metastases receive intravenous gemcitabine over a 90 minute period.

IVIM DW-MRI will be repeated 16 times following the intravenous administration of 900 mg/m$^2$ of gemcitabine, or 75 mg/m$^2$ docetaxel where images will be acquired at various time points, including 60, 90, 120, and 150 minutes following chemotherapy treatment.

Perfusion fraction, pseudo-diffusion coefficient, and diffusion coefficient will be calculated for each lesion, using a biexponential signal decay model and incorporating a correction to account for differences in the T1 and T2 relaxation times of tissue and blood, respectively (Lemke et al. Magnetic resonance in medicine: official journal of the Society of Magnetic Resonance in Medicine, 64, 1580-1585, 2010). For patients in each drug (gemcitabine or docetaxel) category, post-treatment measurements (expressed as fractions of the pre-treatment values) will be summarized and the nadir value/time point will be determined using time series plots. To test whether measurements at any particular time point are significantly lower than 1, one-sample, one-sided t-tests will be used. To test whether measurements at one time point are significantly lower than those at another time point (applicable for statistically confirming the nadir point), one-sided pair-wise t-tests will be used.

The resulting detailed understanding of the kinetics of chemotherapy-induced vascular injury will be used to develop an imaging biomarker that will be used to optimize the doses and timing of anti-angiogenics and chemotherapy. It is expected that IVIM parameters f and D*, which represent blood volume fraction and microcirculatory perfusion of blood within capillaries, respectively, will be changed following chemotherapy. The changed values are expected to fall into the following ranges: 1) 30-50% reduction in blood volume fraction (f) (for example, 40%); and 2) 15-35% reduction in microcirculatory perfusion of blood within capillaries (D*) (for example, 25%).

Example 20

Testing Whether ASMase Activity and Quantity of Ceramide Species Immediately Following Chemotherapy can Serve as a Biomarker and Predict Tumor Response to Chemotherapy Findings disclosed herein suggest that activation of ASMase signaling as well as generation of pro-apoptotic C16:0 and C18:0 ceramide may serve as biomarkers that can be used for chemotherapy schedule and dose optimization, in combination with ASMase/ceramide sensitizing anti-angiogenic agents. The secretory form of ASMase, released in response to various chemotherapy agents, can be detected in human serum. In addition to ASMase, C16:0 or C18:0 ceramide can also be measured using human serum by mass spectroscopy (MS).

Figure 8:
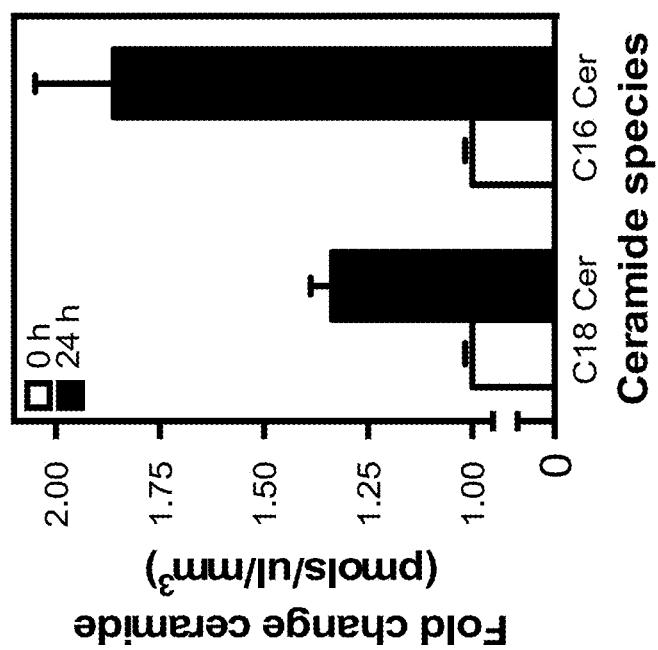
FIG. 8 is a bar graph of fold change in serum ceramide (C16:0 and C18:0) levels in MCA129 fibrosarcoma tumor allografts treated with 27 Gy IR at 24 hours post-irradiation (24 h).

The inventors have already conducted animal studies regarding the serum ceramide levels following irradiation. MCA129 fibrosarcoma tumor allografts (tumor size ~150 mm3) were treated with 27 Gy IR. Mice were bled 24 h pre-irradiation (0 h) and 24 h post-irradiation (24 h) and serum harvested for MS analysis. As shown in FIG. 8, both C16:0 and C18:0 ceramide species were elevated in response to irradiation. On the contrary, serum levels of anti-apoptotic ceramide C24:0 remained unchanged following irradiation.

Given the similarities between ASMase activity increase in response to irradiation and ASMase activity increase in response to chemotherapy, it is anticipated that both pro-apoptotic C16:0 and C18:0 ceramide levels will be increased in serum of animals and/or patients following treatment with chemotherapy agents.

In order to confirm that ASMase/ceramide pathway can serve as a biomarker in a clinical setting, patients undergoing IVIM DW-MRI studies described in Example 19 will have serum samples collected 1 hour prior and 24 hours after chemotherapy treatment.

8-10 ml of whole blood from each patient enrolled in the study will be collected into glass, anti-coagulant-free tubes and allowed to clot 20-30 minutes. Following centrifugation of the sample at 1200 g, the serum supernatant will be stored under $N_2$ gas in 5×5000_, and 5×50 µL aliquots. ASMase activity will be assessed using 10 µL of serum with C14-labeled sphingomyelin as substrate. ASMase-mediated sphingomyelin hydrolysis leads to release of C14-labeled phosphocholine, which can be extracted into an aqueous phase and quantified by scintillation counting. Furthermore, ceramide MS will be performed to assess both pro-apoptotic (C16:0, C18:0) and anti-apototic ceramide species (C24:0).

It is anticipated that chemotherapy agents will cause a statistically significant increase in ASMase levels and/or activity. Similarly, proapoptotic ceramide levels (C16:0, C18:0) are expected to show a statistically significant increase following chemotherapy.

Example 21

Clinical Trial for Dose Escalation of a Short-Acting Anti-Angiogenic Agent for Optimum Enhanced Chemosensitivity A phase IB will be pursued in standard 3+3 format. As such, the first 3 patients accrued to the trial will be treated at dose level 1 as provided in the table below. Patients will be monitored for dose-limiting toxicity as well as for ASMase activation, acute effect of anti-angiogenic agent on tumor vascularity measured for example by IVIM DW-MRI and of course tumor response measured for example by conventional MIll with contrast agent. ASMase levels will be measured by standardized radioenzymatic assay using [14C]sphingomyelin as substrate as per Rao et al. (*Radiotherapy and oncology: journal of the European Society for Therapeutic Radiology and Oncology* 111, 88-93, 2014) or alternatively by measuring ceramide species, as described for example in Merrill, A. H., Jr. (2011). Chem. Rev. 111, 6387-642. This clinical study will be generally based on Rugo, H. S. et al, J. Clin. Oncol, 23(24): Aug. 20, 2005.

If none of these patients experience a dose-limiting toxicity (DLT) after the first three cycles of treatment, the dose of AAA will be raised to dose level 2. If 2 out of 3 patients experiences DLT, the dose level will be reduced and 3 new patients will be accrued at dose level −1. If 1 out of 3 patients experiences toxicity on dose level 1, a further 3 patients will be accrued to this level. If <2/6 patients on dose level 1 experiences dose-limiting toxicity (DLT) the dose will be raised to dose level 2, as described below. If 2/6 patients on dose level 1 experiences DLT, the dose level will be reduced and 3 patients will be accrued at dose level −1. If 0/3 patients on dose level −1 then experiences DLT, this level would then be considered MTD. If 1/3 patients experiences DLT, the dose level will be expanded to a total of 6 patients. If <3/6 patients have DLT at this level, it will be considered the MTD. If >2 patients have DLT at dose level −1, the treatment combination will be considered unfeasible and further development of this combination will be stopped. Conversely, if at dose level 2 there is no DLT in the first 3 patients (or <2 out of 6 patients), the dose will be increased to dose level 3. If toxicity is seen in >2 of the first 6 patients treated at this dose 2, dose level 1 would be considered the MTD. If 0/3 or <2/6 patients treated at dose level 2 has DLT, this will be considered the MTD. At the same time, ASMase increase will be monitored. Doses will continue to be escalated until the maximal ASMase activity level is reached immediately following AAA administration, provided of course that DLT has not been reached.

The purpose of the ASMase measurements will be to assess whether any additional anti-angiogenic agent will result in an incremental increase in ASMase levels (or an incremental increase in ceramide species levels). If no additional ASMase is expressed with a higher AAA dose, there is no reason to increase the AAA dose even if DLT has not been reached. If DLT is reached at a dose lower than the maximum ASMase increase dose, the dose dictated by DLT may be expected to be adopted.

ASMase measurements will continue to be taken to assess response to the AAA, i.e., to ensure that the administration of the chemotherapeutic agent will be to confirm that chemotherapy in each cycle will be administered during the de-repressed ASMase interval or window and to confirm that the AAA from the prior cycle will have decayed before administration of another dose of AAA (and chemotherapy).

Each of the accrued patients will have serum samples collected 1 hour before and 24 hours after the first chemotherapy treatment. For each patient, 8-10 ml of whole blood will be collected into glass, anti-coagulant-free tubes and allowed to clot 20-30 minutes. Blood will be centrifuged at 1200 g and the serum supernatant stored under N2 gas in 5×500 uL and 5×50 uL aliquots. ASMase activity assays are performed with 10 μL of serum with C14-labeled sphingomyelin as substrate. ASMase hydrolyzes sphingomyelin, releasing C14-labeled phosphocholine that can be extracted into an aqueous phase and quantified by scintillation counting. Ceramide mass spectrometry (MS) will be performed using already established protocols (Merrill, A. H., Jr. (2011). Chem. Rev. 111, 6387-6422) to assess pro-apoptotic (C16:0, C18:0) and anti-apoptotic ceramide species (C24:0).

Similarly the purpose of IVIM DW-MRI which allows repeated "dynamic" measurement of perfusion and diffusion-related surrogate metrics every few minutes, without the need for intravenous contrast is to assess tumor vascular dysfunction immediately upon administration of the AAA and chemotherapy. Based on preliminary data from SDRT, vascular volume fraction and vascular flow are reduced following treatment with combined AAA and SDRT. It is anticipated that similar results will obtain following the timed administration of AAA followed by chemotherapy in accordance with the present disclosure. See for example Bisdas, S. et al. *Correlative assessment of tumor microcirculation using contrast-enhanced perfusion MRI and intravoxel incoherent motion diffusion-weighted MRI: is there a link between them?* NMR in Biomedicine 27, 1184-1191, doi:10.1002/nbm.3172 (2014).

Microcirculatory perfusion of blood within capillaries has no specific orientation and can be thought of as "pseudo-diffusion," which depends on the velocity of the flowing blood and the vascular architecture. The IVIM approach assumes that the measured MR signal attenuation comprises a mixture of tissue perfusion and tissue diffusivity. These effects are characterized by using a bi-exponential function to model the MR signal decay as a function of b-value instead of a mono-exponential decay. Acquiring IVIM images over an entire tumor takes 2-3 minutes and allows calculation of quantitative indexes which describe tissue water diffusivity (D), tissue perfusion (pseudo-diffusion coefficient—D*), and vascular volume fraction (f). The ability of IVIM to non-invasively quantify "perfusion" (IVIM parameters D* and f) is central to the concept of detecting of acute chemotherapy-induced (or combined AAA- and chemotherapy-induced) vascular dysfunction.

IVIM DW-MRI will be obtained at baseline and at various time points to assess response to the AAA, i.e., to ensure that the administration of the chemotherapeutic agent will be to confirm that chemotherapy in each cycle will be administered during the de-repressed ASMase interval or window and to confirm that the AAA from the prior cycle will have decayed before administration of another dose of AAA (and chemotherapy).

Dose Limiting Toxicity (DLT) is defined as the occurrence of Grade 4 hematologic toxicity, Grade 3 or 4 non-hematologic toxicity including diarrhea (despite use of antidiarrheal prophylaxis or glucocorticoids), or nausea and vomiting (despite use of maximal anti-emetics).

TABLE

| Dose Level | Axitinib (day 1, 1 hr before gemcitabine) | Gemcitabine | Docetaxel |
| --- | --- | --- | --- |
| Phase IB dose levels | | | |
| Level −1 | 5 mg PO | 900 mg/m$^2$ IV days 1, 8 | 75 mg/m$^2$ IV day 8 |
| Level 1 | 10 mg PO | 900 mg/m$^2$ IV days 1, 8 | 75 mg/m$^2$ IV day 8 |
| Level 2 | 20 mg PO | 900 mg/m$^2$ IV days 1, 8 | 75 mg/m$^2$ IV day 8 |
| Level 3 | 30 mg PO | 900 mg/m$^2$ IV days 1, 8 | 75 mg/m$^2$ IV day 8 |

The materials methods and measurements described herein are not limiting and the same assessments can be made using alternative techniques known in the art. Similarly, the quantities of AAA and chemotherapeutic agents used are not limiting and may be subject to adjustment in accordance with the skill in the art or as dictated by the biomarkers disclosed herein. All cited references are incorporated by reference in their entirety.

The invention claimed is:

1. A method for increasing the efficacy of a chemotherapeutic agent, comprising:
    administering a chemotherapeutic agent selected from the group consisting of taxanes, alkylating agents, topoisomerase inhibitors, antimetabolites, and any combination thereof, to a tumor endothelial cell having a de-repressed ASMase;
wherein administration of the chemotherapeutic agent results in greater level of apoptosis of the tumor endothelial cell compared to a control tumor endothelial cell in which the ASMase is not de-repressed.

2. The method of claim 1, wherein the tumor endothelial cell is within a tumor of a subject.

3. The method of claim 2 wherein ASMase de-repression results in increased ASMase activity in the tumor endothelial cell in response to the chemotherapeutic agent, said ASMase activity measured using dynamic intravoxel incoherent motion (IVIM)-based diffusion-weighted magnetic resonance imaging (DW-MRI).

4. The method of claim 2, wherein the tumor is selected from the group consisting of adrenal, anal, bile duct, bladder, bone, brain/CNS, breast, cervical, colon/rectum, endometrial, esophageal, eye, gallbladder, gastrointestinal, kidney, heart, head and neck, laryngeal and hypopharyngeal, liver, lung, oral mesothelioma, nasopharyngeal, neuroblastoma, ovarian, pancreatic, peritoneal, pituitary, prostate, retinoblastoma, rhabdomyosarcoma, salivary gland, sarcoma, skin, small intestine, stomach, soft tissue sarcoma, rhabdomyosarcoma, testicular, thymus, thyroid, parathyroid, uterine, and vaginal tumors and metastases thereof.

5. The method of claim 2, wherein ASMase de-repression is determined by dynamic intravoxel incoherent motion (IVIM)-based diffusion-weighted magnetic resonance imaging (DW-MRI).

6. The method of claim 5, wherein the parameter of the IVIM DW-MRI is perfusion fraction (f) or pseudo-diffusion coefficient (D*), and wherein:
    a) the perfusion fraction (f) in the tumor decreases by at least 30%; or
    b) the pseudo-diffusion coefficient (D*) in the tumor decreases by at least 24%
    as compared to baseline.

7. The method of claim 2, wherein ASMase de-repression results in increased ASMase activity as measured by a radioenzymatic assay using the serum of said subject as sample and [$^{14}$C-methylcholine] sphingomyelin as substrate.

8. The method of claim 7, wherein ASMase activity is at least 1.2-fold, or at least 2-fold of baseline.

9. The method of claim 2, wherein ASMase de-repression results in reduced tumor capillary perfusion, as measured by Electron paramagnetic resonance (EPR) spectroscopic of O2 level.

10. The method of claim 9, wherein the O2 level is reduced by at least 29% from baseline.

11. The method of claim 2, wherein the chemotherapeutic agent results in a greater reduction in tumor growth relative to that observed with treatment of the chemotherapeutic agent on a tumor in which the ASMase is not de-repressed.

12. The method of claim 1 wherein ASMase de-repression results in an increase of a pro-apoptotic ceramide in response to the chemotherapeutic agent.

13. The method of claim 1, wherein ASMase de-repression is the result of reduced vascular endothelial growth factor (VEGF) signaling in the tumor endothelial cell.

14. The method of claim 13, wherein the tumor endothelial cell comprises reduced VEGF compared to baseline.

15. The method of claim 1, comprising measuring the level of pro-apoptotic ceramide after the administration of the chemotherapeutic agent.

16. The method of claim 1, wherein the ASMase of the tumor endothelial cell is capable of being de-repressed again within 120 hours.

17. The method of claim 1, comprising one or more additional administrations(s) of the chemotherapeutic agent to the tumor endothelial cell within 120 hours, and wherein the tumor endothelial cell has de-repressed ASMase at the time of the additional administration(s).

18. The method of claim 1, wherein ASMase de-repression results in the formation of ceramide-rich microdomain (CRM) in the tumor endothelial cell.

19. A method for increasing the efficacy of a chemotherapeutic agent, comprising:
    a) selecting a tumor endothelial cell having a de-repressed ASMase;
    b) treating the tumor endothelial cell with a chemotherapeutic agent selected from the group consisting of taxanes, alkylating agents, topoisomerase inhibitors, antimetabolites, and any combination thereof;
    wherein the chemotherapeutic agent results in greater level of apoptosis of the tumor endothelial cell than a control tumor endothelial cell in which the ASMase is not de-repressed.

20. The method of claim 19, wherein ASMase de-repression is the result of reduced VEGF signaling in the tumor endothelial cell.

21. The method of claim 20, wherein the tumor endothelial cell comprises reduced VEGF compared to baseline.

22. The method of claim 19, comprising one or more additional treatment of the chemotherapeutic agent within 120 hours, and wherein the tumor endothelial cell has the de-repressed ASMase at the time of the additional treatment.

23. A method for treating a tumor in a subject, comprising:
    administering a chemotherapeutic agent selected from the group consisting of taxanes, alkylating agents, topoisomerase inhibitors, antimetabolites, and any combination thereof, wherein the subject has a de-repressed ASMase,
and wherein administration of the chemotherapeutic agent results in a reduction of tumor size greater than that of a control tumor in a subject in which the ASMase is not de-repressed.

24. The method of claim 23, wherein ASMase de-repression is the result of reduced VEGF signaling in the subject.

25. The method of claim 24, wherein the subject comprises reduced free VEGF compared to baseline.

26. The method of claim 23, comprising one or more additional administration of the chemotherapeutic agent within 120 hours, and wherein the subject has the de-repressed ASMase at the time of the additional administration.

* * * * *